United States Patent [19]  
Slate et al.

[11] Patent Number: 5,053,747  
[45] Date of Patent: Oct. 1, 1991

[54] ULTRASONIC AIR-IN-LINE DETECTOR SELF-TEST TECHNIQUE

[75] Inventors: John B. Slate, Studio City; James L. Henke, Simi Valley, both of Calif.

[73] Assignee: Pacesetter Infusion, Inc., Sylmar, Calif.

[21] Appl. No.: 403,259

[22] Filed: Sep. 5, 1989

[51] Int. Cl.⁵ .................... G08B 29/00; A61B 8/00
[52] U.S. Cl. .................... 340/507; 340/573; 340/621; 73/598; 128/660.01; 128/912; 128/DIG. 6; 128/DIG. 13
[58] Field of Search ............. 340/507, 573, 591, 592, 340/603, 606, 621; 604/118, 67, 245; 128/660.01, 664, 912, DIG. 6, DIG. 13; 73/598, 599, 606, 615, 632, 609

[56] References Cited

U.S. PATENT DOCUMENTS 3,622,958 11/1971 Tucker et al. .
3,640,271 2/1972 Horton .................... 128/2.05 D
3,881,353 5/1975 Fathauer .................... 73/194 A
3,921,622 11/1975 Cole ........................ 128/2 V
3,974,681 8/1976 Namery .................... 73/67.5 R
3,974,683 8/1976 Martin .................... 73/432 PS
4,068,521 1/1978 Cosentino et al. .......... 73/19
4,079,736 3/1978 Lundquist ................. 340/573
4,083,225 4/1978 Day et al. .................. 73/19
4,112,735 9/1978 McKnight ................. 73/19
4,112,773 9/1978 Abts ....................... 73/642
4,127,114 11/1978 Bretscher ................ 128/2.05 N
4,138,879 2/1979 Liebermann ............... 73/19
4,142,414 3/1979 Cosentino ................. 73/216
4,208,906 6/1980 Roberts, Jr. ............... 73/155
4,235,095 11/1980 Liebermann ............... 73/19
4,237,720 12/1980 Abts ....................... 73/19
4,290,432 9/1981 Daniels .................... 128/660
4,319,580 3/1982 Colley et al. .............. 128/661
4,339,944 7/1982 Abts et al. ................ 73/19
4,354,500 10/1982 Colley et al. .............. 128/663
4,354,501 10/1982 Colley et al. .............. 128/663
4,354,502 10/1982 Colley et al. .............. 128/663
4,403,510 9/1983 de Walle et al. ............ 73/664
4,418,565 12/1983 St John ..................... 73/19
4,447,191 5/1984 Bilstad et al. .............. 417/12
4,448,207 5/1984 Parrish .................... 128/771
4,474,184 10/1984 Harui ...................... 128/660
4,487,601 12/1984 Lindemann ............... 604/122
4,501,531 2/1985 Bilstad et al. .............. 417/63
4,528,853 7/1985 Lerch et al. ................ 73/624
4,530,077 7/1985 Dorr ....................... 367/140
4,555,951 12/1985 Gutterman ............... 73/861.28
4,567,749 2/1986 Amblard et al. ............ 73/19
4,610,164 9/1986 Sobue et al. ............... 73/290 V
4,668,945 5/1987 Aldrovandi et al. ......... 340/621
4,673,927 6/1987 Cianiavicchia et al. ...... 340/621
4,689,986 9/1987 Carson et al. .............. 73/19
4,696,191 9/1987 Claytor et al. ............. 73/600
4,722,224 2/1988 Scheller et al. ............ 73/599
4,730,493 3/1988 Lebaud et al. ............. 73/599
4,752,289 6/1988 Balding et al. ............. 340/573
4,758,228 7/1988 Williams ................... 604/153
4,763,525 8/1988 Cobb ....................... 73/599
4,764,166 8/1988 Spani ...................... 604/65
4,821,558 4/1989 Pastrone et al. ............ 73/19
4,877,034 10/1989 Atkins et al. ............... 340/573

Primary Examiner—Donnie L. Crosland  
Attorney, Agent, or Firm—Leslie S. Miller

[57] ABSTRACT

An ultrasonic air-in-line detection system for use in detecting air bubbles in the fluid line of a disposable cassette mounted on a main pump unit is disclosed in which a self-test procedure is periodically used to ensure that any faults in the ultrasonic air-in-line detector which do not fail safe are automatically detected. After a pumping cycle is completed, if the ultrasonic air-in-line detector indicates that there is fluid in the fluid line at the location of the ultrasonic sensor, the operating frequency of the transmitting ultrasonic transducer is changed to a non-resonant frequency for the self-test procedure. If the ultrasonic air-in-line detector still produces a signal indicating that there is fluid in the line, this indicates that there is a failure in the ultrasonic detector and a fault is indicated and the system is shut down.

16 Claims, 19 Drawing Sheets

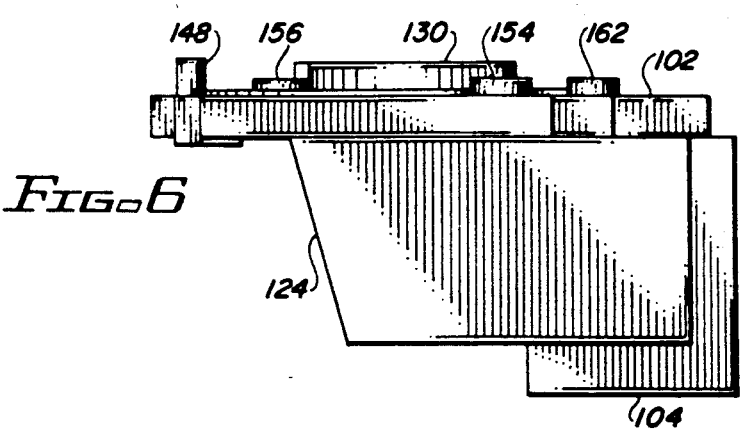
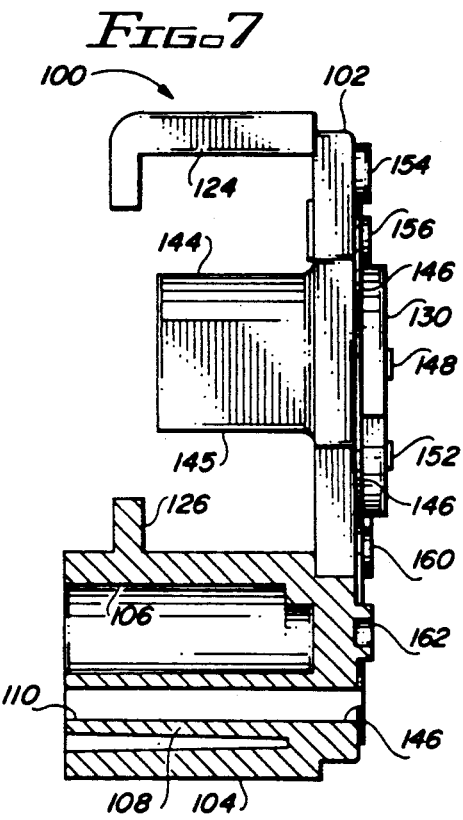
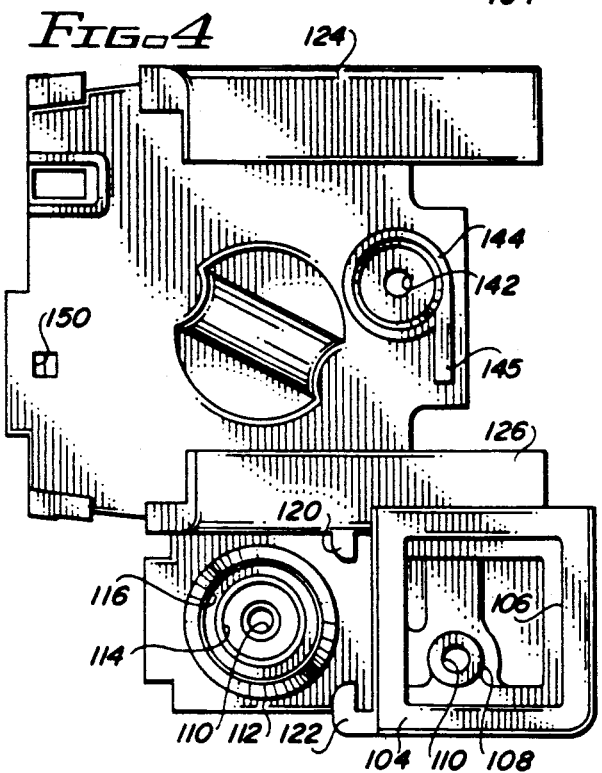
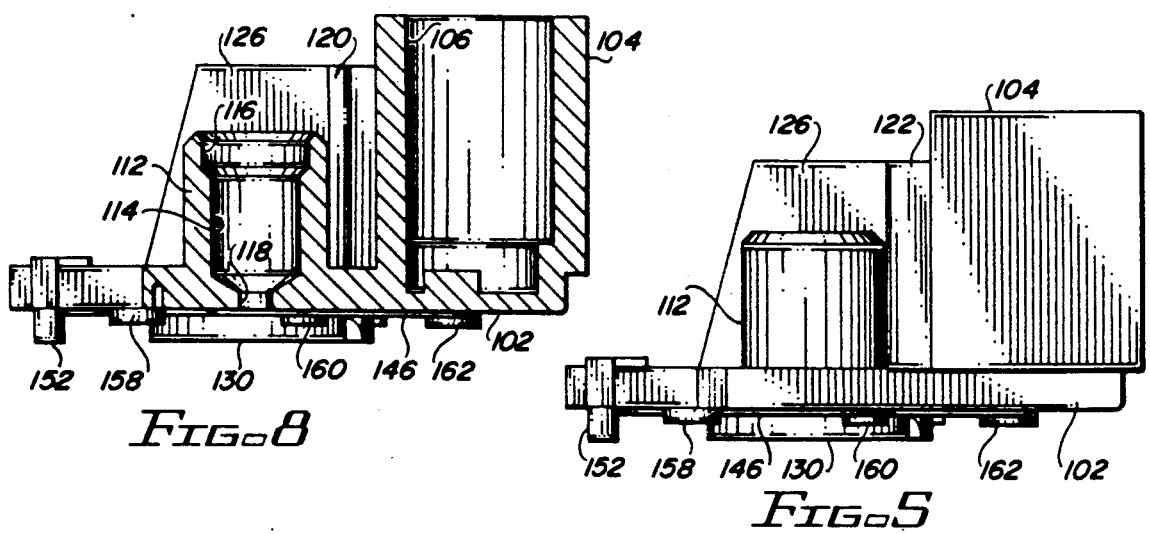

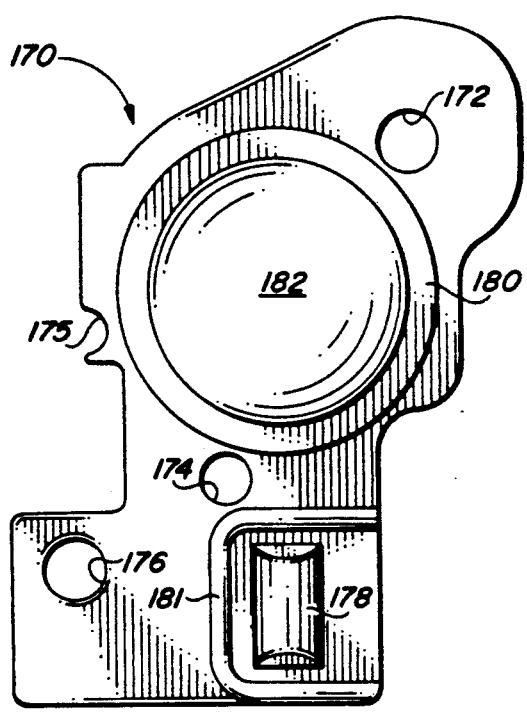
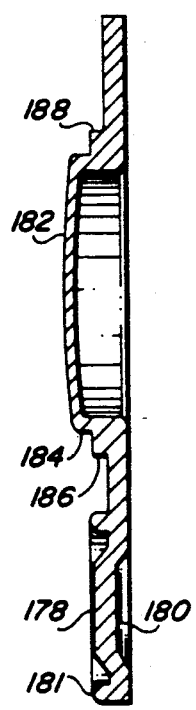
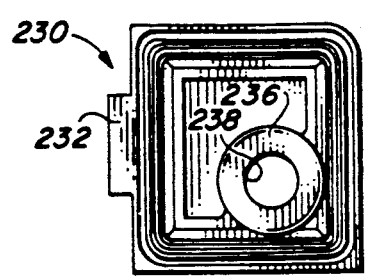
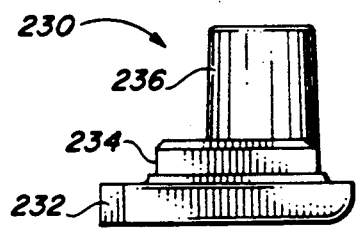
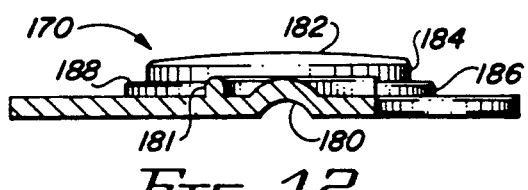
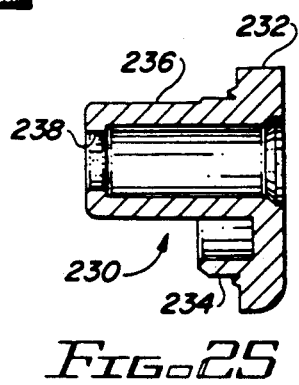
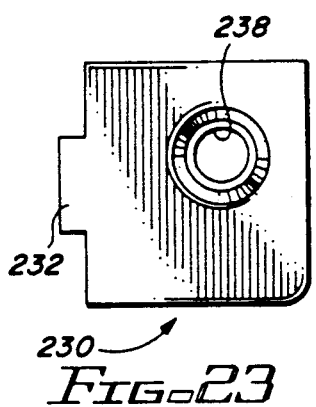
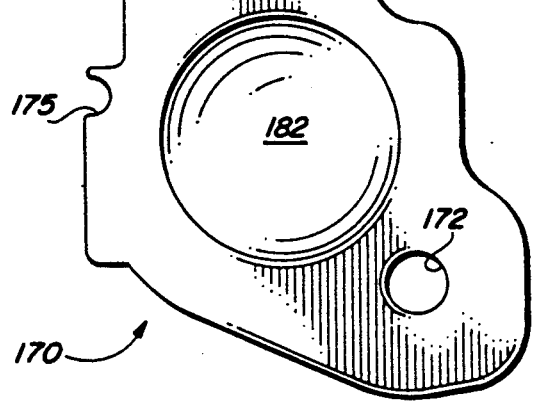
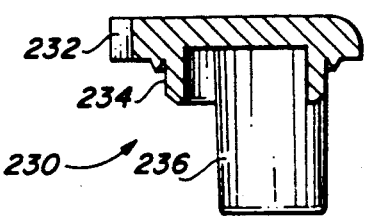

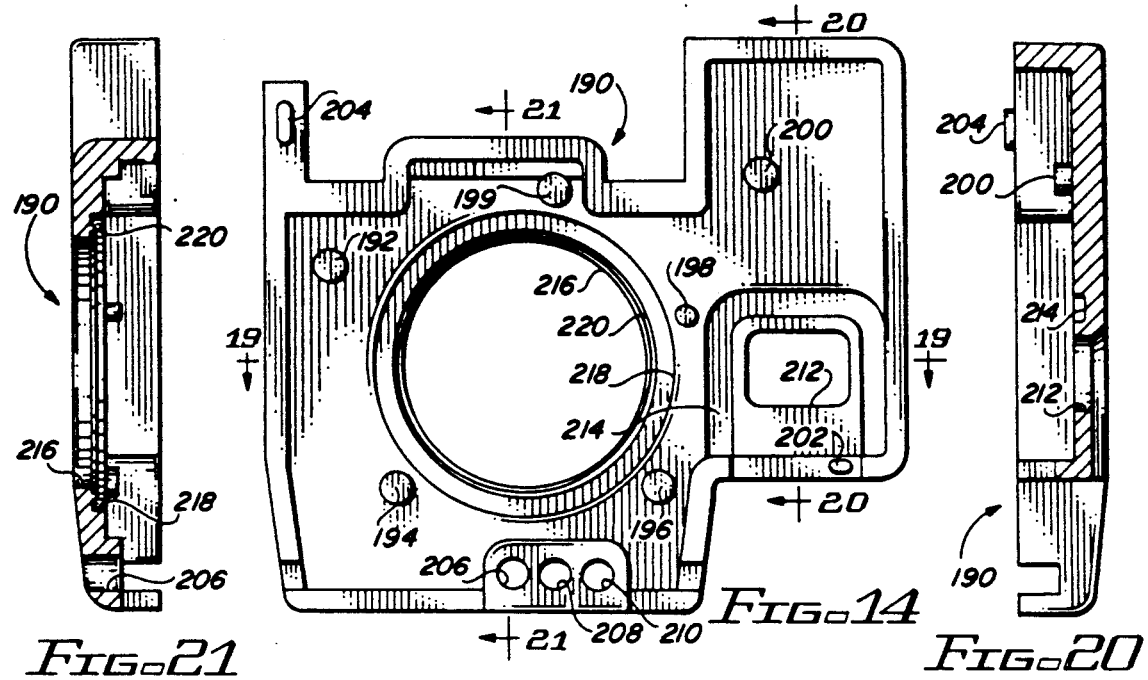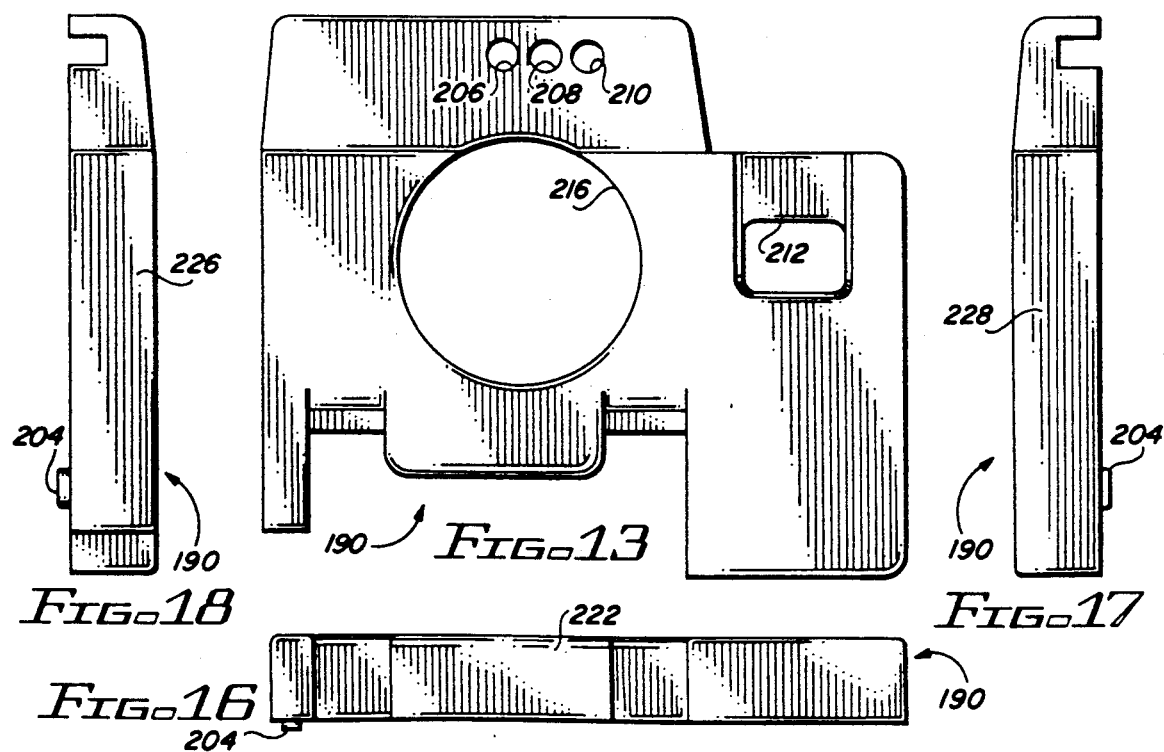

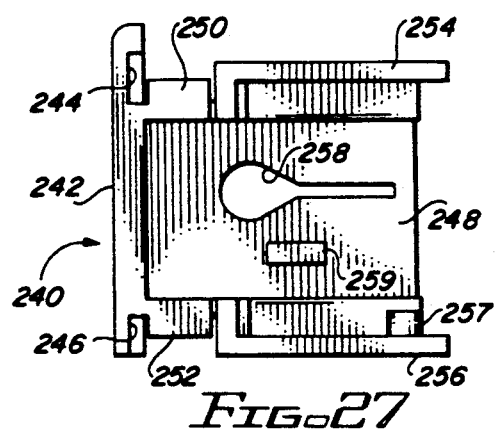
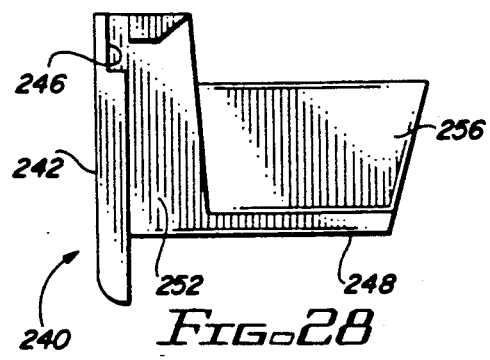
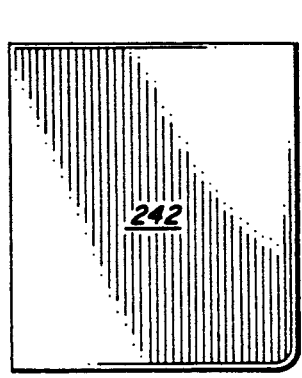
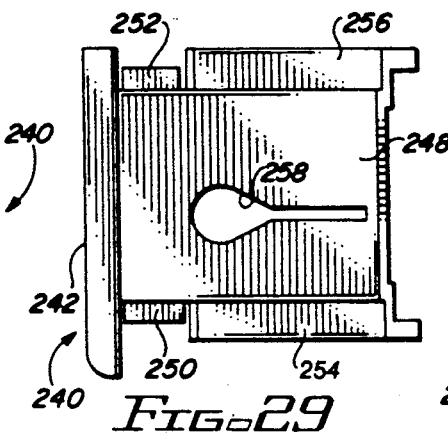
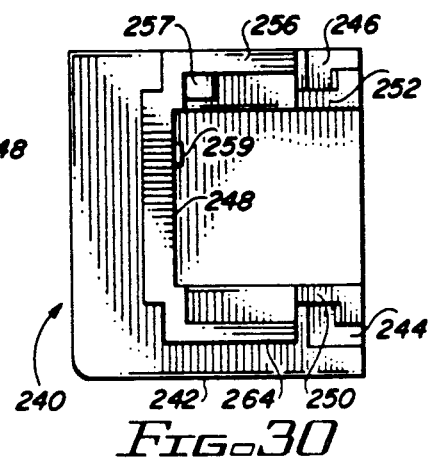
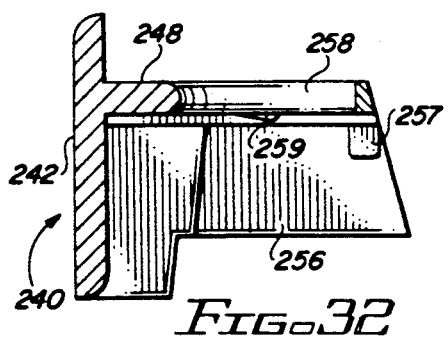
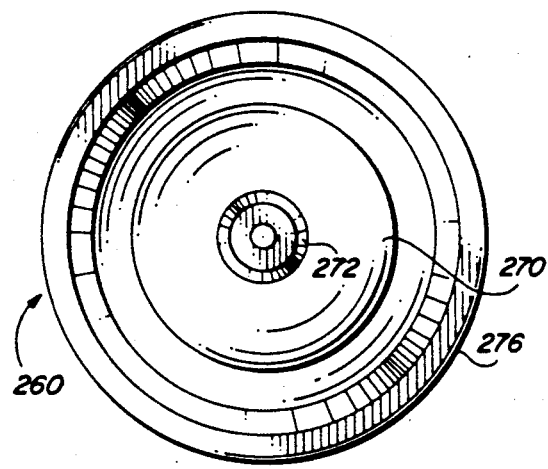
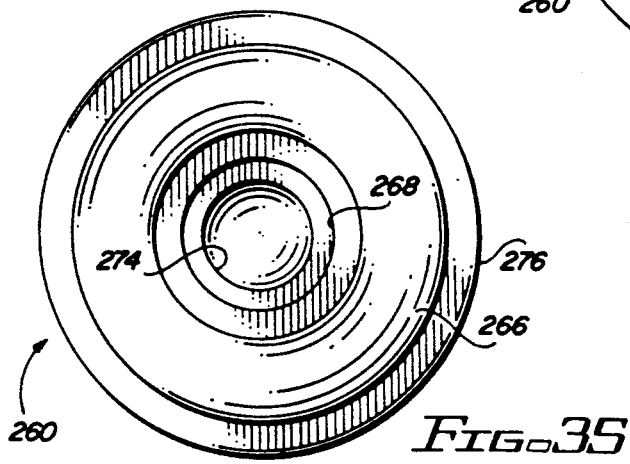

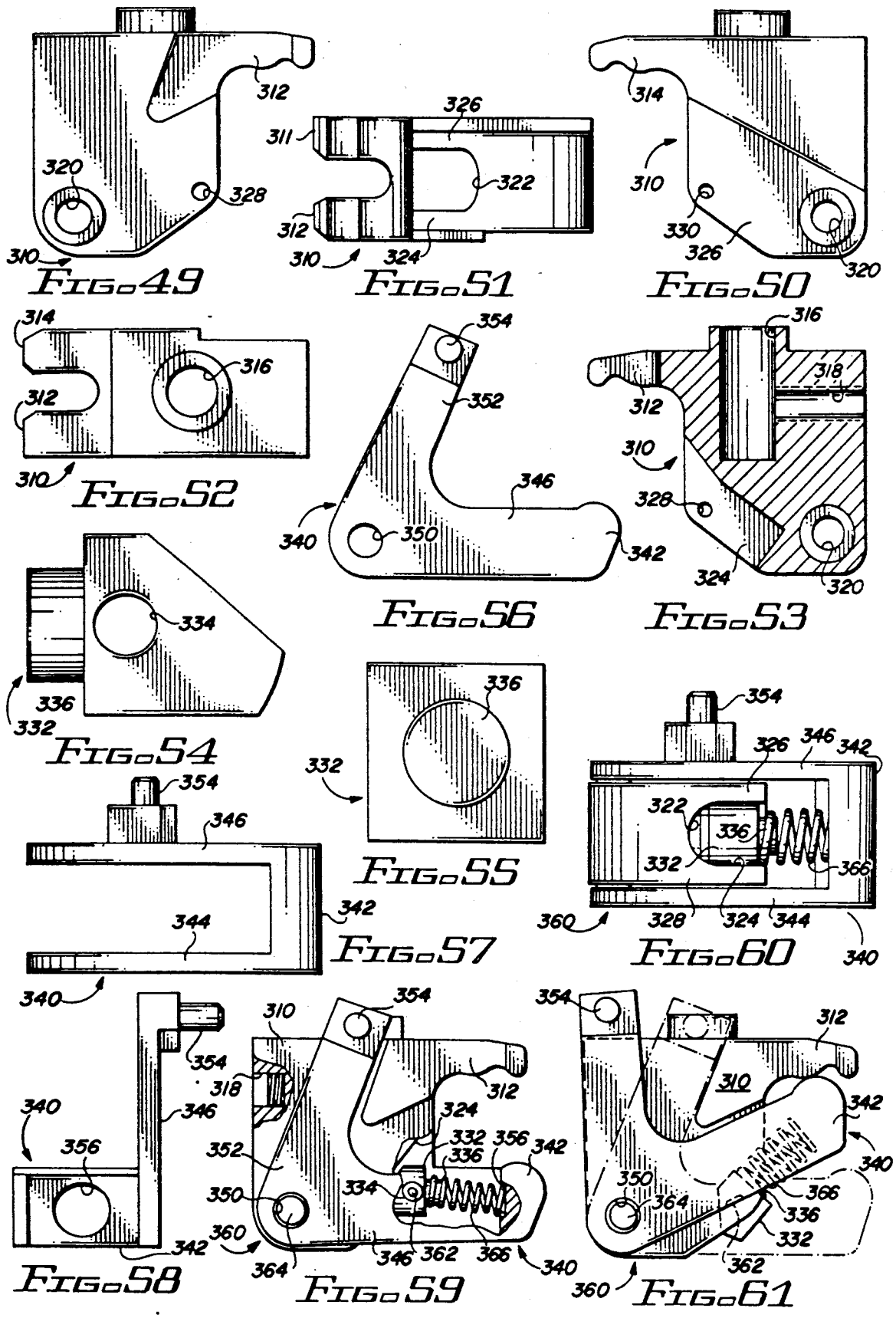

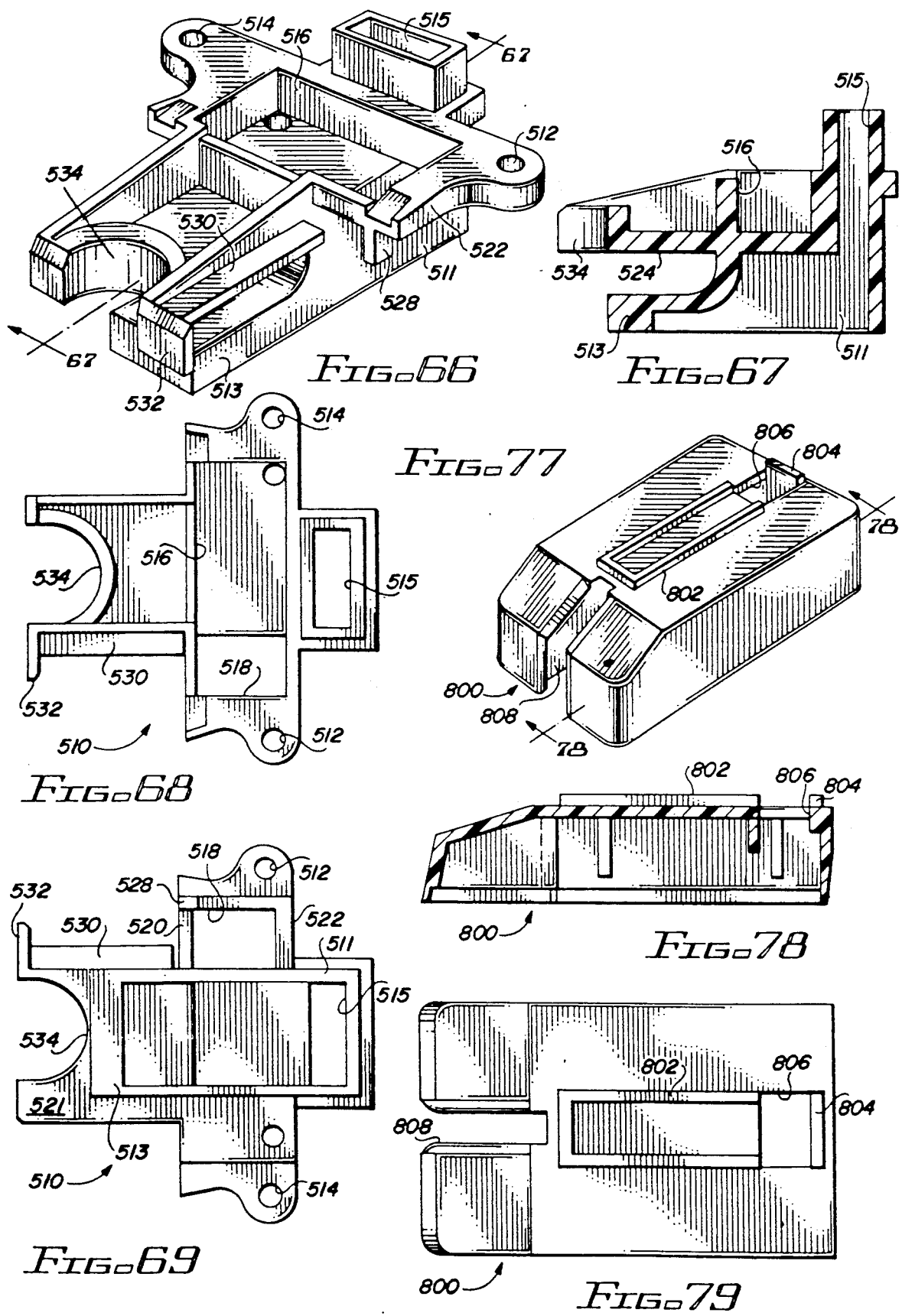

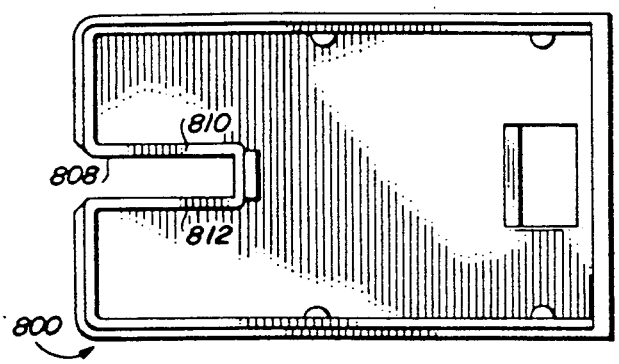
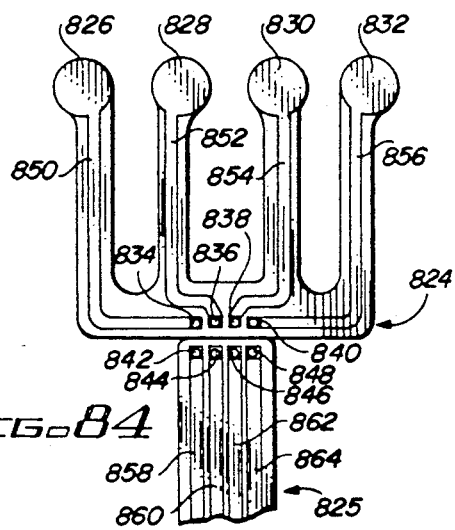
FIG. 80
FIG. 81
FIG. 84
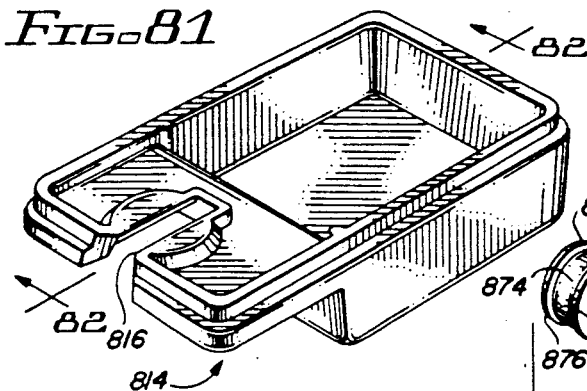
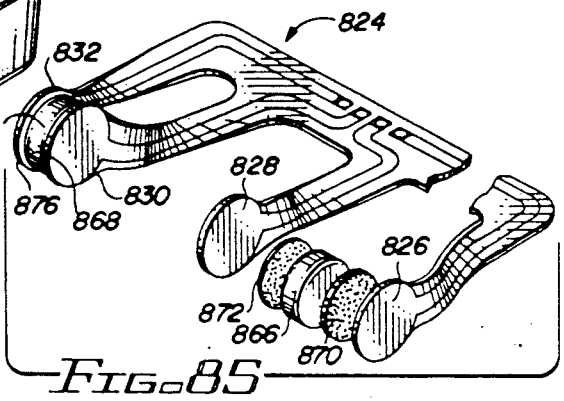
FIG. 82
FIG. 85
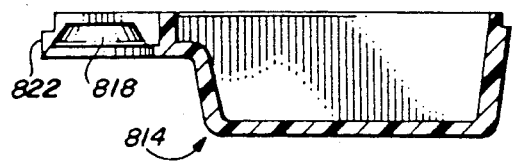
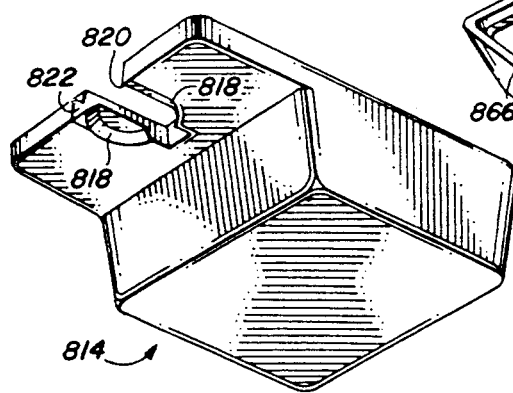
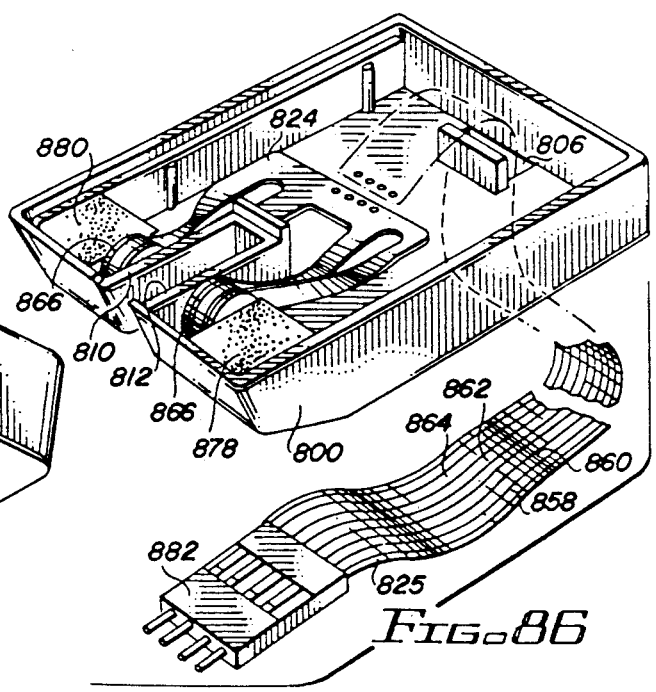
FIG. 83
FIG. 86

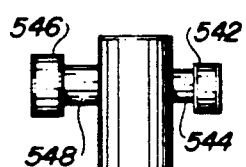
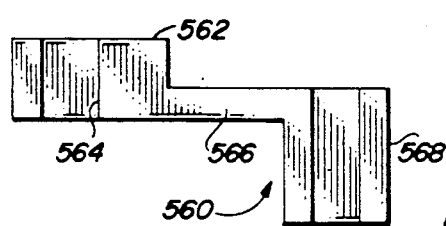
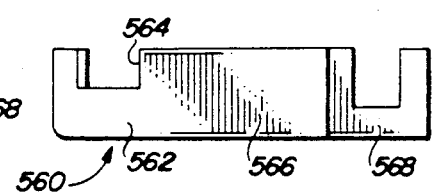
FIG.70   FIG.71   FIG.72
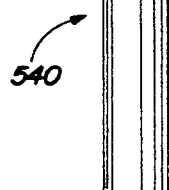
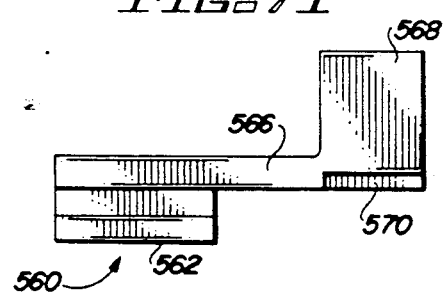
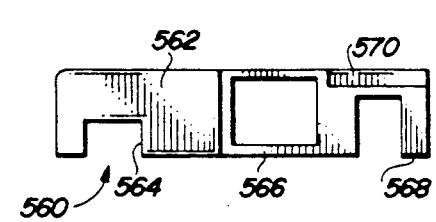
FIG.73   FIG.74
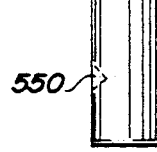
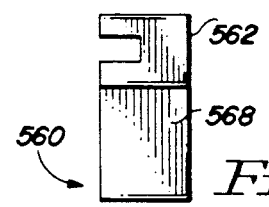
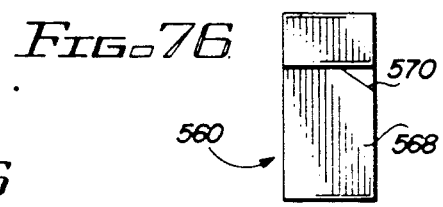
FIG.75   FIG.76
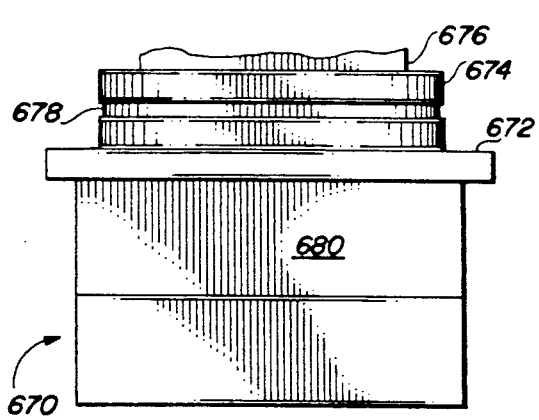
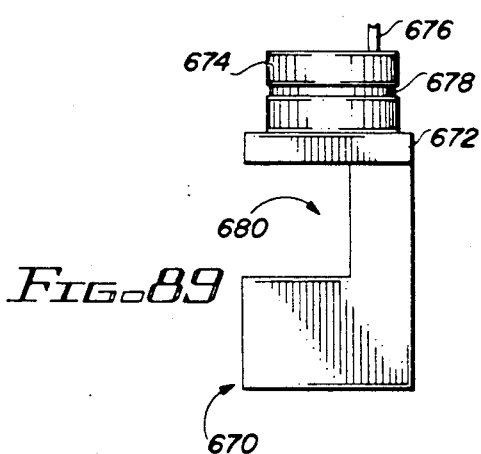
FIG.88   FIG.89
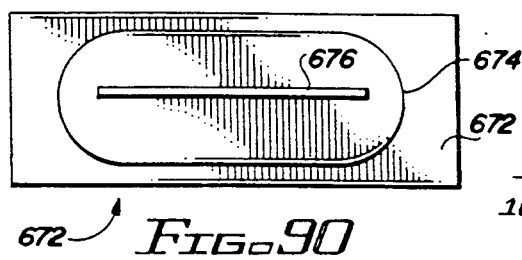
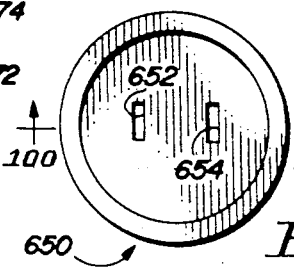
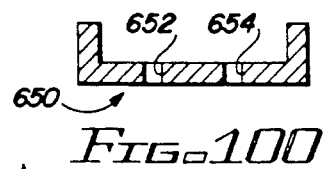
FIG.90   FIG.99   FIG.100

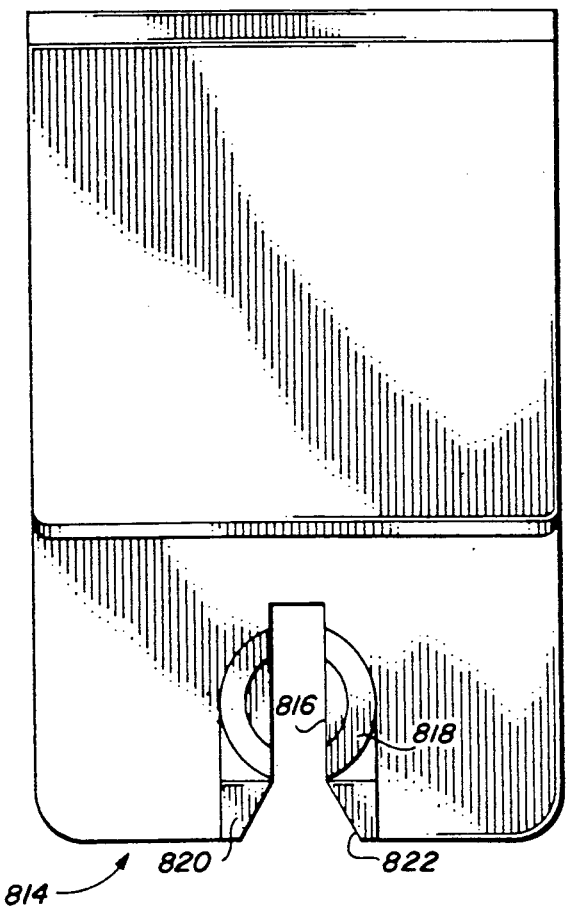
FIG. 83A
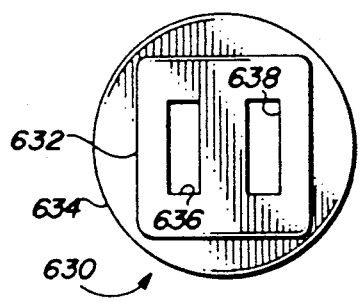
FIG. 94
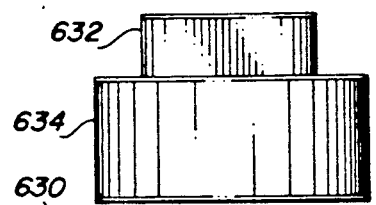
FIG. 95
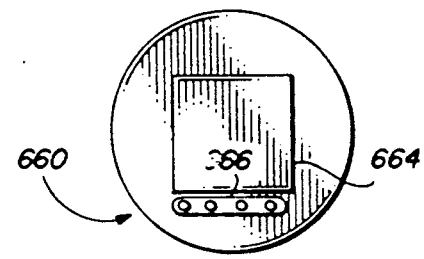
FIG. 96
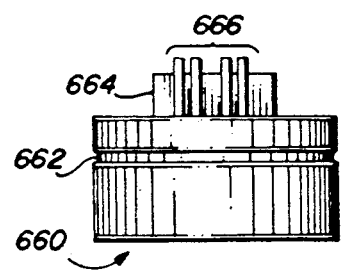
FIG. 97
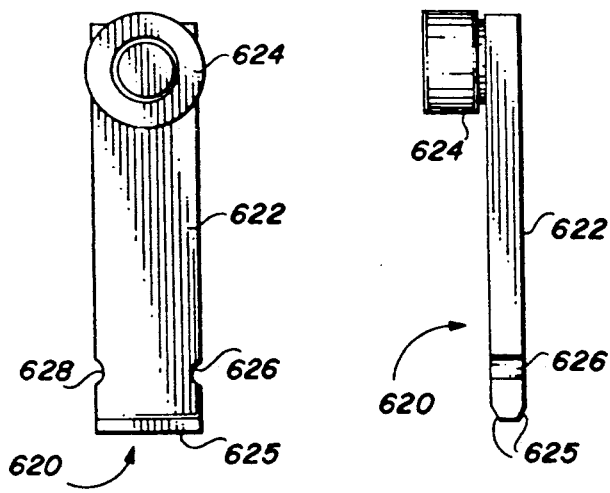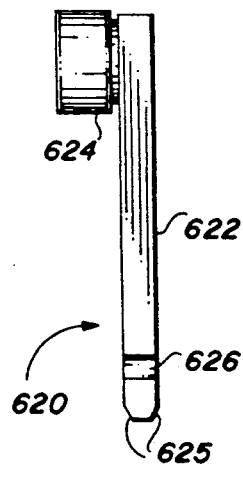
FIG. 91   FIG. 92
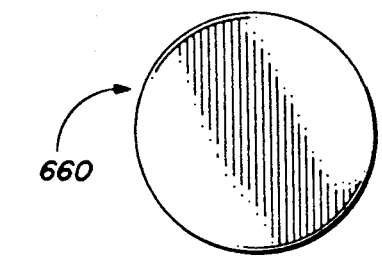
FIG. 98
FIG. 93

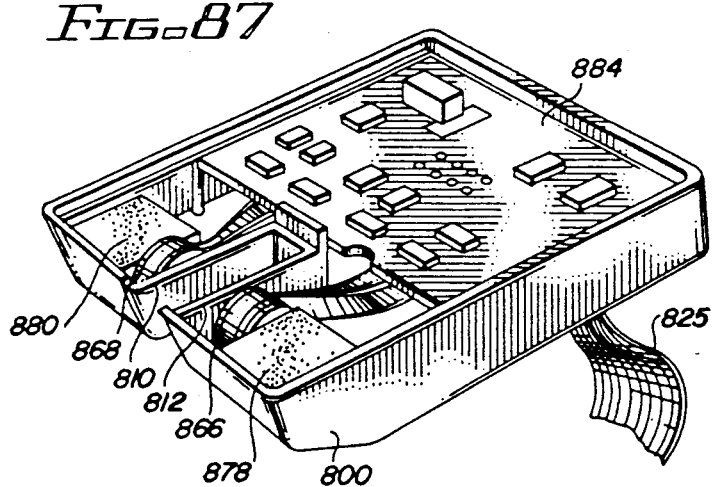
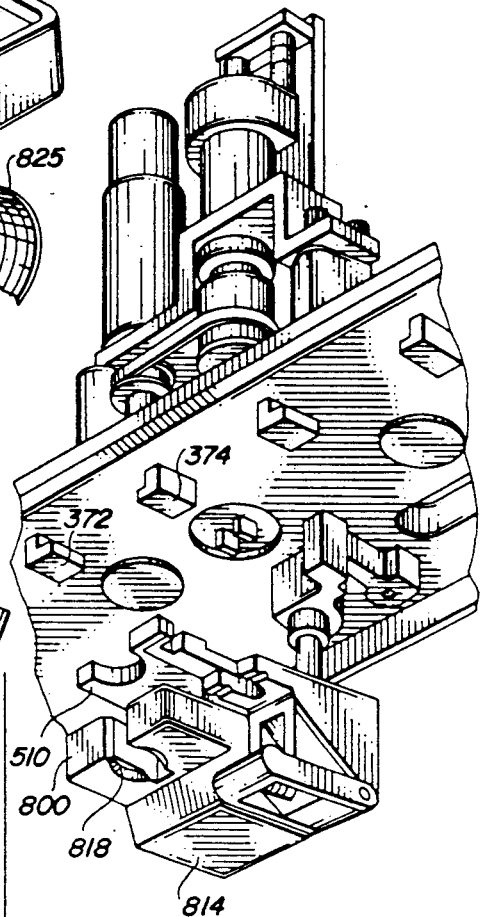
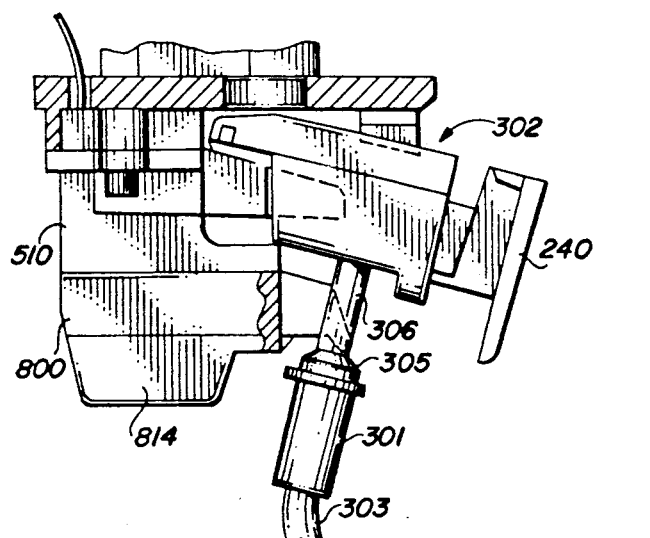
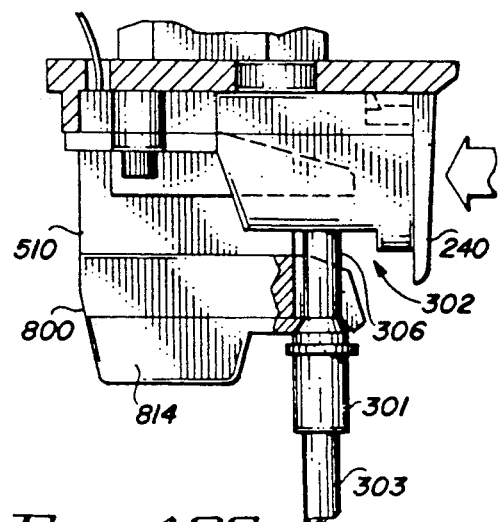

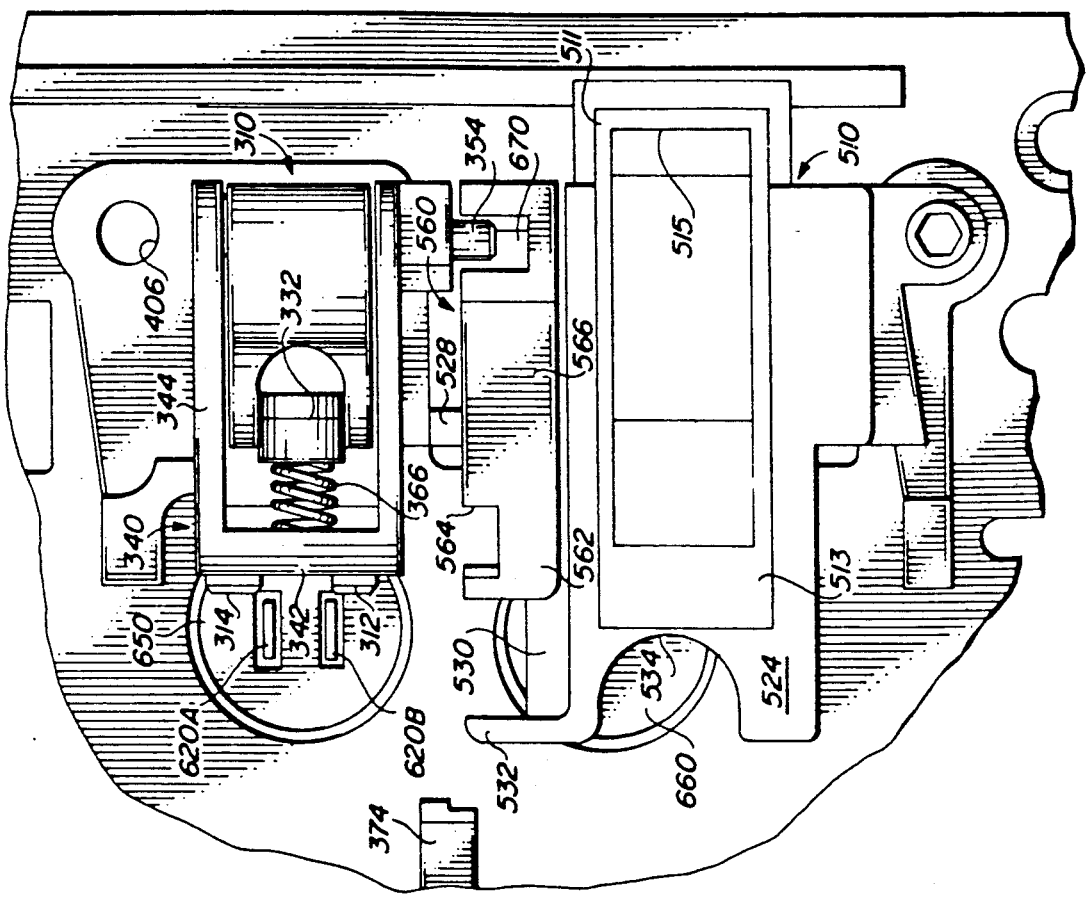
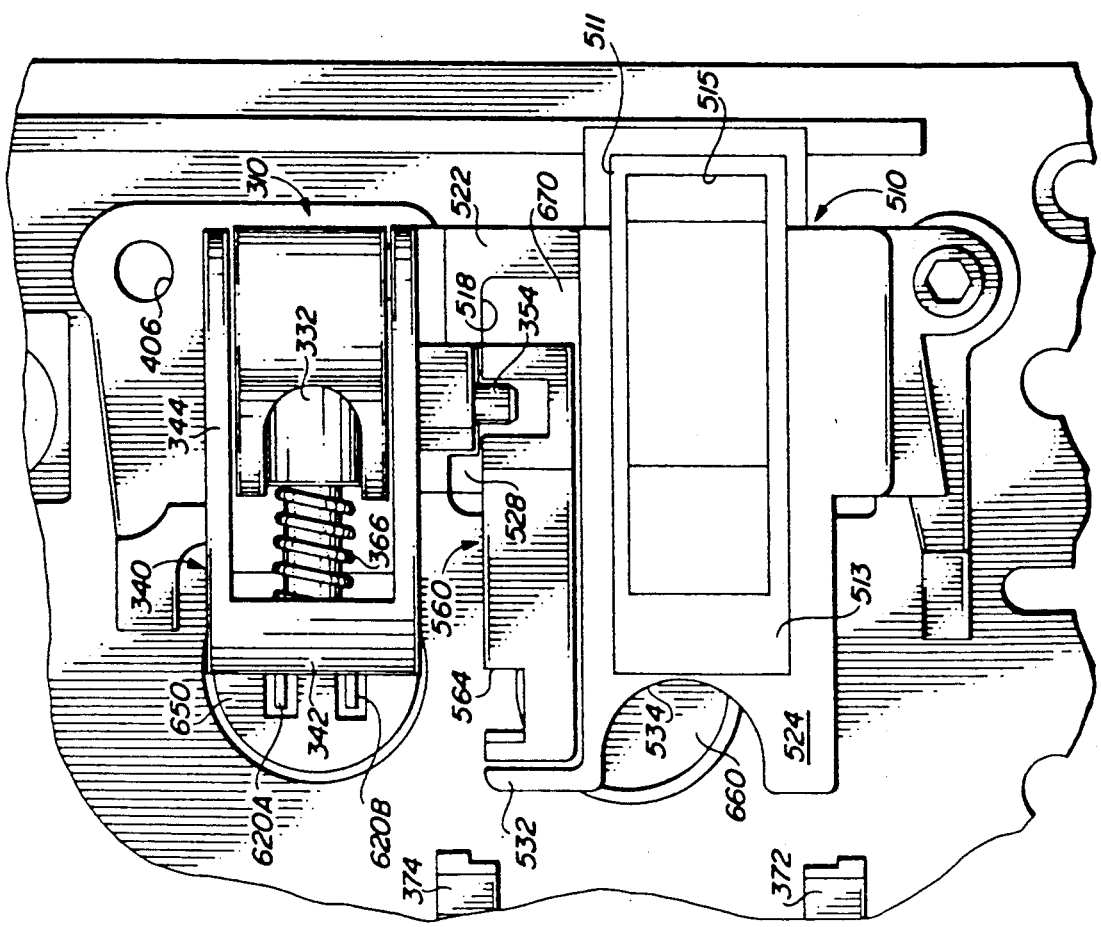

ULTRASONIC AIR-IN-LINE DETECTOR SELF-TEST TECHNIQUE

IDENTIFICATION OF RELATED PATENT APPLICATIONS

This application is related to seven other copending patent applications, all of which were filed on Dec. 1, 1987. These patent applications are U.S. Ser. No. 127,333, entitled "Disposable Cassette for a Medication Infusion System," U.S. Ser. No. 127,350, entitled "Piston Cap and Boot Seal for a Medication Infusion System," U.S. Ser. No. 128,122, entitled "Pressure Diaphragm for a Medication Infusion System," U.S. Ser. No. 128,009, entitled "Cassette Optical Identification Apparatus for a Medication Infusion System," U.S. Ser. No. 128,121, entitled "Air-In-Line Detector for a Medication Infusion System," U.S. Ser. No. 127,359, entitled "Cassette Loading and Latching Apparatus for a Medication Infusion System," and U.S. Ser. No. 127,133, entitled "Mechanical Drive System for a Medication Infusion System."

This application is also related to four other filed copending patent applications, all of which were filed on Dec. 4, 1987. These patent applications are U.S. Ser. No. 128,973, entitled "Fluid Delivery Control and Monitoring Apparatus for a Medication Infusion System," U.S. Ser. No. 128,966, entitled "Clinical Configuration of Multimode Medication Infusion System," U.S. Ser. No. 128,978, entitled "User Interface for Medication Infusion System," and U.S. Ser. No. 129,013, entitled "Patient-Side Occlusion Detection System for a Medication Infusion System."

This application is also related to three other concurrently filed copending patent applications. These patent applications are U.S. Ser. No. 404,027, entitled "Automatic Tubing Lock for Ultrasonic Sensor Interface," U.S. Ser. No. 403,418, entitled "Ultrasonic Transducer Electrical Interface Assembly," and U.S. Ser. No. 403,512, entitled "Ultrasonic Air-In-Line Detector for a Medication Infusion System."

BACKGROUND OF THE INVENTION

1. Field of the Invention

The present invention relates generally to an ultrasonic system for detecting the presence of air in a fluid line, and more particularly to a self-test procedure for ensuring that any faults in the ultrasonic air-in-line detector which do not fail safe are automatically detected by periodically performing a self-test procedure.

In the past there have been two primary techniques which have been used to deliver drugs which may not be orally ingested to a patient. The first such technique is through an injection, or shot, using a syringe and needle which delivers a large dosage at relatively infrequent intervals to the patient. This technique is not always satisfactory, particularly when the drug being administered is potentially lethal, has negative side effects when delivered in a large dosage, or must be delivered more or less continuously to achieve the desired therapeutic effect. This problem results in smaller injections being given at more frequent intervals, a compromise approach not yielding satisfactory results.

Alternatively, the second technique involves administering a continuous flow of medication to the patient, typically through an IV bottle. Medication may also be delivered through an IV system with an injection being made into a complex maze of IV tubes, hoses, and other paraphernalia. With drop counters being used to meter the amount of bulk fluid delivered, many medications still end up being administered in a large dosage through an injection into the IV lines, although the medications may be diluted somewhat by the bulk fluid.

As an alternative to these two techniques of administering medication to a patient, the relatively recent addition of medication infusion pumps has come as a welcome improvement. Medication infusion pumps are utilized to administer drugs to a patient in small, metered doses at frequent intervals or, alternatively, in the case of some devices, at a low but essentially continuous rate. Infusion pump therapy may be electronically controlled to deliver precise, metered doses at exactly determined intervals, thereby providing a beneficial gradual infusion of medication to the patient. In this manner, the infusion pump is able to mimic the natural process whereby chemical balances are maintained more precisely by operating on a continuous time basis.

One of the requirements of a medication infusion system is dictated by the important design consideration of disposability. Since the portion of the device through which medication is pumped must be sterile, in most applications of modern medication infusion equipment some portions of the equipment are used only once and then disposed of, typically at regular intervals such as once daily. It is therefore desirable that the fluid pump portion of the infusion pump device be disposable, with the fluid pump being designed as an attachable cassette which is of inexpensive design, and which is easily installable onto the main pump unit.

It will be perceived that it is desirable to have a simple disposable cassette design to minimize the cost of construction of the cassette, using the minimum number of parts necessary in the design of the cassette. The design of the cassette must be mass producible, and yet result in a uniform cassette which is capable of delivering liquid medication or other therapeutic fluids with a high degree of accuracy. The cassette should include therein more than just a fluid pump; other features which have formerly been included in peripheral devices may be included in the cassette.

Such a system has been disclosed in all of the above-identified previously filed related applications. Of these applications, U.S. Ser. No. 128,121, entitled "Air-In-Line Detector for a Medication Infusion System," is hereby incorporated herein by reference.

An essential function of a medication infusion system is to avoid the infusion of fluid containing more than a minimal amount of air bubbles therein. Although steps may be taken to minimize the possibility of air bubbles being contained in a fluid which is to be infused to a patient, it is essential to monitor the fluid line before it reaches the patient to ensure that air bubbles remain in the fluid which is to be infused are detected. The detection of air bubbles in all fluids which are to be infused is therefore a critical design requirement.

One type of air-in-line detector which has been used in the past is an ultrasonic detector, which places an ultrasonic transmitter on one side of a fluid line and an ultrasonic receiver on the other side of the fluid line. Fluid is a good conductor of ultrasonic energy while air or foam is not. Accordingly, if there is an air bubble in the fluid line between the transmitter and the receiver, the signal strength will be greatly attenuated, and the presence of the bubble will be indicated. Examples of ultrasonic air-in-line detectors include U.S. Pat. No.

4,764,166, to Spani, and U.S. Pat. No. 4,821,558, to Pastrone et al.

It will at once be realized by those skilled in the art that the ultrasonic air-in-line detector is a critical component of the medication infusion system. As such, all possible failures of the ultrasonic air-in-line detector must either fail-safe or be promptly detected. An example of a fail-safe condition is the failure of one of the transducers, in which case the system will indicate that air is present in the fluid line even when fluid is present. Other than fail-safe failures are those which would indicate that fluid is present in the fluid line when in fact air is present. Such failures should be promptly detected by the system, although the references cited above are silent as to any apparatus or procedure for detecting non fail-safe failures.

There are two known non-fail-safe conditions known to occur in an ultrasonic air-in-line detector. The first of these non-fail-safe failures is when the output of the receiver is stuck high. This occurs typically because there is a short in the receiver to $V_{CC}$. If this situation occurs, the output of the ultrasonic air-in-line detector will remain high indicating the presence of fluid in the fluid line even when air is in the fluid line.

The second known fail-safe failure is when there is electrical coupling between the transmitter and either of the ultrasonic receiver transducer, the receiver circuitry, or the digital output circuitry following the receiver circuitry. This may occur due to situations such as shorts, stray capacitance, or stray inductance. Such electrical coupling may have a bandwidth anywhere from DC to MHz. Either such electrical coupling or a receiver which is stuck high will thus cause the ultrasonic air-in-line detector system to indicate that there is fluid in the line when in fact there is air in the line.

It is therefore the primary objective of the present invention to provide a self-test system which will detect all such non-fail-safe occurrences. Thus, the self-test system must detect the occurrence of a receiver output stuck high and provide an alarm and shut down the pumping system. The self-test system must also detect the occurrence of electrical coupling which causes a false indication of the presence of fluid in the fluid line, and provide an alarm and shut down the pumping system.

Such a self-test must be performed periodically, and sufficiently often to ensure that such a failure will be detected promptly before air can be pumped into the patient. The self-test system must use as few additional components as possible, and require no modification to the cassette, yet which afford the highest degree of accuracy in detecting a system fault. The system of the present invention must provide all of these advantages and overcome the limitations of the background art without incurring any relative disadvantage.

SUMMARY OF THE INVENTION

The disadvantages and limitations of the background art discussed above are overcome by the present invention. With this invention, a self-test system is implemented to determine the presence of failure modes which cause the ultrasonic air-in-line detector system to indicate the presence of fluid when in fact there is air in the line. The self-test procedure requires the addition of no components to the system; rather, a novel use of the existing components is detailed which results in the identification of the non-fail-safe failure modes described above.

The self-test is performed once every pump cycle, at the end of the pumping sequence. The air-in-line detector is checked to see if it indicates the presence of air in the fluid line. If air is indicated in the fluid line, the self-test procedure is not performed. However, if the air-in-line detector indicates the presence of air in the fluid line the self-test procedure is initiated.

First, the frequency used to excite the ultrasonic transmitter transducer is changed from a resonant frequency or frequency range which encompasses its resonant frequency to a frequency which is far from a resonant frequency of the ultrasonic transmitter transducer. Thus, by taking advantage of the narrow bandwidth of the ultrasonic transducers, the ultrasonic transmitter transducer will not transmit a signal at all to the ultrasonic receiver transducer. The ultrasonic receiver transducer should not produce an output signal indicating that the signal from the ultrasonic transmitter transducer has passed through the fluid line.

The system should then produce an output indicating the presence of air in the fluid line. This will occur due to the non-resonant frequency utilized. If there is one of the non-fail-safe faults discussed above, the system will still indicate the presence of fluid in the fluid line, since a short or electrical crosstalk are not dependent on the frequency with which the ultrasonic transmitter transducer is driven.

Thus, if there is an output from the system indicating the presence of fluid in the fluid line, there is clearly an error in the system. In this case, a fault is indicated and the pumping system is shut down. If the system indicated that there was air in the fluid line due to the use of the non-resonant frequency, a correct response occurred and the medication infusion system is allowed to continue, after the frequency is reset to the resonant frequency or resonant frequency range.

It may therefore be appreciated that the present invention provides a self-test system which will detect all such non-fail-safe occurrences. Thus, the self-test system will detect the occurrence of a receiver output stuck high and provide an alarm and shut down the pumping system. The self-test system also will detect the occurrence of electrical coupling which causes a false indication of the presence of fluid in the fluid line, and provide an alarm and shut down the pumping system.

The self-test system performs the self-test periodically, and sufficiently often to ensure that such a failure will be detected promptly before air can be pumped into the patient. The self-test system uses no additional components, and requires no modification to the cassette, yet it affords the highest degree of accuracy in detecting a system fault. The system of the present invention provides these advantages and overcome the limitations of the background art without incurring any relative disadvantage whatsoever.

DESCRIPTION OF THE DRAWINGS

In the detailed description of the preferred embodiment a uniform directional system is used in which front, back, top, bottom, left, and right are indicated with respect to the operating position of the cassette and main pump unit when viewed from the front of the main pump unit. These and other advantages of the present invention are best understood with reference to the drawings, in which:

FIG. 4 is a bottom view of the cassette body shown in FIGS. 1 through 3;

FIG. 5 is a right side view of the cassette body shown in FIGS. 1 through 4;

FIG. 6 is a left side view of the cassette body shown in FIGS. 1 through 5;

FIG. 7 is a partially cutaway view from the front side of the cassette body shown in FIGS. 1 through 6, showing the bubble trap used to remove air bubbles from the fluid supplied to the cassette;

FIG. 8 is a partially cutaway view from the right side of the cassette body shown in FIGS. 1 through 6, showing the cylinder of the fluid pump contained in the cassette;

FIG. 9 is a top plan view of a valve diaphragm used to seal the passageways on the top surface of the cassette body shown in FIG. 1, to function as the pressure diaphragm, and also to function as the valves for the pump;

FIG. 10 is a bottom view of the valve diaphragm shown in FIG. 9;

FIG. 11 is a cutaway view from the back side of the valve diaphragm shown in FIGS. 9 and 10;

FIG. 12 is a cutaway view from the right side of the valve diaphragm shown in FIGS. 9 and 10;

FIG. 13 is a top plan view of a valve diaphragm retainer used to retain the valve diaphragm shown in FIGS. 9 through 12;

FIG. 14 is a bottom view of the valve diaphragm retainer shown in FIG. 13;

FIG. 15 is a back side view of the valve diaphragm retainer shown in FIGS. 13 and 14;

FIG. 16 is a front side view of the valve diaphragm retainer shown in FIGS. 13 through 15;

FIG. 17 is a right side view of the valve diaphragm retainer shown in FIGS. 13 through 16;

FIG. 18 is a left side view of the valve diaphragm retainer shown in FIGS. 13 through 17;

FIG. 19 is a cutaway view from the front side of the valve diaphragm retainer shown in FIGS. 13 through 18;

FIG. 20 is a cutaway view from the left side of the valve diaphragm retainer shown in FIGS. 13 through 19;

FIG. 21 is a cutaway view from the right side of the valve diaphragm retainer shown in FIGS. 13 through 20;

FIG. 22 is a top view of a bubble chamber cap;

FIG. 23 is a bottom view of the bubble chamber cap shown in FIG. 22;

FIG. 24 is a left side view of the bubble chamber cap shown in FIGS. 22 and 23;

FIG. 25 is a cutaway view from the back side of the bubble chamber cap shown in FIGS. 22 through 24;

FIG. 26 is a cutaway view from the right side of the bubble chamber cap shown in FIGS. 22 through 24;

FIG. 27 is a top plan view of a slide latch used both to lock the cassette in place on a main pump unit, and to pinch off the IV outlet line prior to installation on the main pump unit;

FIG. 28 is a right side view of the slide latch shown in FIG. 27;

FIG. 29 is a bottom view of the slide latch shown in FIGS. 27 and 28;

FIG. 30 is a back side view of the slide latch shown in FIGS. 27 through 29;

FIG. 31 is a front side view of the slide latch shown in FIGS. 27 through 30;

FIG. 32 is a cutaway view from the left side of the slide latch shown in FIGS. 27 through 31;

FIG. 34 is a top end view of the piston cap and boot seal shown in FIG. 33;

FIG. 35 is a bottom end view of the piston cap and boot seal shown in FIGS. 33 and 34;

FIG. 49 is a left side view of the latch head used to capture and actuate the piston;

FIG. 50 is a right side view of the latch head shown in FIG. 49;

FIG. 51 is a bottom view of the latch head shown in FIGS. 49 and 50;

FIG. 52 is a top view of the latch head shown in FIGS. 49 through 51;

FIG. 53 is a cutaway view from the right side of the latch head shown in FIGS. 49 through 52;

FIG. 54 is a right side view of the spring retainer to be mounted in the latch head shown in FIGS. 49 through 52;

FIG. 55 is a front view of the spring retainer shown in FIG. 54;

FIG. 56 is a left side view of the latch jaw to be mounted on the latch head shown in FIGS. 49 through 52;

FIG. 57 is a bottom view of the latch jaw shown in FIG. 56;

FIG. 58 is a back view of the latch jaw shown in FIGS. 56 and 57;

FIG. 59 is a left side view of the jaws assembly in the open position, the jaws assembly being made up of the latch head shown in FIGS. 49 through 52, the spring retainer shown in FIGS. 54 and 55, the latch jaw shown in FIGS. 56 through 58, a latch spring, and pins used to assemble the various components together;

FIG. 60 is a bottom view of the jaws assembly shown in FIG. 59, with the jaws assembly being shown in the open position;

FIG. 61 is a left side view of the jaws assembly shown in FIGS. 59 and 60, with the jaws assembly being shown in the closed position (and in the open position in phantom lines);

FIG. 66 is a perspective top view of the cassette guide used to position the cassette of FIGS. 45 through 48 on the main pump unit;

FIG. 67 is a sectional view of the cassette guide shown in FIG. 66;

FIG. 68 is a top view of the cassette guide shown in FIGS. 66 and 67;

FIG. 69 is a bottom view of the cassette guide shown in FIGS. 66 through 68;

FIG. 70 is a left side plan view of the pump shaft on which is mounted the jaws assembly shown in FIGS. 59 through 61;

FIG. 71 is a right side view plan view of the slide lock used to retain the cassette shown in FIGS. 43 through 48 in position on the main pump unit;

FIG. 72 is a bottom view of the slide lock shown in FIG. 71;

FIG. 73 is left side view of the slide lock shown in FIGS. 71 and 72, showing the bevel used to reflect the light beam from the optical light source away from the optical light sensor when the slide lock is in the open position;

FIG. 74 is a top view of the slide lock shown in FIGS. 71 through 73, showing the reflective surface used to reflect the light beam from the optical light source to the optical light sensor when the slide lock is in the closed position;

FIG. 75 is a front side view of the slide lock shown in FIGS. 71 through 74;

FIG. 76 is a back side view of the slide lock shown in FIGS. 71 through 75, showing the slanted surface used to reflect the light beam away from the corresponding sensor when the slide look is in the open position;

FIG. 77 is a perspective top view of the upper sensor housing;

FIG. 78 is a sectional view of the upper sensor housing shown in FIG. 77;

FIG. 79 is a top view of the upper sensor housing shown in FIGS. 77 and 78;

FIG. 80 is a bottom view of the upper sensor housing shown in FIGS. 77 through 79;

FIG. 81 is a perspective top view of the lower sensor housing;

FIG. 82 is a sectional view of the lower sensor housing shown in FIG. 81;

FIG. 83 is a sectional bottom view of the lower sensor housing shown in FIGS. 81 and 82;

FIG. 83A is a bottom plan view of the lower sensor housing shown in FIGS. 81 through 83;

FIG. 84 is a plan view of a portion of a flex circuit used to electrically interface with a pair of ultrasonic transducers;

FIG. 85 is a partially exploded perspective view showing how the ultrasonic transducers are attached to the flex circuit using conductive transfer tape;

FIG. 86 is a perspective bottom view showing the assembly of FIG. 85 installed in the upper sensor housing;

FIG. 87 is a perspective bottom view showing a miniature circuit board installed on the flex circuit of the assembly of FIG. 86;

FIG. 88 is a front plan view of an optical sensor module;

FIG. 89 is a side view of the optical sensor module shown in FIG. 88;

FIG. 90 is top view of the optical sensor module shown in FIGS. 88 and 89;

FIG. 91 is a side plan view of a valve actuator;

FIG. 92 is an side edge view of the valve actuator shown in FIG. 91;

FIG. 93 is a bottom view of the valve actuator shown in FIGS. 91 and 92;

FIG. 94 is a top view of one of the actuator guides used to guide and retain in position the valve actuators for one cassette;

FIG. 95 is a side view of the actuator guide shown in FIG. 94;

FIG. 96 is a top plan view of a pressure transducer;

FIG. 97 is a side view of the pressure transducer shown in FIG. 96;

FIG. 98 is a bottom view of the pressure transducer shown in FIGS. 96 and 97;

FIG. 99 is a bottom plan view of the elastomeric valve actuator seal used to bias the valve actuators in an upward position;

FIG. 100 is a cutaway view of the valve actuator seal shown in FIG. 99;

FIG. 101 is a perspective view of the main pump unit chassis having the various components for one pump mounted thereon;

FIG. 102 is a bottom view of the main pump unit chassis having the various components for one pump mounted thereon, with the slide lock in the open position ready to receive a cassette;

FIG. 103 is a bottom view of the main pump unit chassis shown in FIG. 102, with the slide lock in the closed position as it would be if a cassette were installed and latched onto the main pump unit;

FIG. 104 is a side view illustrating a cassette in position to be installed on the main pump unit;

FIG. 105 is a side view illustrating the cassette as it is engaging the main pump unit, showing the tubing adapter engaging the flared recess in the bottom of the sensor housing to draw the outlet tube into engagement between the ultrasonic transducers;

FIG. 106 is a side view illustrating the cassette fully installed on the main pump unit with the slide latch closed and the outlet tube in full engagement between the ultrasonic transducers in the sensor housing;

DETAILED DESCRIPTION OF THE PREFERRED EMBODIMENT

The Cassette

Figure 1:
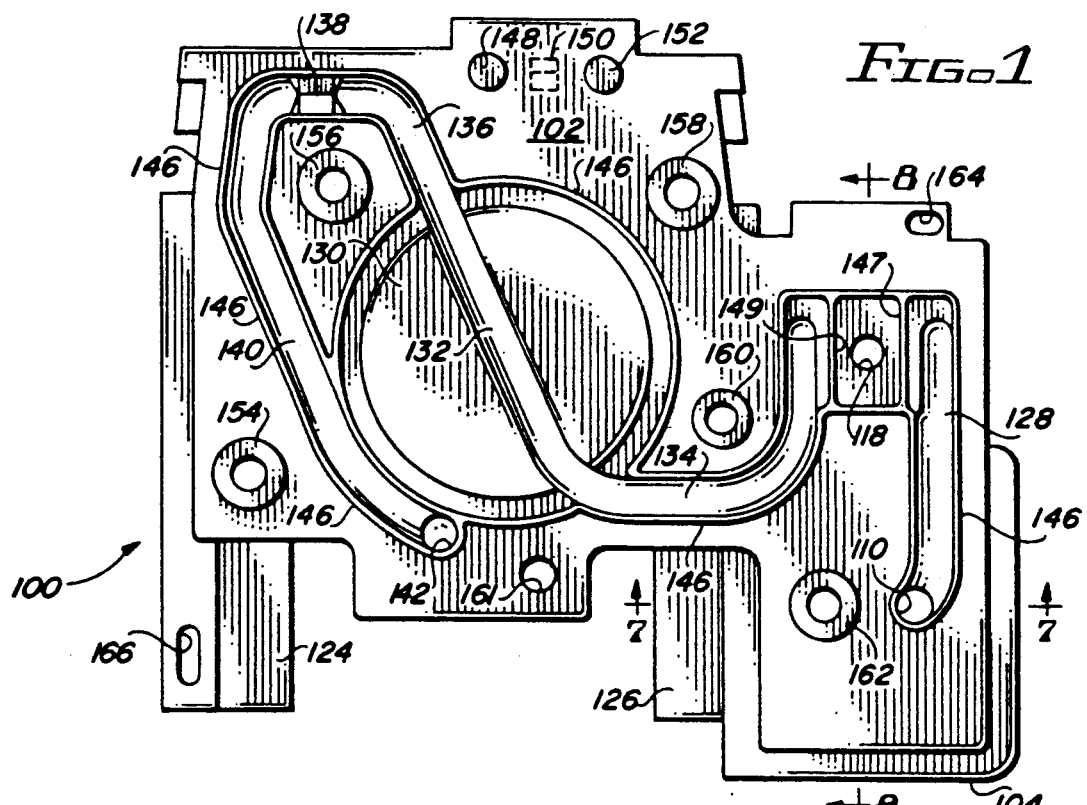
FIG. 1 is a top plan view of a disposable cassette body showing most of the fluid path through the cassette.
Figure 2:
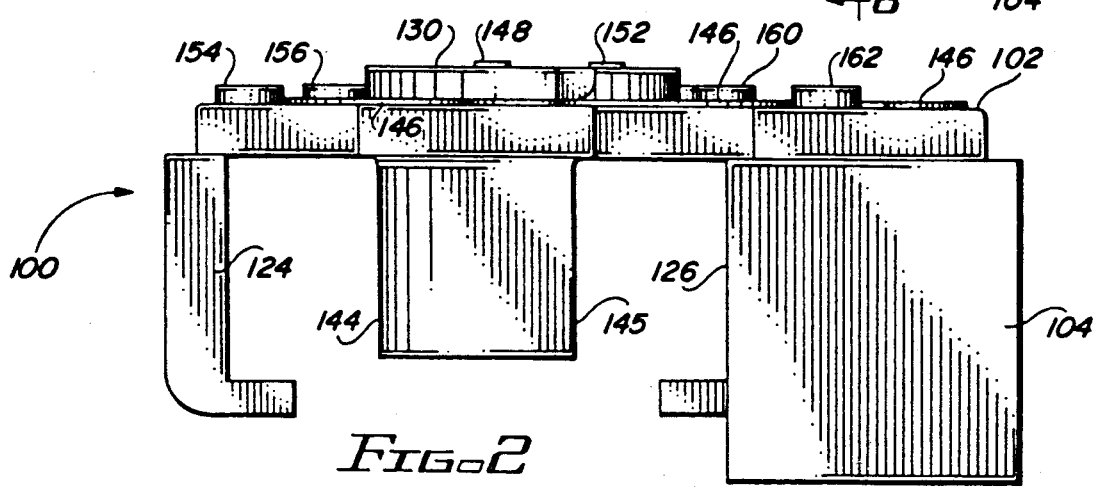
FIG. 2 is a front side view of the cassette body shown in FIG. 1.

The preferred embodiment of the cassette using the air-in-line detector of the present invention includes all of the features described above in a single compact disposable cassette constructed of seven parts. Prior to a discussion of the construction and operation of the cassette, the basic construction of which is the subject of the above-identified patent application entitled "Disposable Cassette for a Medication Infusion System," it is advantageous to discuss the construction and configuration of the seven components included in the cassette. The first of these components and the one around which the other six components are assembled is a cassette body 100, which is shown in FIGS. 1 through 8. The cassette body 100 has an upper surface portion 102 which is essentially flat with a number of protrusions and indentations located in the top surface thereof (FIG. 1). The upper surface portion 102 has a thickness sufficient to accommodate the indentations mentioned above, some of which are fluid passageways which will be discussed below.

Referring generally to FIGS. 1 through 8, a bubble trap 104 is located at the front right corner of the cassette body 100 below the upper surface portion 102, which bubble trap 104 is essentially square in cross-section (FIG. 4). The bubble trap 104 includes therein a bubble chamber 106 which is open at the bottom thereof (FIGS. 4, 7, and 8) and closed at the top by the bottom of the upper surface portion 102 of the cassette body 100. A siphon tube 108 is located in the bubble chamber 106, and the siphon tube 108 has an aperture 110 therein leading from the bottom of the bubble chamber 106 to the top of the upper surface portion 102 of the cassette body 100.

Located behind the bubble trap 104 below the upper surface portion 102 of the cassette body 100 on the right side thereof is a pump cylinder 112 (FIGS. 3-5, 8). The pump cylinder 112 does not extend downward as far as does the bubble trap 104. The pump cylinder 112 is open on the bottom thereof, and is arranged and configured to receive a piston which will be discussed below. The inner configuration of the pump cylinder 112 has a main diameter bore 114, with a greater diameter bore 116 near the bottom of the pump cylinder 112. The interior of the bottom of the pump cylinder 112 below the greater diameter bore 116 as well as the area immediately between the greater diameter bore 116 and the main diameter bore 114 ar tapered to facilitate entry of the piston. The main diameter bore 114 terminates at the top thereof in a frustroconical smaller diameter aperture 118 leading to the top of the upper surface portion 102 of the cassette body 100 (FIG. 1). The smaller diameter aperture 118 is tapered, having a smaller diameter at the top thereof than at the bottom.

Extending from on the back side of the exterior of the bubble trap 104 facing the pump cylinder 112 are two piston retaining fingers 120 and 122 (FIGS. 3 and 4) defining slots therein. The slots defined by the two piston retaining fingers 120 and 122 face each other, and are open at the bottoms thereof to accept in a sliding fashion a flat segment fitting between the two piston retaining fingers 120 and 122. The two piston retaining fingers 120 and 122 extend from the lower surface of the upper surface portion 102 of the cassette body 100 to a location between the bottom of the pump cylinder 112 and the bottom of the bubble trap 104.

Also extending from the bottom side of the upper surface portion 102 of the cassette body 100 are two latch supporting fingers 124 and 126 (FIGS. 1-4 and 7). The latch supporting finger 124 extends downwardly from the left side of the bottom of the upper surface portion 102 of the cassette body 100, and at the bottom extends toward the right slightly to form an L-shape in cross section. The latch supporting finger 124 extends toward the front of the cassette body 100 further than does the upper surface portion 102 of the cassette body 100 (FIG. 1), and terminates approximately two-thirds of the toward the back of the upper surface portion 102 of the cassette body 100.

The latch supporting finger 126 extends downwardly from the bottom of the upper surface portion 102 of the cassette body 100 at with the left side of the bubble trap 104 forming a portion of the latch supporting finger 126. The latch supporting finger 126 extends toward the left slightly at the bottom thereof to form a backwards L-shape in cross section. The latch supporting finger 126 parallels the latch supporting finger 124, and is equally deep (FIG. 4). The latch supporting fingers 124 and 126 together will hold the slide latch, to be described below.

The passageways located in the top of the upper surface portion 10 of the cassette body 100 may now be described with primary reference to FIG. 1. The passageways in the top of the upper surface portion 102 are all open on the top side of the upper surface portion 102, and are generally U-shaped as they are recessed into the top of the upper surface portion 102. A first passageway 128 communicates with the aperture 110 in the siphon tube 108 of the bubble trap 104 at one end thereof, and extends toward the back of the upper surface portion 102 of the cassette body 100 to a location to the right of the smaller diameter aperture 118 of the pump cylinder 112.

A cylindrical pressure plateau 130 which is essentially circular as viewed from the top extends above the upper surface portion 102 of the cassette body 100 slightly left of the center thereof (best shown in FIGS.

1 through 3, also shown in FIGS. 5 through 8). The top of the pressure plateau 130 is flat, with a channel 132 extending across the flat top of the pressure plateau 130. The channel 132 extends from five o'clock to eleven o'clock as viewed from the top in FIG. 1, with the back of the cassette body 100 being twelve o'clock. The channel 132 is also shown in cross-section in FIG. 115, and in a cutaway view in FIG. 116. The depth of the channel 132 in the surface of the pressure plateau 130 is not quite the height of the pressure plateau 130 above the upper surface portion 102 of the cassette body 100, with the channel 132 gradually becoming deeper with a smooth transition at the edges of the pressure plateau 130 to extend into the upper surface portion 102 of the cassette body 100 (FIG. 116).

A second passageway 134 in the top of the upper surface portion 102 of the cassette body 100 begins at a location to the left of the smaller diameter aperture 118 of the pump cylinder 112, and extends toward the front of the upper surface portion 102 approximately above the latch supporting finger 126. The second passageway 134 then travels to the left to connect in fluid communication with the end of the channel 132 in the pressure plateau 130 located at five o'clock. A third passageway 136 in the top of the upper surface portion 102 of the cassette body 100 begins at the end of the channel 132 in the pressure plateau 130 located at eleven o'clock, and moves toward the back and left of the cassette body 100.

At the end of the third passageway 136 is a recessed lens portion 138, which recessed lens portion is used to focus and reflect light used to detect air bubbles passing in front of the recessed lens portion 138. The recessed lens portion 138 is also recessed into the top of the upper surface portion 102 of the cassette body 100 to allow fluid to pass therethrough. The recessed lens portion 138 is part of the apparatus which is the subject of the present invention. A fourth passageway 140 in the top of the upper surface portion 102 of the cassette body 100 begins at the other side of the recessed lens portion 138 from the third passageway 136, and extends from the left and back of the cassette body 100 toward the front and right of the cassette body 100 around the pressure plateau 130 to a location at approximately seven o'clock on the pressure plateau 130. It should be noted that the fourth passageway 140 is spaced away from the pressure plateau 130 to allow for sealing means therebetween.

The end of the fourth passageway 140 terminates at the location at seven o'clock to the pressure plateau 130 in an aperture 142 extending through the upper surface portion 102 of the cassette body 100 (FIG. 1). Located underneath the upper surface portion 102 of the cassette body 100 concentrically around the aperture 142 is an the outlet tube mounting cylinder 144 (FIGS. 3 and 4) which is in fluid communication with the aperture 142. The outlet tube mounting cylinder 144 extends downwardly from the bottom of the upper surface portion 102 of the cassette body 100 to a location above the portions of the latch supporting finger 124 and the latch supporting finger 126 extending parallel to the upper surface 102 of the cassette body 100. A support fin 145 extends to the right from the front of the outlet tube mounting cylinder 144.

Located on top of the upper surface 102 of the cassette body 100 is a slightly raised border 146 (FIG. 1) which completely surrounds the first passageway 128, the smaller diameter aperture 118, the second passageway 134, the pressure plateau 130, the third passageway 136, the recessed lens portion 138, the recessed lens portion 138, and the fourth passageway 140. The slightly raised border 146, which is used for sealing purposes, closely surrounds the edges of all of the aforementioned segments of the cassette body 100, except as follows. The slightly raised border 146 is spaced away from the portions of the first passageway 128 and the second passageway 134 adjacent the smaller diameter aperture 118, and the smaller diameter aperture 118.

The portions of the slightly raised border 146 around the smaller diameter aperture 118 resembles a rectangle with its wider sides located to the front and back and spaced away from the valve diaphragm 170, and its narrower sides to the right of the portion of the first passageway 128 adjacent the smaller diameter aperture 118 and to the left of the portion of the second passageway 134 adjacent the smaller diameter aperture 118. The rectangle is broken only at the locations the first passageway 128 and the second passageway 134 extend towards the front of the cassette body 100.

The slightly raised border 146 has a segment 147 located between the portion of the first passageway 128 adjacent the smaller diameter aperture 118 and the smaller diameter aperture 118 itself, with the segment 147 extending between the two wider sides of the rectangle. The slightly raised border 146 also has another segment 149 located between the portion of the second passageway 134 adjacent the smaller diameter aperture 118 and the smaller diameter aperture 118 itself, with the segment 149 extending between the two wider sides of the rectangle. The slightly raised border 146 is also spaced away from the sides of the pressure plateau 130, and the portions of the second passageway 134 and the third passageway 136 immediately adjacent the pressure plateau 130.

Figure 3:
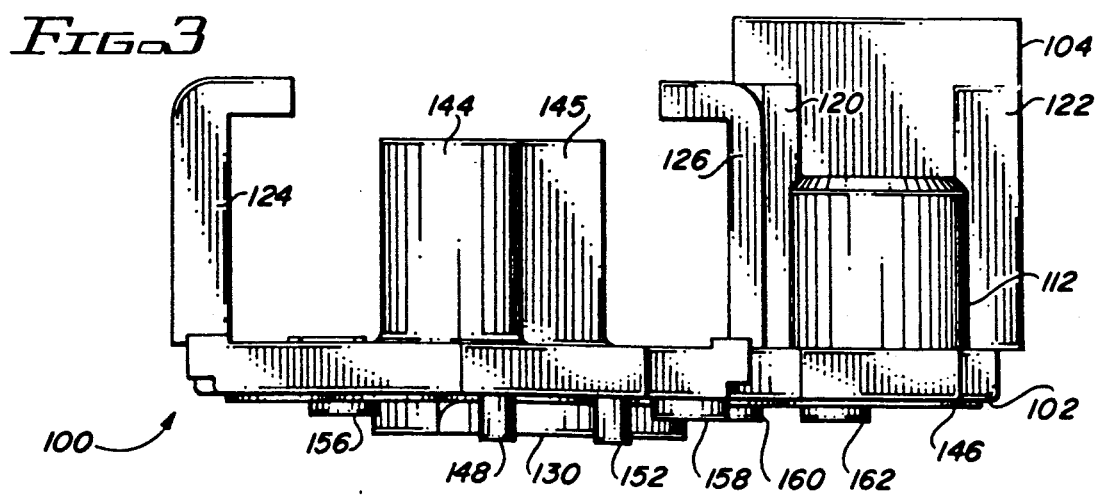
FIG. 3 is a back side view of the cassette body shown in FIGS. 1 and 2.
Figure 33:
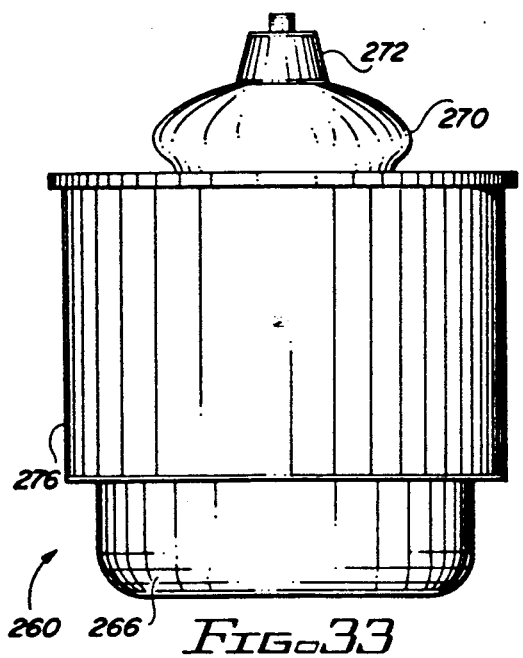
FIG. 33 is a side plan view of the piston cap and boot seal, which function both as a piston and as a bacterial seal.

Located at the back of the upper surface 102 of the cassette body 100 are three cassette identifying indicia 148, 150, and 152. The first and third cassette identifying indicia 148 and 152 are small, solid cylinders extending upward from the top of the upper surface 102 of the cassette body 100 (FIGS. 1 and 3). The second cassette identifying indicia 150 is a prism cut into the bottom of the upper surface 102 of the cassette body 100 (FIG. 4). The first, second, and third cassette identifying indicia 148, 150, and 152 are the subject of the above-identified patent application entitled "Cassette Optical Identification Apparatus for a Medication Infusion System." It will be noted that the cassette identifying indicia 148, 150, and 152 may be in any order or configuration, and are used for different ID codes to identify u to eight different cassettes. Additional ID bits could also be used if more than eight different cassettes are used. If redundant codes are desired, the three bits would of course accommodate the use of less than eight different cassettes.

Completing the construction of the cassette body 100 are five hollow cylinders 154, 156, 158, 160 and 162 protruding from the top surface of the upper surface 102 of the cassette body 100, an aperture 161 and a slot 164 located in the top surface of the upper surface 102 of the cassette body 100, and a slot 166 located in the top surface of the latch supporting finger 124. Four of the hollow cylinders 154, 156, 158, and 160 are located around the pressure plateau 130, with the fifth hollow cylinder 162 being located to the left of the aperture 110 over the bubble trap 104. The aperture 161 is located in the top surface of the upper surface 102 of the cassette body 100 in front and to the right of center of the pressure plateau 130. The slot 164 is located in the top surface of the upper surface 102 of the cassette body 100 near the back and the right side thereof. The slot 166 is located in the top surface of the latch supporting finger 124 near the front of the cassette body 100.

Referring now to FIGS. 9 through 12, a valve diaphragm 170 is shown which is arranged and configured to fit over the top of the upper surface 102 of the cassette body 100 (FIG. 1). The valve diaphragm 170 is made of flexible, resilient material, such as a medical grade silicone rubber. The hardness of the material used for the valve diaphragm 170 would be between thirty and fifty on the Shore A scale, with the preferred embodiment utilizing a hardness of approximately thirty-five. The valve diaphragm 170 has three primary functions, the first of which is to seal the tops of the first, second, third, and fourth passageways 128, 134, 136, and 140, respectively. Accordingly, the main surface of the valve diaphragm 170 is flat, and is sized to fit over the first, second, third, and fourth passageways 128, 134, 136, and 140, respectively, and also over the entire slightly raised border 146. The flat portion of the valve diaphragm 170 has three apertures 172, 174, and 176, and a notch 175 therein to accommodate the hollow cylinders 156, 160, and 162 and a pin fitting into the aperture 161 (FIG. 1), respectively, and to align the valve diaphragm 170 in position over the top of the upper surface 102 of the cassette body 100. It should be noted that the valve diaphragm 170 does not necessarily surround the other two hollow cylinders 154 and 158.

The second primary function of the valve diaphragm 170 is to provide both an inlet valve between the first passageway 128 and the smaller diameter aperture 118 leading to the pump cylinder 112, and to provide an outlet valve between the smaller diameter aperture 118 leading to the pump cylinder 112 and the second passageway 134. To fulfill this function the valve diaphragm 170 has an essentially rectangular domed portion 178 (shown in plan view in FIGS. 9 and 10, and in cross-sectional views in FIGS. 11 and 12) forming a cavity 180 in the bottom of the valve diaphragm 170. When the valve diaphragm 170 is installed in position on the top of the upper surface 102 of the cassette body 100, the cavity 180 will be located just inside the rectangular portion of the slightly raised border 146 around the smaller diameter aperture 118 leading to the pump cylinder 112 (FIG. 1).

The cavity 18 will therefore be in fluid communication with the first passageway 128, the smaller diameter aperture 118 leading to the pump cylinder 112, and the second passageway 134. Prior to installation of the cassette onto the main pump unit, the cavity 180 allows the open fluid path to facilitate priming of the cassette, where all air is removed from the system. Once primed, the cassette may be inserted onto the main pump unit and the cavity 180 will contact valve actuators to prevent free flow through the cassette. By using an inlet valve actuator to force the domed portion 178 over the segment 147 of the slightly raised border 146 (FIG. 1), the flow of fluids between the first passageway 128 and the smaller diameter aperture 118 will be blocked, but the flow of fluids between the smaller diameter aperture 118 and the second passageway 134 will be unaffected. Likewise, by using an outlet valve actuator to force the domed portion 178 over the segment 149 of the slightly raised border 146 (FIG. 1), the flow of fluids between the smaller diameter aperture 118 and the second passageway 134 will be blocked, but the flow of fluids between the first passageway 128 and the smaller diameter aperture 118 will be unaffected. Extending around and spaced away from the front and sides of the domed portion 178 on the top surface of the valve diaphragm 170 is a U-shaped raised rib 181, the legs of which extend to the back of the valve diaphragm 170 (FIG. 9).

The third primary function of the valve diaphragm 170 is to provide a pressure diaphragm which may be used to monitor outlet fluid pressure. Accordingly, the valve diaphragm 170 has a pressure diaphragm 182 which is supported atop an upper cylindrical segment 184, which in turn is located atop a lower cylindrical segment 186 extending above the surface of the valve diaphragm 170. The upper cylindrical segment 184 and the lower cylindrical segment 186 have identical inner diameters, with a lower cylindrical segment 186 having a greater outer diameter than the upper cylindrical segment 184. A portion of the top of the lower cylindrical segment 186 extends outwardly around the bottom of the upper cylindrical segment 184, creating a lip 188. In the preferred embodiment, the pressure diaphragm 182 may be domed slightly, as seen in FIG. 11.

Turning now to FIGS. 13 through 23, a retainer Cap 190 is shown which fits over the valve diaphragm 170 after it is mounted on the top of the upper surface 102 of the cassette body 100. The retainer cap 190 thus functions to cover the top of the cassette body 100, retaining the valve diaphragm 170 between the retainer cap 190 and the cassette body 100 in a sealing fashion. The retainer cap 190 thus has the same general outline when viewed from the top (FIG. 13) as the cassette body 100 (FIG. 1). Located in the bottom of the retainer cap 190 (FIG. 14) are six pins 192, 194, 196, 198, 200, and 199, which are to be received by the hollow cylinders 154, 156, 158, 160, and 162 and the aperture 161, respectively, in the cassette body 100 to align the retainer cap 190 on the cassette body 100. Also located in the bottom of the retainer cap 190 is a tab 202 to be received by the slot 164, and a tab 204 to be received by the slot 166.

The retainer cap 190 has three apertures 206, 208, and 210 therethrough located to coincide with the locations of the first cassette identifying indicia 148, the second cassette identifying indicia 150, and the third cassette identifying indicia 152, respectively. The size of the three apertures 206, 208, and 210 is sufficient to receive the small, solid cylinders which the first cassette identifying indicia 148 and the third cassette identifying indicia 152 comprise.

Located in the retainer cap 190 is a rectangular aperture 212 (FIGS. 13, 14, 19 and 20) for placement over the domed portion 178 on the valve diaphragm 170. The rectangular aperture 212 in the retainer cap 190 is slightly larger than the domed portion 178 on the valve diaphragm 170 to prevent any closure of the cavity 180 formed by the domed portion 178 when the retainer cap 190 is placed over the valve diaphragm 170 and the cassette body 100. The domed portion 178 of the valve diaphragm 170 therefore will protrude through the rectangular aperture 212 in the retainer cap 190. In the bottom of the retainer cap 190 around the rectangular aperture 212 is a U-shaped groove 214 (FIG. 14) designed to accommodate the U-shaped raised rib 181 on the valve diaphragm 170.

Also located in the retainer cap 190 is a circular aperture 216 (FIGS. 13 and 14), which has a diameter slightly larger than the outer diameter of the upper cylindrical segment 184 on the valve diaphragm 170, to allow the upper cylindrical segment 184 and the pressure diaphragm 182 to protrude from the circular aperture 216 in the retainer cap 190. The diameter of the circular aperture 216 is smaller than the outer diameter of the lower cylindrical segment 186 on 170, and on the bottom of the retainer cap 190 is disposed concentrically around the circular aperture 216 a cylindrical recess 218 to receive the lower cylindrical segment 186 on the valve diaphragm 170. Disposed in the cylindrical recess 218 on the bottom side of the retainer cap 190 is a circular raised bead 220 (FIGS. 14, 19, and 21) to help in the sealing of the cassette as it is assembled.

The retainer cap 190 has a front edge 222 (FIG. 16), a back edge 224 (FIG. 15), and left (FIG. 18) and right (FIG. 17) side edges 226 and 228, respectively. The edges 222, 224, 226, and 228 will contact the top of the upper surface 102 of the cassette body 100 when the retainer ca 190 is assembled onto the cassette body 100 with the valve diaphragm 170 disposed therebetween. The retainer cap 190 is attached to the cassette body 100 in the preferred embodiment by ultrasonic welding, but adhesives or other bonding techniques known in the art may also be used.

Referring next to FIGS. 22 through 26, a bubble chamber cap 230 is illustrated which is for placement onto the open bottom of the bubble trap 104 (FIG. 4). The bubble chamber cap 230 is on the bottom (FIG. 23) the same size as the outer edges of the bottom of the bubble trap 104 (FIG. 4), and has a tab 232 (FIGS. 22 through 24) on the bottom which will project toward the back of the cassette beyond the back edge of the bubble trap 104. The bubble chamber cap 230 has a rectangular wall portion 234 (FIG. 24) extending upward from the bottom of the bubble chamber cap 230 and defining therein a square space, which rectangular wall portion 234 is sized to fit inside the bubble chamber 106 (FIG. 4).

Located at the front and left sides of the rectangular wall portion 234 and extending upwards from the bottom of the bubble chamber cap 230 is an inlet cylinder 236 (FIGS. 22, 24, and 26) having an inlet aperture 238 extending therethrough. The inlet aperture 238 extends through the bottom of the bubble chamber cap 230 (FIGS. 23 and 25), and is designed to receive from the bottom of the bubble chamber cap 230 a length of tubing therein. The bubble chamber cap 230 is attached to the bottom of the bubble trap 104 in the cassette body 100 in the preferred embodiment by ultrasonic welding, but adhesives or other bonding techniques known in the art may also be used.

When the bubble chamber cap 230 is mounted to the bubble trap 104, the inlet cylinder 236 extends up to at least half of the height of the bubble chamber 106 (FIG. 7), and the siphon tube 108 (FIG. 7) draws fluid from the bottom of the siphon tube 108 in the space within the rectangular wall portion 234 of the bubble chamber cap 230 (FIG. 26). It will be appreciated by those skilled in the art that fluid will enter the bubble chamber 106 through the inlet aperture 238 in the inlet cylinder 236 near the top of the siphon tube 108, maintaining all air bubbles above the level near the bottom of the bubble chamber 106 at which fluid is drawn from the bubble chamber 106 by the siphon tube 108.

Moving now to FIGS. 27 through 32, a slide latch 240 is disclosed which served two main functions in the cassette. The slide latch 240 first serves to latch the cassette into place in a main pump unit. It also serves to block the flow of fluid through the cassette when it is not installed, with the closing of the slide latch 240 to lock the cassette into place on the main pump unit also simultaneously allowing the flow of fluid through the cassette. The slide latch 240 slides from the front of the cassette body 100 (FIG. 2) between the latch supporting finger 124 and the latch supporting finger 126.

The slide latch 240 has an essentially rectangular, flat front portion 242 (FIG. 31) which is of a height equal to the height of the cassette body 100 with the retainer cap 190 and the bubble chamber cap 230 installed, and a width equal to the distance between the left side of the bubble trap 104 and the left side of the cassette body 100. Two small notches 244 and 246 are removed from the back side of the front portion 242 at the top thereof (FIGS. 27, 28, and 30), the small notch 244 being removed at a location near the left corner, and the small notch 246 being removed at the right corner.

Extending from the back side of the front portion 242 about three-quarters of the way down towards the back is a horizontal bottom portion 248 (FIG. 29), which has its edges directly below the closest edges of the small notch 244 and the small notch 246. Extending from the inner edge of the small notch 244 at the top of the slide latch 240 down to the bottom portion 248 is an inverted angled or L-shaped portion 250. Similarly, extending from the inner edge of the small notch 246 at the top of the slide latch 240 down to the bottom portion 248 is an inverted, backwards angled or L-shaped portion 252 (FIGS. 27 and 28).

Spaced outwardly from the left side of the bottom portion 248 and the left side of the leg of the inverted L-shaped portion 250 is a left slide side 254. Likewise, spaced outwardly from the right side of the bottom portion 248 and the right side of the leg of the inverted, backwards L-shaped portion 252 is a right slide side 256 (FIGS. 28 and 30). The left and right slide sides 254 and 256 are located slightly above the bottom of the bottom portion 248 (FIG. 30). The left and right slide sides 254 and 256 are of a height to be engaged in the latch supporting finger 124 and the latch supporting finger 126 (FIG. 2), respectively.

Located in the bottom portion 248 is an elongated, tear-shaped aperture 258 (FIG. 29), with the wider portion thereof toward the front of the slide latch 240 and the extended narrower portion thereof toward the back of the slide latch 240. When the slide latch 240 is inserted into the latch supporting finger 124 and the latch supporting finger 126 on the cassette body 100, and the slide latch 240 is pushed fully toward the back of the cassette body 100, the wider portion of the elongated, tear-shaped aperture 258 will be aligned with the aperture 142 in the outlet tube mounting cylinder 144 (FIG. 4) to allow a segment of tubing (not shown) leading from the aperture 142 to be open. When the slide latch 240 is pulled out from the front of the cassette body 100, the segment of tubing (not shown) will be pinched off by the narrower portion of the elongated, tear-shaped aperture 258.

It is critical that the design and location of the elongated, tear-shaped aperture 258 in the slide latch 240 ensure that the slide latch 240 engages the main pump unit before the tubing is opened up, and fluid is allowed to flow through the cassette. Likewise, the tubing must be pinched off and the fluid path through the cassette must be blocked before the slide latch 240 releases the cassette from the main pump unit. In addition, the choice of material for the slide latch 240 is important, with a lubricated material allowing the pinching operation to occur without damaging the tubing (not shown). Examples of such materials are silicone or Teflon impregnated acetals such as Delrin.

Located at the back of the slide latch 240 on the inside of the right slide side 256 at the bottom thereof is a tab 257 (FIGS. 27, 30, and 32) which is used to engage the main pump unit with the cassette when the slide is closed. Located on the top side of the bottom portion 248 to the right of the elongated, tear-shaped aperture 258 is a small wedge-shaped retaining tab 259 (FIG. 27, 30, and 32). The retaining tab 259 cooperates with the bottom of the slightly raised border 146 of the cassette body 100 (FIG. 2), to resist the slide latch 240 from being freely removed once installed into the cassette body 100. When the slide latch 240 is pulled back out from the front of the cassette body 100 so that the wider portion of the elongated, tear-shaped aperture 258 is aligned with the aperture 142 in the outlet tube mounting cylinder 144, the retaining tab 259 will engage the slightly raised border 146 (FIGS. 2 and 4), resisting the slide latch 240 from being drawn further out.

Referring now to FIGS. 33 through 36, a one-piece piston cap and boot seal 260 is illustrated, which is the subject of the above-identified patent application entitled "Piston Cap and Boot Seal for a Medication Infusion System," and which is for use on and in the pump cylinder 112 (FIGS. 3 and 8). The piston cap and boot seal 260 is of one-piece construction, and is made of flexible, resilient material, such as silastic (silicone rubber) or medical grade natural rubber. Natural rubber may be used to minimize friction, since some sticking of a silicone rubber piston cap and boot seal 260 in the pump cylinder 112 (FIG. 8) may occur. Teflon impregnated silastic or other proprietary formulas widely available will overcome this problem. In addition, the piston cap and boot seal 260 may be lubricated with silicone oil prior to installation in the pump cylinder 112. The advantage of using silastic is that it may be radiation sterilized, whereas natural rubber must be sterilized using gas such as ethylene oxide. In addition, silastic has better wear characteristics than natural rubber, making it the preferred choice.

The piston cap and boot seal 260 includes a piston cap portion indicated generally at 262, and a boot seal portion comprising a retaining skirt 264 and a thin rolling seal 266. The piston cap portion 262 includes a hollow cylindrical segment 268 having an enlarged, rounded piston cap head 270 located at the top thereof. The piston cap head 270 has a roughly elliptical cross-section, with an outer diameter on the sides sufficient to provide a dynamic seal in the main diameter bore 114 of the pump cylinder 112 (FIG. 8). The roughly elliptical configuration of the piston cap head 270 closely fits the top of the main diameter bore 114 of the pump cylinder 112. Extending from the top of the piston cap head 270 at the center thereof is a frustroconical segment 272, with the larger diameter of the frustroconical segment 272 being at the bottom thereof attached to the piston cap head 270. The frustroconical segment 272 is of a size to closely fit in the smaller diameter aperture 118 of the pump cylinder 112 (FIG. 8).

The hollow cylindrical segment 268 and the piston cap head 270 together define a closed end of the piston cap and boot seal 260 to receive a piston, which will be described below. The hollow cylindrical segment 268 has located therein a smaller diameter portion 274, which smaller diameter portion 274 is spaced away from the bottom of the piston cap head 270 to provide retaining means to retain a piston in the hollow cylindrical segment 268 between the piston cap head 270 and the smaller diameter portion 274.

The retaining skirt 264 is essentially cylindrical, and is designed to fit snugly around the outer diameter of the pump cylinder 112 (FIG. 8). Prior to installation and with the piston cap and boot seal 260 in a relaxed configuration as shown in FIGS. 33 through 36, the retaining skirt 264 is located roughly around the hollow cylindrical segment 268. The retaining skirt 264 has an internal diameter sufficiently small to retain the retaining skirt 264 in position around the pump cylinder 112 (FIG. 8) without moving when the piston cap portion 262 moves.

Located around the inner diameter of the retaining skirt 26 is a tortuous path 276 leading from on end of the retaining skirt 264 to the other. The tortuous path 276 is required for sterilization of the assembled cassette, to allow the sterilizing gas to sterilize the area between the inside of the pump cylinder 112 and the piston cap and boot seal 260, which would be closed and may remain unsterilized if the tortuous path 276 did not exist. In addition, since the sterilizing gas is hot and cooling occurs rapidly after the sterilizing operation, the tortuous path 276 allows pressure equalization to occur rapidly where it otherwise would not. In the preferred embodiment, the tortuous path 276 is a series of threads in the inner diameter of the retaining skirt 264.

Completing the construction of the piston cap and boot seal 260 is the rolling seal 266, which is a segment defined by rotating around the centerline of the piston cap and boot seal 260 a U having a first leg at the radius of the hollow cylindrical segment 268 and a second leg at the radius of the retaining skirt 264, with the top of the first leg of the U being attached to the bottom of the hollow cylindrical segment 268 and the top of the second leg of the U being attached to the bottom of the retaining skirt 264. When the piston cap and boot seal 260 is installed and the piston cap portion 262 moves in and out in the main diameter bore 114 in the pump cylinder 112 (FIG. 8), the legs of the U will vary in length, with one leg becoming shorter as the other leg becomes longer. In this manner, the rolling seal 266 provides exactly what its name implies—a seal between the piston cap portion 262 and the retaining skirt 264 which rolls as the piston cap portion 262 moves.

Referring now to FIGS. 37 through 42, a piston assembly 280 is shown which drives the piston ca portion 262 of the piston cap and boot seal 260 (FIG. 36) in the pump cylinder 112 (FIG. 8). The piston assembly 280 has a rectangular base 282 which is positioned horizontally and located directly behind the bubble chamber cap 230 (FIG. 24) when the piston cap portion 262 is fully inserted into the pump cylinder 112. The rectangular base 282 has a notch 284 (FIGS. 41 and 42) in the front edge thereof, which notch is slightly larger than the tab 232 in the bubble chamber cap 230 (FIG. 23).

Figure 38:
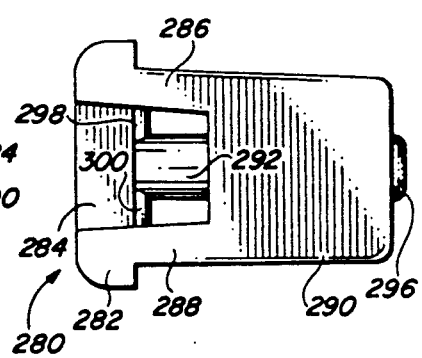
FIG. 38 is a front side view of the piston shown in FIG. 37.

Extending upward from the front edge of the rectangular base 282 on the left side of the notch 284 is an arm 286, and extending upward from the front edge of the rectangular base 282 on the right side of the notch 284 is an arm 288. At the top of the arms 286 and 288 is a vertically extending rectangular portion 290 (FIG. 38). The rectangular portion 290 as well as the upper portions of the arms 286 and 288 are for insertion into and between the piston retaining finger 120 and the piston retaining finger 122 in the cassette body 100 (FIG. 4).

The top of the rectangular portion 290 will contact the bottom of the upper surface 102 of the cassette body 100 (FIG. 8) to limit the upward movement of the piston assembly 280, the rectangular base 282 being approximately even with the bubble chamber cap 230 (FIG. 24) installed in the bottom of the bubble trap 104 of the cassette body 100 when the piston assembly 280 is in its fully upward position. The bottom of the rectangular portion 290 (FIG. 42) will contact the tab 232 on the bubble chamber cap 230 (FIG. 24) when the piston assembly 280, the piston head 296, and the piston cap portion 262 (FIG. 36) are fully retracted from the pump cylinder 112 (FIG. 8).

Figure 36:
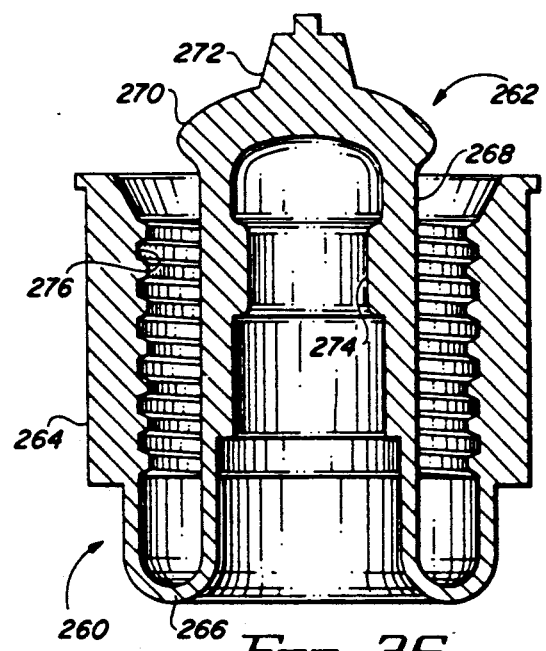
FIG. 36 is a cutaway view from the side of the piston cap and boot seal shown in FIGS. 33 through 35.
Figure 39:
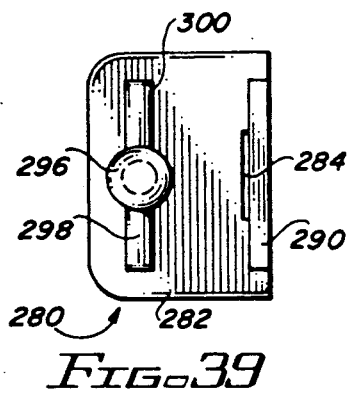
FIG. 39 is a top view of the piston shown in FIGS. 37 and 38.
Figure 40:
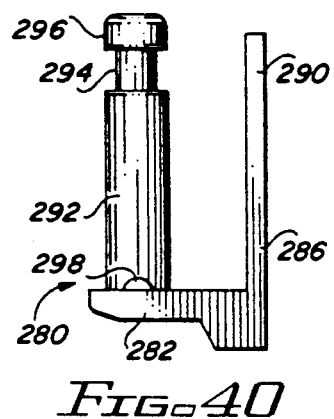
FIG. 40 is a left side view of the piston shown in FIGS. 37 through 39.
Figure 42:
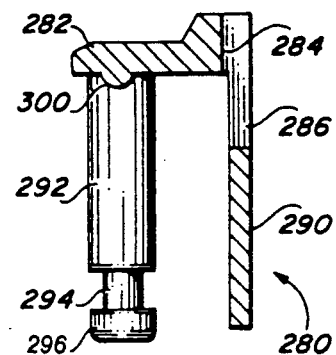
FIG. 42 is a cutaway view from the right side of the piston shown in FIGS. 37 through 41.

Extending upwards from the top of the rectangular base 282 near the back edge of the rectangular base 282 and located centrally with respect to the side edges of the rectangular base 282 is a cylindrical piston rod 292. At the top of the piston rod 292 is a reduced diameter cylindrical portion 294, and mounted on top of the reduced diameter cylindrical portion 294 is a cylindrical piston head 296. The diameter of the piston head 296 is larger than the diameter of the reduced diameter cylindrical portion 294, and the top of the piston head 296 has rounded edges in the preferred embodiment. The piston head 296 is designed to be received in the portion of the hollow cylindrical segment 268 between the smaller diameter portion 274 and the piston cap head 270 in the piston cap portion 262 (FIG. 36). The reduced diameter cylindrical portion 294 is likewise designed to be received in the smaller diameter portion 274 of the piston cap portion 262.

The top of the piston head 296 is slightly above the top of the rectangular portion 290, and when the piston assembly 280 is in its fully upward position, the piston head 296 will have brought the piston cap head 270 and the frustroconical segment 272 thereon (FIG. 36) to the top of the pump cylinder 112 and into the smaller diameter aperture 118 (FIG. 8), respectively, to completely eliminate volume both within the pump cylinder 112 and within the smaller diameter aperture 118.

Completing the construction of the piston assembly 280 are two raised beads 298 and 300, with the raised bead 298 being on the top surface of the rectangular base 282 on the left side of the piston rod 292, and the raised bead 300 being on the top surface of the rectangular base 282 on the right side of the piston rod 292. Both of the raised beads 298 and 300 extend from the sides of the piston rod 292 laterally to the sides of the rectangular base 282. The raised beads 298 and 300 will be used to center the piston assembly 280 with the jaws of the main pump unit used to drive the piston assembly 280, as well as to facilitate retaining the piston assembly 280 in the jaws.

Figure 43:
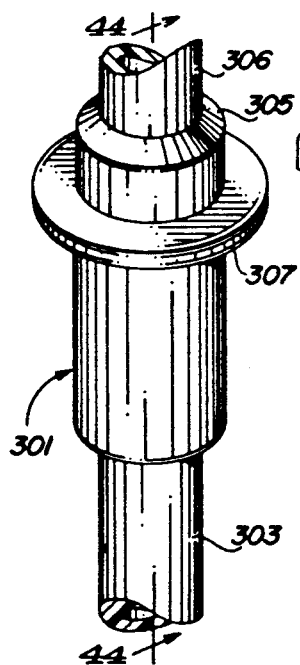
FIG. 43 is a perspective top view of a tubing adapter for installation in the outlet tube below the slide latch.
Figure 45:
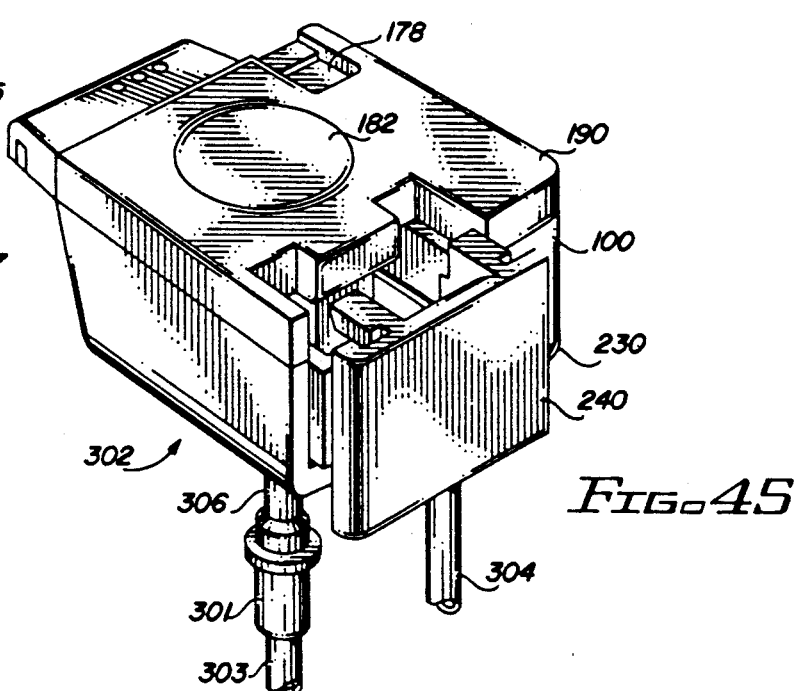
FIG. 45 is a perspective top view of an assembled cassette using the components shown in FIGS. through 44, with the slide latch in the opened position.
Figure 44:
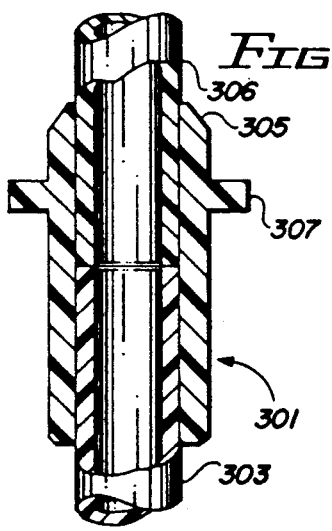
FIG. 44 is a cutaway view of the tubing adapter shown in FIG. 43.

Referring next to FIGS. 43 and 44, a tubing adapter 301 is illustrated which is located between an outlet tubing 306 extending from an assembled cassette 302 and a delivery tubing 303 which leads to the patient. The tubing adapter 301 is essentially cylindrical, and is hollow throughout allowing the inlet tubing 306 and the delivery tubing 303 to be inserted thereinto. The inlet tubing 306 and the delivery tubing 303 are in the preferred embodiment adhesively secured in the tubing adapter 301. Located at the top end of the tubing adapter 301 is a tapered portion 305, with the taper being on the outside of the tubing adapter 301 and having a smaller outer diameter as it approaches the top end of the tubing adapter 301. Located below the tapered portion 305 is a radially outwardly extending flange 307.

The assembly and configuration of the cassette may now be discussed, with reference to an assembled cassette 302 in FIGS. 45 through 48, as well as to other figures specifically mentioned in the discussion. The valve diaphragm 170 is placed over the top of the upper surface 102 of the cassette body 100, with the apertures 172, 174, and 176 placed over the hollow cylinders 156, 160, and 162, respectively. The retainer cap 190 is then located over the valve diaphragm 170 and the cassette body 100, and is secured in place by ultrasonic welding. Note again that while adhesive sealing may be used, it is more difficult to ensure the consistent hermetic seal required in the construction of the cassette 302.

The step of firmly mounting the retainer cap 190 onto the cassette body 100 exerts a bias on the valve diaphragm 170 (FIG. 9) causing it to be compressed in certain areas, particularly over the slightly raised border 146 on the top surface of the upper surface 102 of the cassette body 100 (FIG. 1). This results in excellent sealing characteristics, and encloses the various passageways located in the upper surface 102 of the cassette body 100. The first passageway 128 is enclosed by the valve diaphragm 170, communicating at one end thereof with the aperture 110 and at the other end thereof with the area between the cavity 180 and the upper surface 102 of the cassette body 100. The second passageway 134 also communicates with the area between the cavity 180 and the upper surface 102 of the cassette body 100 at one end thereof, with the other end of the second passageway 134 communicating with one end of the passageway 132 in the pressure plateau 130.

The pressure diaphragm 182 is located above the surface of the pressure plateau 130, and a space exists between the edges at the side of the pressure plateau 130 and the inner diameters of the upper cylindrical segment 184 and the lower cylindrical segment 186. This allows the pressure diaphragm 182 to be quite flexible, a design feature essential to proper operation of the pressure monitoring apparatus. It may therefore be appreciated that the flow area between the second passageway 134 and the third passageway 136 is not just the area of the passageway 132, but also the area between the pressure diaphragm 182 and the pressure plateau 130, as well as the area around the sides of the pressure plateau 130 adjacent the upper cylindrical segment 184 and the lower cylindrical segment 186.

The third passageway 136 (FIG. 1) is also enclosed by the valve diaphragm 170 (FIG. 9), and communicates at one end with the other end of the passageway 132, and at the other end with the recessed lens portion 138. The fourth passageway 140 is enclosed by the valve diaphragm 170, and communicates at one end with the recessed lens portion 138 and at the other end with the aperture 142.

Next, the bubble chamber cap 230 is placed on the bottom of the bubble chamber 106, and is secured by ultrasonically sealing the bubble chamber cap 230 to the cassette body 100. The piston cap portion 262 of the piston cap and boot seal 260 (FIG. 36) is inserted into the main diameter bore 114 of the pump cylinder 112 (FIG. 8), and pushed toward the top of the main diameter bore 114. Simultaneously, the retaining skirt 264 is placed over the outside of the pump cylinder 112 and is moved up the outer surface of the pump cylinder 112 to the position shown in FIGS. 46 and 48, which is nearly to the top of the outer surface of the pump cylinder 112.

Next the piston head 296 of the piston assembly 280 (FIGS. 37 and 40) is inserted into the hollow cylindrical segment 268 of the piston cap and boot seal 260, and is forced past the smaller diameter portion 274 until it snaps home, resting against the bottom of the piston cap head 270.

The slide latch 240 is then inserted into engagement with the cassette body 100, which is accomplished by sliding the left slide side 254 into the latch supporting finger 124 on the right side thereof and by sliding the right slide side 256 into the latch supporting finger 126 on the left side thereof. The slide latch 240 is then pushed fully forward to align the wider portion of the elongated, tear-shaped aperture 258 with the outlet tube mounting cylinder 144. An inlet tube 304 is adhesively secured in the inner diameter of the inlet aperture 23 in the bubble chamber cap 230, in fluid communication with the bubble chamber 106. The outlet tube 306 extends through the wider portion of the elongated, tear-shaped aperture 258 and is adhesively secured in the inner diameter of the outlet tube mounting cylinder 144 in the cassette body 100, in fluid communication with the fourth passageway 140 through the aperture 142.

The tubing adapter 301 is connected to the other end of the outlet tube 306, and the delivery tube 303 is also attached to the tubing adapter 301. The inlet tube 304 and the delivery tube 303 are shown in the figures only in part; on their respective ends not connected to the assembled cassette 302 they may have connector fittings such as standard luer connectors (not shown), which are well known in the art. The use of adhesives to attach the inlet tube 304, the outlet tube 306, and the delivery tube 303 to the assembled cassette 302 and to the tubing adapter 301 also utilizes technology well known in the art. For example, adhesives such as cyclohexanone, methylene dichloride, or tetrahydrofuron (THF) may be utilized.

The Main Pump Unit

Figure 37:
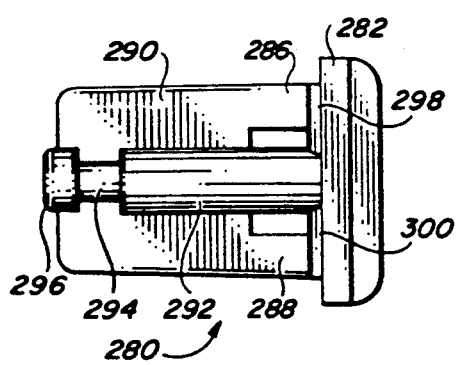
FIG. 37 is a back side plan view of a piston for insertion into the piston cap and boot seal shown in FIGS. 33 through 36.
Figure 41:
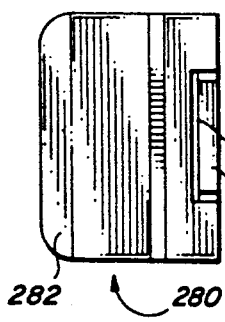
FIG. 41 is a bottom view of the piston shown in FIGS. 37 through 40.

The preferred embodiment of the main pump unit used with the present invention includes a number of components used to hold, latch, and drive the cassette described above. Referring first to FIGS. 49 through 53, a latch head 310 is illustrated which is used to grasp the raised bead 298 and the raised bead 300 of the piston assembly 280 (FIG. 37). Extending from the front of the latch head 310 at the top thereof on the left side is a left jaw 312, and extending from the front of the latch head 310 at the top thereof on the right side is a right jaw 314. The left and right jaws 312 and 314 have curved indentations on the bottom sides thereof to receive the raised bead 298 and the raised bead 300 (FIG. 37), respectively. A space between the left jaw 312 and the right jaw 314 allows them to fit around the piston rod 292 of the piston assembly 280.

A cylindrical aperture 316 is located in the top of the latch head 310, which cylindrical aperture 316 is designed to receive a shaft on which the latch head 310 is mounted. A threaded aperture 318 in the back side of the latch head 310 communicates with the cylindrical aperture 316, and will have locking means installed therein to lock a shaft in the cylindrical aperture 316. An aperture 320 extends through the latch head 310 from the left side to the right side thereof near the back and bottom of the latch head 310.

A notch 322 is located in the latch head 310 at the bottom and front thereof and in the center thereof, leaving a side portion 324 on the left side and a side portion 326 on the right side. An aperture 328 is located through the side portion 324, and an aperture 330 is located through the side portion 326, which apertures 328 and 330 are aligned. In addition, the portion of the latch head 310 including the left jaw 312 has a raised edge 327 facing upward and backward, and a raised edge 329 facing down and forward. The portion of the latch head 310 including the right jaw 314 has a raised edge 331 facing downward and forward. The raised edges 327, 329, and 331 will be used to limit the movement of the latch jaw, which will be discussed below.

A spring seat 332 is shown in FIGS. 54 and 55, which is designed to fit in the notch 322 in the latch head 310 (FIGS. 51 and 53). The spring seat 332 has an aperture 334 extending therethrough from the left side to the right side, which aperture 334 is slightly larger than the apertures 328 and 330 in the latch head 310. The spring seat 332 also has a cylindrical segment 336 extending from the front side thereof.

A latch jaw 340 is illustrated in FIGS. 56 through 58, which latch jaw 340 is used to grasp the bottom of the rectangular base 282 of the piston assembly 280 (FIG. 37) and maintain the left and right jaws 312 and 314 of the latch head 310 (FIG. 51) in contact with the raised bead 298 and the raised bead 300, respectively. The latch jaw 340 has a front jaw portion 342 approximately as wide as the left and right jaws 312 and 314 of the latch head 310, which jaw portion 342 is the portion of the latch jaw 340 which contacts the bottom of the rectangular base 282 of the piston assembly 280. Extending back from the left side of the jaw portion 342 is a left arm 344, and extending back from the right side of the jaw portion 342 is a right arm 346.

The left arm 344 has an aperture 348 (not shown) therethrough from the left side to the right side at the end of the left arm 344 away from the jaw portion 342. Likewise, the right arm 346 has an aperture 350 therethrough from the left side to the right side at the end of the right arm 346 away from the jaw portion 342. The apertures 348 and 350 are slightly smaller in diameter than the aperture 320 in the latch head 310 (FIGS. 49 and 50).

Extending upward from and at an approximately sixty degree angle with respect to the right arm 346 from the end of the right arm 346 away from the jaw portion 342 is a driving arm 352. At the end of the driving arm 352 which is not attached to the right arm 346 is a link pin 354 extending to the right. Completing the construction of the latch jaw 340 is a cylindrical recess 356 located in the back side of the jaw portion 342, which cylindrical recess 356 has an inner diameter larger than the outer diameter of the cylindrical segment 336 of the spring seat 332 (FIG. 55).

Referring now to FIGS. 59 through 61, the construction of a jaws assembly 360 from the latch head 310, the spring seat 332, and the latch jaw 340 is illustrated. The spring seat 332 fits within the notch 322 and between the left jaw 312 and the right jaw 314 of the latch head 310. A pin 362 is inserted through the aperture 328 in the side portion 324, the aperture 334 in the spring seat 332, and the aperture 330 in the side portion 326. The pin 362 is sized to fit snugly in the apertures 328 and 330, thereby retaining the pin 362 in place and allowing the spring seat 332 to rotate about the pin 362.

The latch jaw 340 is mounted onto the latch head 310 with the left jaw 312 and the right jaw 314 of the latch head 310 facing the jaw portion 342 of the latch jaw 340 using a pin 364. The pin 364 is inserted through the aperture 348 (not shown) in the left arm 344, the aperture 320 in the latch head 310, and the aperture 350 in the right arm 346. The pin 364 is sized to fit snugly in the apertures 348 and 350, thereby retaining the pin 364 in place and allowing the latch jaw 340 to rotate about the pin 364.

A spring 366 has one end thereof mounted over the cylindrical segment 336 on the spring seat 332, and the other end thereof mounted in the cylindrical recess 356 in the latch jaw 340. The spring 366 acts to bias the latch jaw 340 in either the open position shown in FIG. 59 with the jaw portion 342 of 340 away from the left jaw 312 and the left jaw 312 of the latch head 310, or in the closed position shown in FIG. 61, with the jaw portion 342 of the latch jaw 340 urged closely adjacent the left jaw 312 and the right jaw 314 of the latch head 310. The movement of the latch jaw 340 in both directions with respect to the latch head 310 is limited, to the position shown in FIG. 59 by the driving arm 352 contacting the raised edge 327, and to the position shown in FIG. 61 by the right arm 346 contacting the raised edge 329 and by the left arm 344 contacting the raised edge 331. When the assembled cassette 302 is installed, movement of the latch jaw 340 to the position of FIG. 61 will also be limited by the presence of the piston assembly 280, with the rectangular base 282 being grasped by the jaws assembly 360. It will be noted that by moving the pin 354 either toward the front or toward the back, the latch jaw 340 may either be opened or closed, respectively.

Referring next to FIGS. 62 through 65, a main pump unit chassis 370 is illustrated which is designed to mount three independent pump units including three drive mechanisms into which three disposable assembled cassettes 302 may be installed. The assembled cassettes 302 are mounted on the bottom side of the pump chassis 370 shown in FIG. 62, with the motors and drive train being mounted on top of the pump chassis 370 (FIG. 64) and being installed in a housing (not shown) mounted on top of the pump chassis 370.

Located on the pump chassis 370 are three pairs of angled segments 372 and 374, 376 and 378, and 380 and 382. Each pair of angled segments 372 and 374, 376 and 378, and 380 and 382 defines two facing channels therebetween. In the preferred embodiment, the angled segments 372 and 374, 376 and 378, and 380 and 382 are angled slightly further from the bottom of the pump chassis 370 near the front, to thereby have a camming effect as the assembled cassette 302 is installed and the slide latch 240 is closed. Specifically, the angled segment 372 defines a channel facing the angled segment 374, and the angled segment 374 defines a channel facing the angled segment 372. The angled segment 376 defines a channel facing the angled segment 378, and the angled segment 378 defines a channel facing the angled segment 376. Finally, the angled segment 380 defines a channel facing the angled segment 382, and the angled segment 382 defines a channel facing the angled segment 380.

Each of the pairs of angled segments 372 and 374, 376 and 378, and 380 and 382 provides means on the bottom of pump chassis 370 for one assembled cassette 302 to be securely latched to. The inverted L-shaped portion 250 and the inverted, backwards L-shaped portion 252 in the slide latch 240 (FIGS. 29 and 30) of the assembled cassette 302 are designed to facilitate attachment to one of the pairs of angled segments 372 and 374, 376 and 378, and 380 and 382. With the slide latch 240 pulled back away from the front of the assembled cassette 302, an area between the front portion 242 of the slide latch 240 and the top front of the cassette body 100 and the retainer cap 190 is open, allowing the top of the assembled cassette 302 to be placed over one of the pairs of angled segments 372 and 374, 376 and 378, and 380 and 382.

Figure 62:
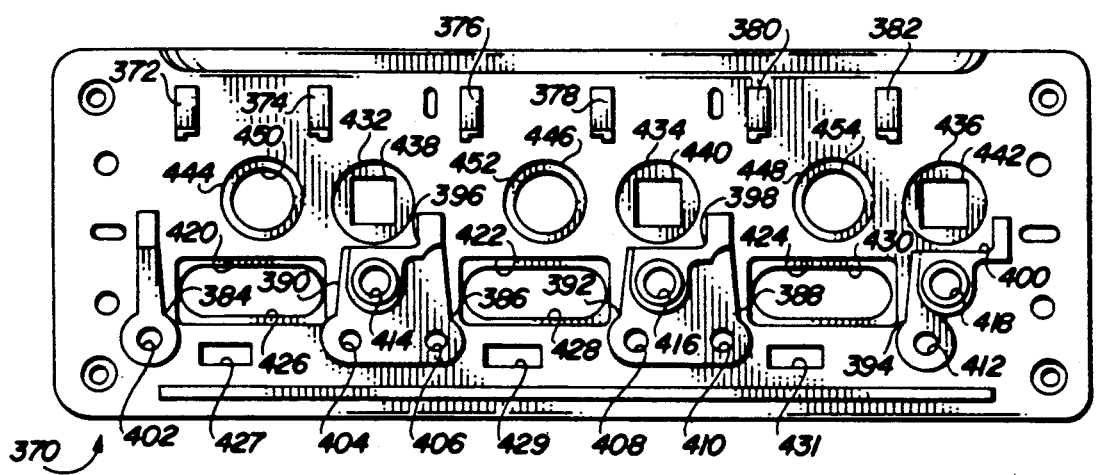
FIG. 62 is a bottom plan view of the main pump unit chassis.
Figure 63:
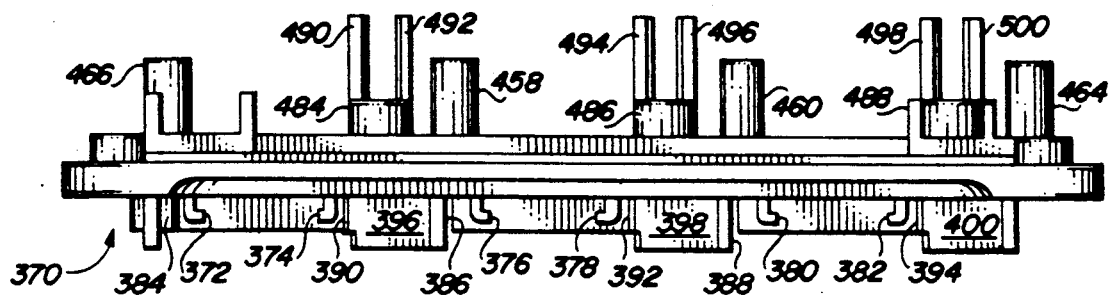
FIG. 63 is a front view of the main pump unit chassis shown in FIG. 62.
Figure 64:
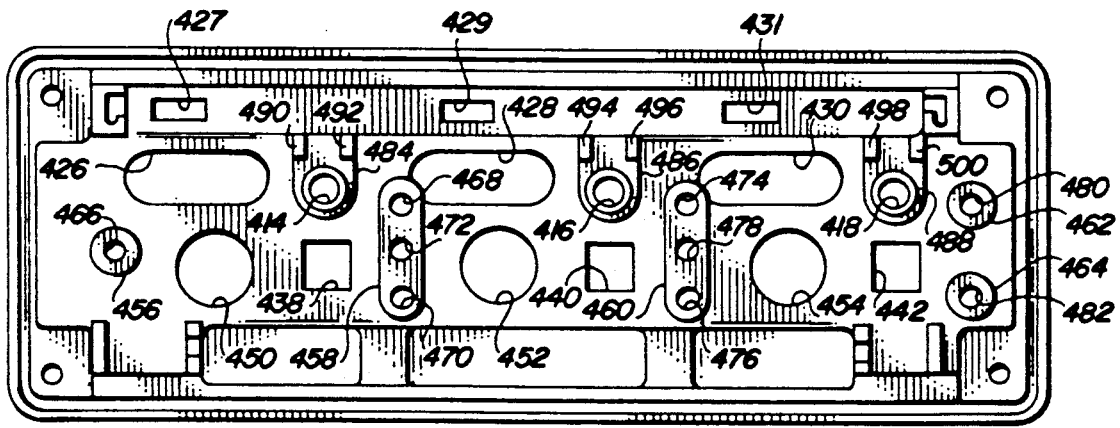
FIG. 64 is a top view of the main pump unit chassis shown in FIGS. 62 and 63.
Figure 65:
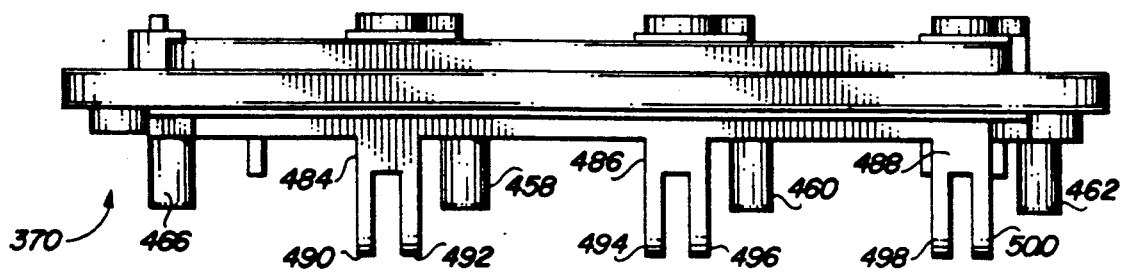
FIG. 65 is a back view of the main pump unit chassis shown in FIGS. 62 through 64.

By way of example, assume that the assembled cassette 302 is to be mounted in the first position (the position on the left end of the pump chassis 370) on the first pair of angled segments 372 and 374. The top surface of the assembled cassette 302, which is the retainer cap 190 (FIG. 43), will mount against the bottom of the pump chassis 370 (FIG. 62). In order to place the assembled cassette 302 in condition to be installed, the slide latch 240 is pulled back fully from the front of the assembled cassette 302, leaving an area between the front portion 242 of the slide latch 240 and the front top portion of the assembled cassette 302 (made up of the cassette body 100 and the retainer cap 190) facing the front portion 242 of the slide latch 240.

The top of the assembled cassette 302 is then placed against the bottom of the pump chassis 370 with the first pair of angled segments 372 and 374 fitting in the are between the front portion 242 of the slide latch 240 and the front top portion of the assembled cassette 302. The slide latch 240 is then pushed forward into the cassette body 100, sliding the inverted L-shaped portion 250 of the slide latch 240 into engagement with the angled segment 372, and sliding the inverted, backwards L-shaped portion 252 of the slide latch 240 into engagement with the angled segment 374. The assembled cassette 302 will thus be held in position on the bottom of the pump chassis 370 until the slide latch 240 is again pulled back, releasing the assembled cassette 302.

Projecting from the bottom of the pump chassis 370 are a number of segments used to position and align the assembled cassettes 302 in the first (the position on the left end of the pump chassis 370), second (intermediate), and third (the position on the right end of the pump chassis 370) positions on the pump chassis 370. Three left lateral support walls 384, 386, and 388 protrude from the bottom of the pump chassis 370 at locations to support the upper left side portion of the assembled cassettes 302 near the back thereof in proper positions in the first, second, and third positions, respectively. Likewise, three right lateral support walls 390, 392, and 394 protrude from the bottom of the pump chassis 370 at locations to support the rear-most extending upper portion of the assembled cassettes 302 on the right side thereof in proper positions in the first, second, and third positions, respectively.

Additional support and positioning for the installation of the assembled cassettes 302 into the first, second, and third positions are provided for the upper right back corner of the assembled cassettes 302 by three right corner support walls 396, 398, and 400, respectively. The three right corner support walls 396, 398, and 400 are L-shaped when viewed from the bottom (FIG. 62), and support and position the back of the assembled cassettes 302 behind the pump cylinders 112 (FIG. 4) and a portion of the right side of the assembled cassettes 302 adjacent the pump cylinders 112. Note that the three right lateral support walls 390, 392, and 394 and the three right corner support walls 396, 398, and 400 together provide continuous support and positioning for the assembled cassettes 302 in the first, second, and third positions, respectively.

Located in the raised material forming the left lateral support wall 384 near the back thereof is a threaded aperture 402. A single segment of raised material forms the right lateral support wall 390, the right corner support wall 396, and the left lateral support wall 386; located in that segment of raised material near the back thereof is a threaded aperture 404 on the left side near the right lateral support wall 390, and a threaded aperture 406 on the right side near the left lateral support wall 386. Likewise, a single segment of raised material forms the right lateral support wall 392, the right corner support wall 398, and the left lateral support wall 388; located in that segment of raised material near the back thereof is a threaded aperture 408 on the left side near the right lateral support wall 392, and a threaded aperture 410 on the right side near the left lateral support wall 388. Finally, a single segment of raised material forms the right lateral support wall 394 and the right corner support wall 400 near the back thereof is a threaded aperture 412 near the right lateral support wall 394.

Located in the segment of raised material forming the right lateral support wall 390, the right corner support wall 396, and the left lateral support wall 386 near the corner where the right lateral support wall 390 and the right corner support wall 396 meet is an aperture 414 which extends through the pump chassis 370 from top to bottom. Located in the segment of raised material forming the right lateral support wall 392, the right corner support wall 398, and the left lateral support wall 388 near the corner where the right lateral support wall 392 and the right corner support wall 398 meet is an aperture 416 which extends through the pump chassis 370 from top to bottom. Located in the segment of raised material forming the right lateral support wall 394 and the right corner support wall 400 near the corner where the right lateral support wall 394 and the right corner support wall 400 meet is an aperture 418 which extends through the pump chassis 370 from top to bottom.

Figure 46:
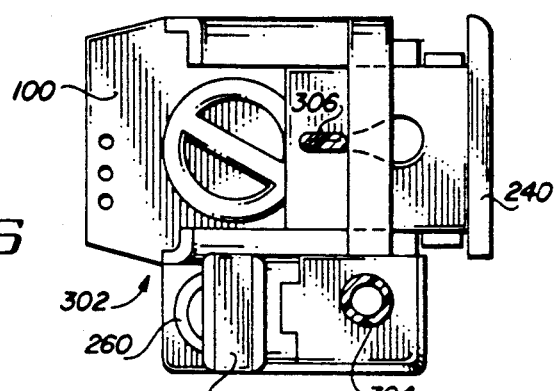
FIG. 46 is a bottom view of the assembled cassette shown in FIG. 45, with the tubing adapter removed for clarity and the slide latch in the opened position.
Figure 48:
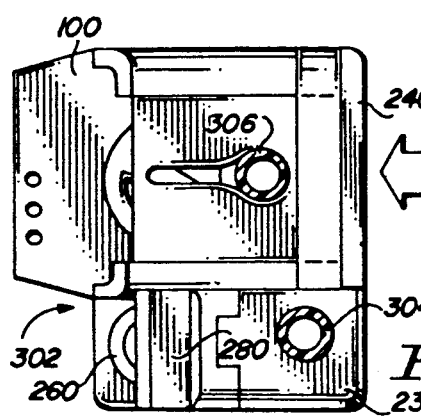
FIG. 48 is a bottom view of the assembled cassette shown in FIGS. 45 through 47, with the tubing adapter removed for clarity and the slide latch in the closed position.
Figure 47:
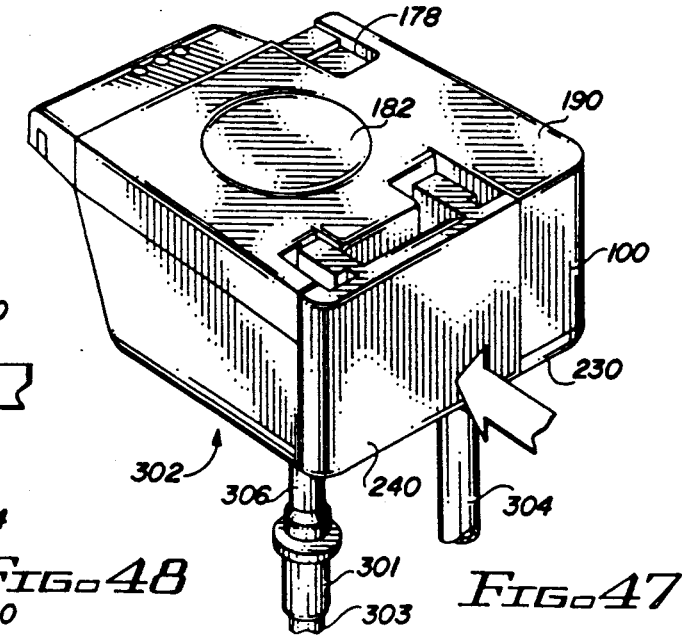
FIG. 47 is a perspective top view of the assembled cassette shown in FIGS. 45 and 46, with the slide latch in the closed position.

Note that with the assembled cassettes 302 positioned and mounted in the first, second, and third positions, the aperture 414, the aperture 416, and the aperture 418, respectively, will be directly back of the piston rods 292 of the assembled cassettes 302 (FIG. 46). The apertures 414, 416, and 418 will be used to mount the drive shafts connected to the jaws assembles 360 (FIGS. 59 through 61) used to drive the piston assembly 280.

Located between the left lateral support wall 384 and the right lateral support wall 390 is a longitudinal rectangular recess 420 in the bottom surface of the pump chassis 370. Similarly, located between the left lateral support wall 386 and the right lateral support wall 392 is a longitudinal rectangular recess 422 in the bottom surface of the pump chassis 370. Finally, located between the left lateral support wall 384 and the right lateral support wall 390 is a longitudinal rectangular recess 424 in the bottom surface of the pump chassis 370. While the rectangular recesses 420, 422, and 424 do not extend through the pump chassis 370, oval aperture 426, 428, and 430 smaller than the rectangular recesses 420, 422, and 424 are located in the rectangular recesses 420, 422, and 424, respectively, and extend through to the top side of the pump chassis 370.

The rectangular recesses 420, 422, and 424 will be used to mount sensor modules therein, and the oval aperture 426, 428, and 430 are to allow the wires from the sensor modules to extend through the pump chassis 370. Note that with the assembled cassettes 302 positioned and mounted in the first, second, and third positions, the rear-most extending upper portions of the assembled cassettes 302 will be located over the rectangular recesses 420, 422, and 424. Located behind the oval aperture 426, 428, and 430 are rectangular apertures 427, 429, and 431, respectively. The rectangular apertures 427, 429, and 431 are to allow the wires from the ultrasonic sensors to extend through the pump chassis 370.

Located in front of the right corner support wall 396 is a circular recess 432 in the bottom surface of the pump chassis 370. Similarly, located in front of the right corner support wall 398 is a circular recess 434 in the bottom surface of the pump chassis 370. Finally, located in front of the right corner support wall 400 is a circular recess 436 in the bottom surface of the pump chassis 370. While the circular recesses 432, 434, and 436 do not extend through the pump chassis 370, square apertures 438, 440, and 442 smaller than the circular recesses 432, 434, and 436 are located in the circular recesses 432, 434, and 436, respectively, and extend through to the top side of the pump chassis 370.

The circular recesses 432, 434, and 436 will be used to mount valve actuator guides therein, and the cylindrical aperture 450, 452, and 454 are to allow valve actuators to extend through the pump chassis 370 and to orient the valve actuator guides. Note that with the assembled cassettes 302 positioned and mounted in the first, second, and third positions, the circular recess 432, the circular recess 434, and the circular recess 436, respectively will correspond exactly with the locations of the domed portions 178 of the valve diaphragms 17 in the assembled cassettes 302 (FIG. 43).

Located to the left of the circular recess 432 and in front of the rectangular recess 420 is a circular recess 444 in the bottom surface of the pump chassis 370. Similarly, located to the left of the circular recess 434 and in front of the rectangular recess 422 is a circular recess 446 in the bottom surface of the pump chassis 370. Finally, located to the left of the circular recess 436 and in front of the rectangular recess 424 is a circular recess 448 in the bottom surface of the pump chassis 370. While the circular recesses 444, 446, and 448 do not extend through the pump chassis 370, cylindrical apertures 450, 452, and 454 of a smaller diameter than the circular recesses 444, 446, and 448 are located in the circular recesses 444, 446, and 448, respectively, and extend through to the top side of the pump chassis 370.

The circular recesses 444, 446, and 448 will be used to mount pressure transducers therein, and the cylindrical apertures 438, 440, and 442 are to allow wires from the pressure transducers to extend through the pump chassis 370. Note that with the assembled cassettes 30 positioned and mounted in the first, second, and third positions, the circular recess 444, the circular recess 446, and the circular recess 448, respectively, will correspond with the locations of the pressure diaphragms 182 of the valve diaphragms 170 in the assembled cassettes 302 (FIG. 43).

Projecting from the surface on the top side of the pump chassis 370 are a number of raised segments in which threaded apertures are located to support the drive assembly. A cylindrical raised segment 456 is located to the left of the cylindrical aperture 450 on the top side of the pump chassis 370. A laterally extending oval raised segment 458 is located between the square aperture 438 and the cylindrical aperture 452 on the top side of the pump chassis 370. A second laterally extending oval raised segment 460 is located between the square aperture 440 and the cylindrical aperture 454 on the top side of the pump chassis 370. A cylindrical raised segment 462 is located to the right of the square aperture 442 and is laterally aligned with the rear-most portions of the oval raised segments 458 and 460. Finally, a cylindrical raised segment 464 is located to the right of the square aperture 442 and is laterally aligned with the front-most portions of the oval raised segments 458 and 460.

Located in the cylindrical raised segment 456 is a threaded aperture 466. Located in the oval raised segment 458 is a threaded aperture 468 near the rear-most portion of the oval raised segment 458, a threaded aperture 470 near the front-most portion of the oval raised segment 458, and a threaded aperture 472 centrally located in the oval raised segment 458. Similarly, located in the oval raised segment 460 is a threaded aperture 474 near the rear-most portion of the oval raised segment 460, a threaded aperture 476 near the front-most portion of the oval raised segment 460, and a threaded aperture 478 centrally located in the oval raised segment 460. Located in the cylindrical raised segment 462 is a threaded aperture 480. Finally, located in the cylindrical raised segment 464 is a threaded aperture 482.

The apertures 414, 416, and 418 through the pump chassis 370 terminate in raised segments extending from the top surface of the pump chassis 370. A raised segment 484 is located around the opening of the aperture 414 on top of the pump chassis 370, a raised segment 486 is located around the opening of the aperture 416 on top of the pump chassis 370, and a raised segment 488 is located around the opening of the aperture 418 on top of the pump chassis 370.

Extending upwardly from the raised segment 484 behind the aperture 414 on the left side is a guide finger 490, and on the right side is a guide finger 492. The guide fingers 490 and 492 are parallel and have a space therebetween. Extending upwardly from the raised segment 486 behind the aperture 416 on the left side is a guide finger 494, and on the right side is a guide finger 496. The guide fingers 494 and 496 are parallel and have a space therebetween. Extending upwardly from the raised segment 488 behind the aperture 418 on the left side is a guide finger 498, and on the right side is a guide finger 500. The guide fingers 498 and 500 are parallel and have a space therebetween.

Referring now to FIGS. 66 through 69, a cassette guide 510 for use in guiding the installation of the assembled cassette 302 into the proper location for latching on the pump chassis 370 is illustrated. Disposed to the rear of the cassette guide 510 at the right side is an aperture 512, and at the left side is an aperture 514. The aperture 512 will be aligned with the threaded aperture 404 (FIG. 62), the threaded aperture 408, or the threaded aperture 412 while the aperture 514 will be aligned with the threaded aperture 402, the threaded aperture 406, or the threaded aperture 410 to install the cassette guide 510 in either the first, second, or third position.

The top side (FIG. 66) of the cassette guide 510 has a rectangular recess 516 therein, which rectangular recess 516 corresponds in size to the rectangular recesses 420, 422, and 424 in the pump chassis 370. The optical sensor modules will be accommodated between the rectangular recesses 516 in the cassette guides 510 and the rectangular recesses 420, 422, and 424 in the pump chassis 370. The right side of this rectangular recess 516 is exposed through a rectangular aperture 518 on the bottom of the cassette guide 510 (FIG. 67).

An area 520 on the bottom of the cassette guide 510 immediately to the front of the rectangular aperture 518 and an area 522 to the right and to the back of the rectangular aperture 518 is recessed upward from the surface 524 of the cassette guide 510. At the front right corner of the rectangular aperture 518 a square segment 528 extends downward to the level of the surface 524 of the cassette guide 510. Located immediately forward of the square segment 528 is a thin rectangular track 530 extending from the right side of the cassette guide 510. The thin rectangular track 530 terminates at the front end thereof in a blocking segment 532.

The front end of the cassette guide 510 has a rounded notch 534 therein, which rounded notch 534 is positioned when the cassette guide 510 is installed on the pump chassis 370 to receive the outlet tube mounting cylinder 144 on the cassette body 100 (FIG. 4). When the cassette guide 510 is installed on the pump chassis 370, the rear-most portion of the assembled cassette 302 will fit between the cassette guide 510 and the bottom of the pump chassis 370. Accordingly, the cassette guide 510 together with the various support walls on the bottom of the pump chassis 370 aids in the installation of the assembled cassettes 302 in the proper position for latching.

Extending downward from the surface 524 is a hollow lower segment 511 having a projection 513 extending toward the front. When the assembled cassette 302 is installed, the horizontal bottom portion 24 of the slide latch 240 will be located between the surface 524 and the projection 513. The lower segment 511 is hollow to receive the ultrasonic sensor housing, as will become apparent below. A hollow chimney 515 is located at the back of the cassette guide 510, and is in communication with the interior of the lower segment 511. When the cassette guide 510 is installed on the pump chassis 370, the interior of the hollow chimney 515 will be in communication with on of the rectangular apertures 427, 429, or 431 in the pump chassis 370, to allow wires from the ultrasonic sensor to extend therethrough.

Referring next to FIG. 70, a pump shaft 540 is illustrated which is essentially cylindrical. Near the top end of the pump shaft 540 on the front side thereof a cam follower wheel 542 is mounted for rotation about a short axle 544 extending orthogonally from the pump shaft 540. On the front side of the pump shaft 540 at the same location an alignment wheel 546 is mounted for rotation about a short axle 548 extending orthogonally from the pump shaft 540 on the opposite side of the short axle 544. Near the bottom end of the pump shaft 540 on the rear side thereof is a conical recess 550, which will be used to attach the jaws assembly 360 (FIG. 59 through 61) to the pump shaft 540.

Referring next to FIGS. 71 through 76, a slide lock 560 which is for mounting on the thin rectangular track 530 of the cassette guide 510 (FIG. 67) is illustrated. The slide lock 560 has a U-shaped slide channel 562 at the front thereof, with the open portion of the U facing left and extending from front to rear. The right side of the slide channel 562, which is the bottom of the U, has a rectangular notch 564 located near the front thereof, which notch 564 runs from the top to the bottom of the slide channel 562.

Extending back from the rear of the slide channel 562 at the bottom thereof is a thin rectangular connecting segment 566, which effectively extends from the leg of the U at the bottom of the slide channels 562. Attached at the rear edge of the rectangular connecting segment 566 is a U-shaped channel 568 with the open portion of the U facing right and extending from top to bottom. The forward leg of the U of the U-shaped channel 568 is attached to the rectangular connecting segment 56 at the top of the U-shaped channel 568. It will be appreciated that the top surface of the rectangular connecting segment 566 and the top of the U-shaped channel 568 (which is U-shaped) are coplanar, and that the interior surface of the lowermost leg of the slide channel 562 is also coplanar.

The upper left edge of the U-shaped channel 568 has a bevel 570 located thereon, with the bevel 570 being best illustrated in FIG. 76. The function of the bevel 570 is as a light reflector, and will become apparent later in conjunction with the discussion of the mechanism for latching the assembled cassette 302.

The power module to drive the main pump unit is not described herein, since it is not in any way related to the subject matter of the present invention. For a complete description of the construction of the power module, the above incorporated by reference application U.S. Ser. No. 128,121, entitled "Air-In-Line Detector for a Medication Infusion System," may be referred to.

Referring next to FIGS. 77 through 80, an upper ultrasonic housing 800 is illustrated. The upper ultrasonic housing 800 is hollow, and is open on the bottom thereof. The upper surface of the upper ultrasonic housing 800 has a U-shaped ridge 802 and a straight ridge 804 located thereon, with a rectangular aperture 806 located therebetween in the upper surface of the upper ultrasonic housing 800. The U-shaped ridge 802 and the straight ridge 804 are sized to fit within the lower segment 511 of the cassette guide 510 (FIG. 69).

Located in the front of the upper ultrasonic housing 800 is a slot 808 for receiving therein the outlet tube 306 of the assembled cassette 302. The slot 808 is deeper than it is wide and has a funnel-shaped entrance to allow the outlet tube 306 to easily be directed into the slot 808. In the preferred embodiment, the width of the slot 808 is narrower than the outside diameter of the outlet tube 306, causing the outlet tube 306 to fit in the slot 808 in a manner deforming the outlet tube 306.

The interior of the upper ultrasonic housing 800 may be thought of as three areas, one on each side of the slot 808, and a third area in the portion of the upper ultrasonic housing 800 in which the slot 808 does not extend. The first two areas are locations in which ultrasonic transducers (not shown) will be located, and the third area will be the location of a miniature printed circuit board (not shown). Referring particularly to FIG. 80, the first area, in the front and on the right side of the upper ultrasonic housing 800, is bounded by a wall 810 on the right side of the slot 808. The second area, in the front and on the left side of the upper ultrasonic housing 800, is bounded by a wall 812 on the left side of the slot 808.

Referring now to FIGS. 81 through 83, a lower ultrasonic housing 814 which will mount onto the bottom of the upper ultrasonic housing 800 is illustrated. Like the upper ultrasonic housing 800, the lower ultrasonic housing 814 is hollow, but the lower ultrasonic housing 814 is open on the top side thereof. The front portion of the lower ultrasonic housing 814 (the portion which will be under the first two areas inside the upper ultrasonic housing 800) is shallow, while the rear portion of the lower ultrasonic housing 814 is deeper. The lower ultrasonic housing 814 also has a slot 816 located therein, which slot 816 will be located under the slot 808 in the upper ultrasonic housing 800 when the lower ultrasonic housing 814 is mounted on the upper ultrasonic housing 800. The slot 816 also has a funnel-shaped entrance, like the slot 808.

Located under the portion of the lower ultrasonic housing 814 having the slot 816 therein is a recessed area 818. The recessed area 818 is located on both the left side and the right side of the slot 816 in the lower ultrasonic housing 814. In the preferred embodiment, the recessed area 818 is frustroconically shaped, as best shown in FIGS. 83 and 83A. The frustroconically shaped recessed area 818 is spaced slightly away from the front of the lower ultrasonic housing 814. Located on the bottom and at the front of the lower ultrasonic housing 814 on each side of the slot 816 therein are two ramps 820 and 822 which are inclined toward the frustroconically shaped recessed area 818.

The recessed area 818 and the two ramps 820 and 822 are designed to capture and retain the tapered portion 305 of the tubing adapter 301 (FIG. 43) therein. Accordingly, the size of the recessed area 818 is approximately identical to the size of the tapered portion 305 of the tubing adapter 301. The two ramps 820 and 822 are located as shown in FIG. 83A to draw the tapered portion 305 of the tubing adapter 301 from a position on the two ramps 820 and 822 to a position in contact with the recessed area 818. This operation of engagement of the tapered portion 305 of the tubing adapter 301 with the recessed area 818 will be further discussed in detail below.

Referring next to FIG. 84, a portion of a two-piece flex circuit 824 and 825 is illustrated. The flex circuit 824 may be thought of as a straight base portion having four arms extending orthogonally from the side of the base portion. At the end of each of the four arms is an exposed circular conductive pad 826, 828, 830, or 832. A series of four terminals 834, 836, 838, and 840 are located on the flex circuit 824 on the base portion near the center thereof. The conductive pad 826 is electrically connected to the terminal 834 by a conductor 850, the conductive pad 828 is electrically connected to the terminal 836 by a conductor 852, the conductive pad 830 is electrically connected to the terminal 838 by a conductor 854, and the conductive pad 832 is electrically connected to the terminal 840 by a conductor 856.

The flex circuit 825 is a long tail segment having four terminals 842, 844, 846, and 848 on the end adjacent the flex circuit 824. The base portion of the flex circuit 824 and the flex circuit 825 are to be located close together, and thus form a T. Four more conductors 858, 860, 862, and 864 are located in the flex circuit 825. The conductor 858 is electrically connected to the terminal 842, the conductor 860 is electrically connected to the terminal 844, the conductor 862 is electrically connected to the terminal 846, and the conductor 864 is electrically connected to the terminal 848. It will be appreciated by those skilled in the art that the conductors 850, 852, 854, and 856 and the conductors 858, 860, 862, and 864 are electrically insulated on both sides thereof.

Referring next to FIG. 85, the assembly of two ultrasonic transducers 866 and 868 to the flex circuit 824 is illustrated. The transducers 866 and 868 are typically ceramic ultrasonic transducers. In a typical assembly of ultrasonic transducers, soldering is used, with the result of possible damage to the ceramic ultrasonic transducer. The present invention instead uses conductive adhesive transfer tape, which has adhesive on both sides and is electrically conductive. Such conductive transfer tape is commercially available from 3M under the product identification number 9703. A disc-shaped segment of conductive transfer tape 870 is placed between the conductive pad 826 and one side (called the back side) of the ultrasonic transducer 866. The disc-shaped segment of conductive transfer tape 870 both secures the conductive pad 826 to the one side of the ultrasonic transducer 866 and makes electrical contact between the conductive pad 826 and the one side of the ultrasonic transducer 866

A disc-shaped segment of conductive transfer tape 872 is placed between the conductive pad 828 and the other side (the front side) of the ultrasonic transducer 866. A disc-shaped segment of conductive transfer tape 874 is placed between the conductive pad 830 and on side (the front side) of the ultrasonic transducer 868. A disc-shaped segment of conductive transfer tape 876 is placed between the conductive pad 832 and the other side (the back side) of the ultrasonic transducer 868. Thus, the ultrasonic transducers 866 and 868 are assembled and electrically connected to the flex circuit 824.

The disc-shaped segments of conductive transfer tape 870, 872, 874, and 876 are used in the preferred embodiment. Instead of using conductive transfer tape, conductive epoxy could be used, although the conductive transfer tape is preferred.

Referring next to FIG. 86, the ultrasonic transducers 866 and 868 are assembled into the upper ultrasonic housing 800. The portion of the flex circuit 824 on the side of the conductive pad 828 opposite the ultrasonic transducer 866 is adhesively bonded to the wall 812, thus securing the ultrasonic transducer 866 to the wall 812, Similarly, the portion of the flex circuit 824 on the side of the conductive pad 830 opposite the ultrasonic transducer 868 is adhesively bonded to the wall 810, thus securing the ultrasonic transducer 868 to the wall 810. The adhesive used is preferably an elastomeric adhesive which goes on in a thin coat with no air pockets. One such adhesive is Black Max adhesive. A small block of foam 878 is used to bear against the ultrasonic transducer 866 and the associated portions of the flex circuit 824 attached thereto. Similarly, a small block of foam 880 is used to bear against the ultrasonic transducer 868 and the associated portions of the flex circuit 824 attached thereto.

The flex circuit 825 is directed through the rectangular aperture 806 in the flex circuit 824. The connectors 858, 860, 862, and 864 are electrically connected to a connector 882. Referring now to FIG. 87, a small printed circuit board 884 having various components thereon is electrically connected to the terminals 834, 846, 838, and 840 (FIG. 84) on the flex circuit 824 and the terminals 842, 844, 846, and 848 on the flex circuit 825. The printed circuit board 884 then rests in the third area in the upper ultrasonic housing 800, as shown.

Figure 85A:
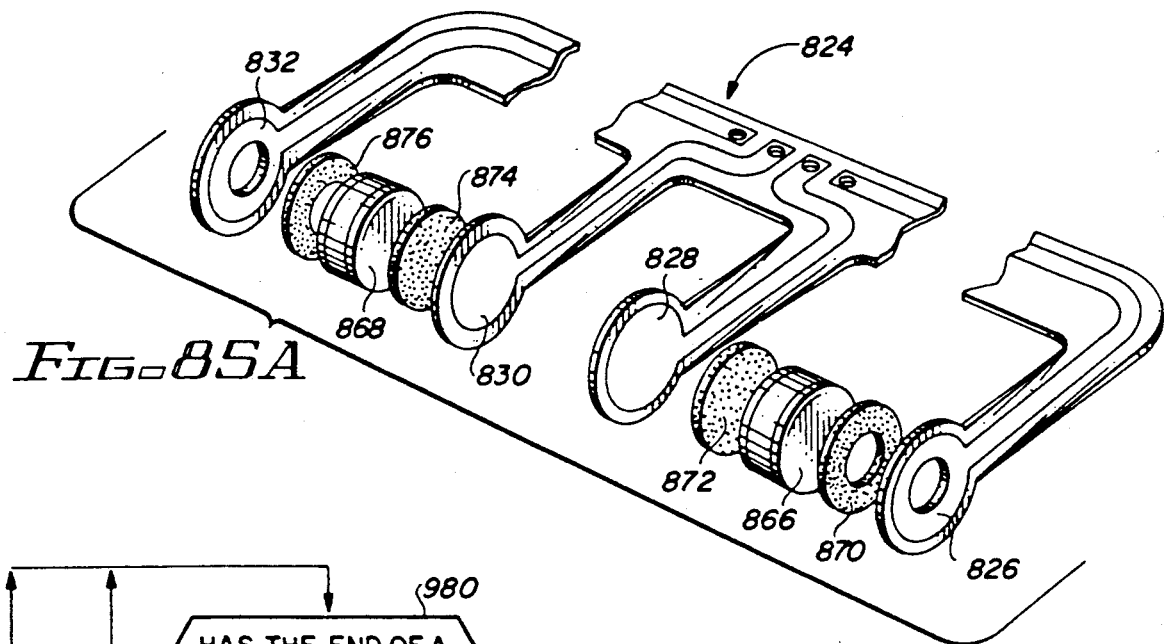
FIG. 85A is a partially exploded perspective view showing an alternate embodiment in which portions of the flex circuit and the conductive transfer tape on the back sides of the ultrasonic transducers have apertures therethrough.

In an alternate embodiment illustrated in FIG. 85A, an aperture is used on the conductive pads and the disc-shaped segments of conductive transfer tape located on the back sides of each of the ultrasonic transducers 866 and 868. The conductive pad 826 and the disc-shaped segment of conductive transfer tape 870 each have apertures extending therethrough on the back side of the ultrasonic transducer 866. Similarly, the conductive pad 832 and the disc-shaped segment of conductive transfer tape 876 each have apertures extending therethrough on the back side of the ultrasonic transducer 868. The apertures allow the ultrasonic transducers 866 and 868 to flex more freely, and the strength of the output signal is approximately doubled by using the apertures as described.

The apertures in the conductive pads 826 and 832 and in the disc-shaped segments of conductive transfer tape 870 and 876 are centrally located therein. The diameters of the ultrasonic transducers 866 and 868, as well as the diameters of the conductive pads 826, 828, 830, and 832 are approximately 0.21 inches. In the preferred embodiment, the diameters of the apertures in the conductive pads 826 and 832 and in the disc-shaped segments of conductive transfer tape 870 and 876 are approximately 0.125 inches. The size of the apertures is dictated on the one hand by the desire to maintain a low resistance connection and on the other hand by the desire to maximize the amount of flexion in the ultrasonic transducers 866 and 868.

Referring next to FIGS. 88 through 90, an optical sensor module 670 is illustrated. The optical sensor module 670 is essentially rectangular in cross-section, with a wider rectangular flange 672 on top of the rectangular portion, and an oval portion 674 above the rectangular flange 672. A flex cable 676 extends from the top of the oval portion 674. Located around the circumference of the oval portion 674 is a groove 678, which will receive an elastomeric O-ring, which will retain the oval portion 674 of the optical sensor modules 670 in the oval apertures 426, 428, or 430. The rectangular flange 672 of the optical sensor modules 670 will fit into the rectangular recesses 420, 422, or 424, in the first, second, or third pump positions, respectively.

The rectangular portion of the optical sensor module 670 has located in the front thereof and immediately under the rectangular flange 672 a notch indicated generally by 680, which notch 680 will receive the rearmost portion of the assembled cassette 302. Further details of the optical sensor module 670 are not necessary for the purposes of the present application. For a complete description of the construction of the optical sensor module 670, the above incorporated by reference application U.S. Ser. No. 128,121, entitled "Air-In-Line Detector for a Medication Infusion System," may be referred to.

Referring next to FIGS. 91 through 93, a valve actuator 620 is illustrated. The valve actuator 620 includes a thin, essentially rectangular portion 622, and has a circular bearing 624 rotatably mounted near the top thereof. The circular outer diameter of the bearing 624 extends slightly above the top of the rectangular portion 622. The rectangular portion 622 of the valve actuator 620 has chamfered edges on the lower end thereof as indicated generally at 625, and has a small notch 626, 628 in both lateral sides of the rectangular portion 622 at a location above the lower end thereof. The small notches 626 and 628 are for receiving means for retaining the valve actuator 620 in position once it is installed; this will become evident below in conjunction with the discussion of the assembly of the main pump unit.

Moving next to FIGS. 94 and 95, a valve actuator guide 630 is illustrated which is used to guide and retain in position pairs of the valve actuators 620. The upper portion 632 of the valve actuator guide 630 is square in cross-section, and lower portion 634 is circular in cross-section. Extending vertically through both the square upper portion 632 and the circular lower portion 634 of the valve actuator guide 630 are two apertures 636 and 638, which are rectangular in cross-section. The apertures 636 and 638 are sized to allow the rectangular portion 622 of the valve actuator 620 to slide freely therein in each of the apertures 636 and 638.

One of the valve actuator guides 630 will be installed into each of the pump positions in the pump chassis 370. In the first pump position, the square upper portion 632 of the valve actuator guide 630 will be located in the square aperture 438 on the pump chassis 370 and the circular lower portion 634 of the valve actuator guide 630 will be located in the circular recess 432 on the pump chassis 370. In the second pump position, the square upper portion 632 will be located in the square aperture 440 and the circular lower portion 634 will be located in the circular recess 434. In the third pump position, the square upper portion 632 will be located in the square aperture 442 and the circular lower portion 634 will be located in the circular recess 436.

Referring next to FIGS. 96 through 98, a pressure transducer 660 is illustrated. One of the pressure transducers 660 will be installed in the pump chassis 370 in each pump position, in the circular recesses 444, 446, and 448. The pressure transducer 660 is essentially cylindrical, with a groove 662 located around the circumference of the pressure transducer 660. The groove 662 is to receive an elastomeric O-ring, which will both retain the pressure transducers 660 in the circular recesses 444, 446, and 448, and provide a fluid seal. Located on top of the pressure transducer 660 is a square segment 664 in which is located the actual transducer, which square segment 664 will be received in the cylindrical apertures 450, 452, and 454. Extending upward from the square segment 664 are several leads 666.

Referring next to FIGS. 99 and 100, a valve actuator seal 650 is shown which is used both to provide a fluid seal and, more importantly, to retain the valve actuators 620 (FIGS. 85 through 87) in an upward position with their bearings 624 against the lower portion 593 of the power module cam 580. The outer circumference of the valve actuator seals 650 is of a size allowing them to be retained in a friction fit in the circular recesses 432, 434, and 436 below the valve actuator guides 630. A metal ring (not shown) may be molded into the outer diameter of the valve actuator seals 650 to better enable them to be better retained in the circular recesses 432, 434, and 436.

Two apertures 652 and 654, which are rectangular in configuration, are located in the valve actuator seal 650 to receive the bottom portions of the rectangular portion 622 of the valve actuator 620. The lengths of the apertures 652 and 654 are shorter than the width of the rectangular portion 622 of the valve actuator 620, with the small notches 626 and 628 in the rectangular portion 622 being used to capture to ends of one of the apertures 652 and 654. It will be appreciated that the small notches 626 and 628 of the valve actuators 620 will engage the apertures 652 and 654 in the valve actuator seal 650, thereby allowing the valve actuator seal 650 to exert a bias on the valve actuators 620. As will be seen below, the bias exerted by the valve actuator seal 650 on the valve actuators 620 is an upward one urging the valve actuators 620 against the lower portion 593 of the power module cam 580.

In the previous discussions of the various parts of the main pump unit, the function and interrelationship between parts has been briefly discussed. Before moving on to the operation of the main pump unit and the assembled cassette 302, a brief discussion of the assembly of the main pump unit is in order. This discussion specifically refers to FIGS. 62 through 65 (the pump chassis 370) and to FIGS. 101–103, and also to other figures which are specifically mentioned in the discussion. Details of the drive assembly are omitted in this specification.

A hollow cylindrical pump shaft bearing 640 is installed in both the top and the bottom of each of the apertures 414, 416, and 418 in the pump chassis 370. In the preferred embodiment, the pump shaft bearings 640 fit in the apertures 414, 416, and 418 in an interference fit to retain them in the apertures 414, 416, and 418 in the pump chassis 370. The pump shaft bearing 640 are preferably made of a low friction material such as Teflon to allow the pump shafts 540 to move freely therein.

Next, the valve actuator guides 630 are installed from the bottom of the pump chassis 370 into the circular recess 432 and the square aperture 438 in the first pump position, into the circular recess 434 and the square aperture 440 in the second pump position, and into the circular recess 436 and the square aperture 442 in the third pump position. With the valve actuator guides 630 installed in the pump chassis 370 the bottom surface of the valve actuator guides 630 leaves a portion of the circular recesses 432, 434, and 436 open from the bottom side of the pump chassis 370. The valve actuator seals 650 (FIGS. 97 and 98) will be installed later in the circular recesses 432, 434, and 436 below the valve actuator guides 630.

The next step in the assembly is to install the pressure and optical sensor modules. The pressure transducers 660 (FIGS. 96 through 98) are installed from the bottom of the pump chassis 370 into the circular recesses 444, 446, and 448. The pressure transducers 660 are essentially cylindrical, and with O-rings in the grooves 662 fit snugly into the circular recesses 444, 446, and 448 with their bottom surfaces flush with the bottom surface of the pump chassis 370 around the circular recesses 444, 446, and 448; the tops of the cylindrical portion of the pressure transducers 660 fit against the cylindrical apertures 450, 452, and 454 in the pump chassis 370. Not shown in the drawings is the preferred embodiment's use of a thin membrane adhesively placed over the bottom of the pressure transducer 660 and the portions of the bottom surface of the pump chassis 370 thereabout. This thin membrane protects the pressure transducer 660 from fluids which may inadvertently or accidentally end up on the device.

The optical sensor assembles 570 (FIGS. 88 through 90) are installed in the rectangular recesses 420, 422, and 416 of the pump chassis 370, with the oval portions 674 of the optical sensor modules 670 fitting into the oval apertures 426, 428, and 430. The optical sensor modules 670 are retained in position by the pressure of O-rings in the grooves 678 in the optical sensor modules 670, and by the cassette guides 510.

The next step in the assembly of the main pump unit mechanical components onto the pump chassis 370 is the installation of the cassette guide 510 (FIGS. 66 through 69) and the slide lock 560 (FIGS. 71 through 76). The slide lock 560 is installed onto the cassette guide 510 by placing the portion of the slide lock 560 including the bottom of the slide channel 562 into the rectangular aperture 518 in the cassette guide 510 from the top, with the rectangular connecting segment 566 of the slide lock 560 extending over the portion of the are 522 in the back of the cassette guide 510. This aligns the interior of the U-shaped slide channel 562 on the slide lock 560 with the back end of the thin rectangular track 530 on the cassette guide 510. The slide lock 560 is then moved forward with respect to the cassette guide 510, with the interior of the slide channel 562 fitting over the thin rectangular track 530 until the blocking segment of the cassette guide 510 is contacted by the slide lock 560.

The upper ultrasonic housing 800 and its associated components as shown in FIG. 87 are then covered by attaching the lower ultrasonic housing 814. In the preferred embodiment, one of three manufacturing techniques may be used to attach the upper ultrasonic housing 800 and the lower ultrasonic housing 814 together. They may be adhesively secured together, they may be ultrasonically welded together, or a potting material may be used to fill the interiors of both components to produce a potted assembly. The upper ultrasonic housing 800 is then adhesively attached to the cassette guide 510, with the flex circuit 825 extending through the chimney 515 of the cassette guide 510. The U-shaped ridge 802 and the straight ridge 804 fit into the interior of the lower segment 511 of the cassette guide 510, and the adhesive securely attaches the upper ultrasonic housing 800 to the cassette guide 510.

The cassette guides 510 together with the slide locks 560 may then be mounted into the three pump positions on the pump chassis 370, which already contain the optical sensor module 670, using two screws (not shown). In the first pump position, the flex circuit 825 which extends through the chimney 515 of the cassette guide 510 is fed through the rectangular aperture 427 in the pump chassis 370. A screw is placed through the aperture 514 in the cassette guide 510 into the threaded aperture 402 in the pump chassis 370, and a second screw is placed through the aperture 512 in the cassette guide 510 into the threaded aperture 404 in the pump chassis 370.

In the second pump position, the flex circuit 825 which extends through the chimney 515 of the cassette guide 510 is fed through the rectangular aperture 429 in the pump chassis 370. A screw is placed through the aperture 514 in the cassette guide 510 into the threaded aperture 406 in the pump chassis 370, and a second screw is placed through the aperture 512 in the cassette guide 510 into the threaded aperture 408 in the pump chassis 370. In the third pump position, the flex circuit 825 which extends through the chimney 515 of the cassette guide 510 is fed through the rectangular aperture 431 in the pump chassis 370. A screw is placed through the aperture 514 in the cassette guide 510 into the threaded aperture 410 in the pump chassis 370, and a second screw is placed through the aperture 512 in the cassette guide 510 into the threaded aperture 412 in the pump chassis 370. By way of example, the cassette guide 510 and the slide lock 560 are shown mounted in the first pump position in FIG. 101.

Next, the pump shafts 540 are installed in the pump shaft bearings 640, which have previously been installed in the apertures 414, 416, and 418. The end of the pump shafts 540 containing the conical recess 550 therein are inserted through the pump shaft bearings 640 from the top, with the alignment wheel 546 being located between one of the three pairs of guide fingers, namely the guide fingers 490 and 492 for the first pump position, the guide fingers 494 and 496 for the second pump position, and the guide fingers 494 and 496 for the third pump position. For example, the pump shaft 540 is shown installed in the first pump position in FIG. 101.

The valve actuators 620 are installed next, with one pair of the valve actuators 620 being installed in each pump position. The bottom ends of the valve actuators 620 having the chamfered edges 625 are inserted through the top sides of the valve actuator guides 630, with one pair of the valve actuators 620 being installed in each of the three valve actuator guides 630. The pair of valve actuators 620 are inserted into the apertures 636 and 638 in the valve actuator guides 630 with the bearings 624 on each of the pair of the valve actuators 630 facing away from each other.

It will be appreciated that the rectangular portions 622 of the valve actuators 620 will extend downward through the apertures 636 and 638 in the valve actuator guides 630. As stated above, valve actuator seals 650 are used in each of the three pump positions, and are mounted from the bottom of the pump chassis 370 into the circular recesses 432, 434, and 436 below the valve actuator guides 630. The outer circumference of the valve actuator seals 650 causes them to be retained in a friction fit in the circular recesses 432, 434, and 436.

Figure 113:
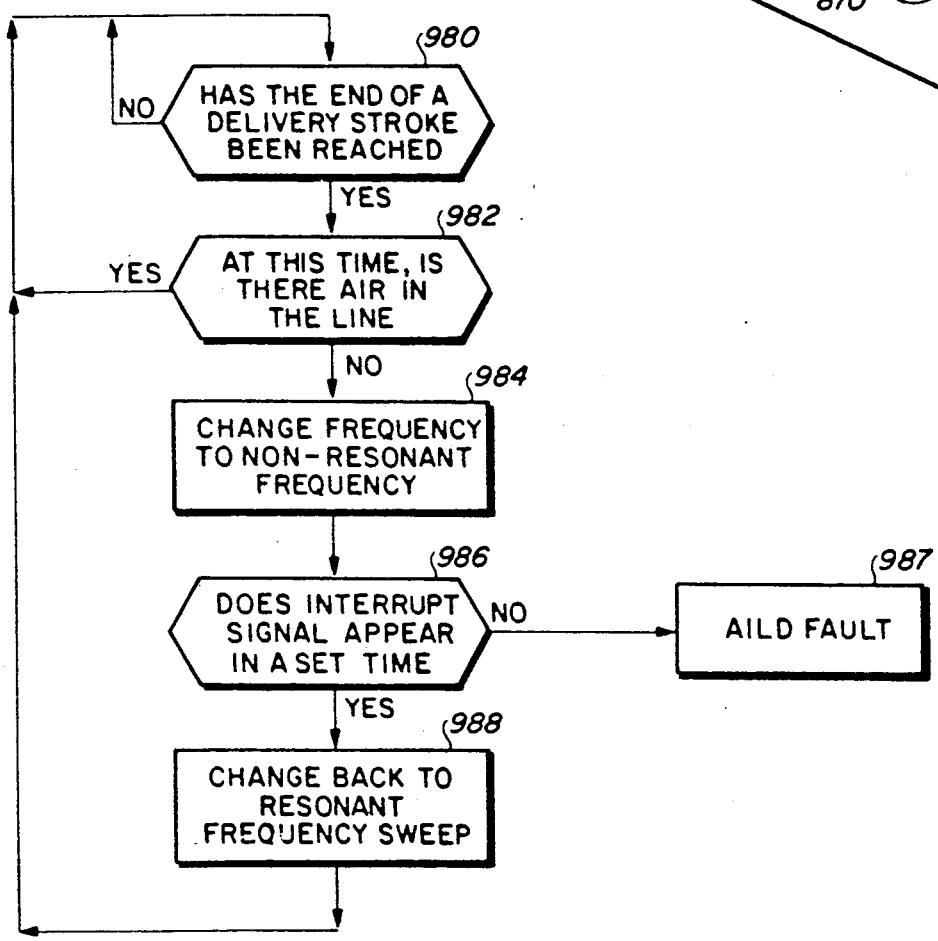
FIG. 113 is a simplified flow diagram illustrating the operation of the air-in-line detector self-test system.

The lower ends of the rectangular portions 622 of each pair of the valve actuators 620 extend downward through the apertures 652 and 654 in the valve actuator seal 650. The small notches 626 and 628 in one of the valve actuators 620 in each pair is retained in the aperture 652 in the valve actuator seal 650, and the other one of the valve actuators 620 in each pair is retained in the aperture 654. As shown in FIGS. 113 and 114, the valve actuator seals 650 will tend to urge the valve actuators 620 in an upward direction. In the preferred embodiment, the bottoms of the valve actuators 620 having the chamfered edges 625 will protrude somewhat from the bottom surface of the pump chassis 370 around the circular recesses 432, 434, and 436 even when the valve actuators 620 are in their open position. For example, in their closed position they may protrude approximately thirty thousands of an inch, and in their open position they may protrude seventy thousands of an inch.

This upward biasing of the valve actuator 620 is essential both to allow the assembled cassettes 302 to be freely inserted, and to maintain the valve actuators 620 in an upward position with their bearings 624 against the lower portion 593 of the power module cam 580. The valve actuator seals 650 accordingly function both to provide a fluid seal and to bias the valve actuators 620 in the upward position described.

The next step in the assembly of the main pump unit is to install power module assemblies (one of which is shown in FIG. 101) onto each of the three pump positions on the pump chassis 370. For the details of this procedure, the above incorporated by reference application U.S. Ser. No. 128,121, entitled "Air-In-Line Detector for a Medication Infusion System," may be referred to.

The final component to be installed is the jaws assembly 360 (FIGS. 59 through 61), with one jaws assembly 360 being installed in each of the three pump positions onto the bottom of the pump shafts 540, which are installed in the apertures 414, 416, and 418. The bottom end of the pump shaft 540 having the conical recess 550 therein is inserted into the cylindrical aperture 316 in the latch head 310 of the jaws assembly 360. A retaining screw (not shown) is screwed into the threaded aperture 318 in the latch head 310, and into the conical recess 550 of the pump shaft 540 to retain the jaws assembly 360 in place on the bottom of the pump chassis 370.

The location of the installed jaws assembly 360 is shown in FIG. 102, with the slide lock 560 and the latch jaw 340 in the open position. The link pin 354 on the latch jaw 340 is located in the U-shaped channel 568 of the slide lock 560, and movement of the slide lock 560 will accordingly cause the latch jaw 340 to move. When the slide lock 560 is fully forward, as shown in FIG. 102, the latch jaw 340 will be in the open position, with the jaw portion 342 of the latch jaw 340 away from the right jaw 314 of the latch head 310. When the slide lock 560 is pushed toward the back of the pump chassis 370, as shown in FIG. 103, the latch jaw 340 will be in the closed position, with the jaw portion 342 of the latch jaw 340 closely adjacent the right jaw 314 of the latch head 310.

This completes the discussion of the assembly of the main pump unit with three pump positions. It is now appropriate to discuss the installation of the assembled cassette 302 into the first pump position. The installation of the assembled cassette 302 into the other two pump positions is identical to the installation into the first pump position.

With the slide latch 240 pulled back fully away from the front of the assembled cassette 302 (FIGS. 45 and 46), the wider portion of the elongated, tear-shaped aperture 258 in the slide latch 240 will close the outlet tube 306, preventing fluid from flowing through the assembled cassette 302. The inlet tube 304 is connected to a fluid source such as an IV bag (not shown), and the delivery tubing 303 is connected to a fluid delivery device such as an injection set (not shown), the use of which is well known in the art. The slide latch 240 is opened, together with any other closures in the IV bag line, and fluid fills the lines, the assembled cassette 302, and the injection set. By tapping or shaking the assembled cassette 302 any residual air bubbles will flow out through the line. The slide latch 240 is then pulled back and the outlet tube 306 is closed, and the system is in a primed condition with the assembled cassette 302 ready to be installed onto the main pump unit.

When the slide latch 240 is pulled back, an opening is left between the front portion 242 of the slide latch 240 and the front top portion of the assembled cassette 302 (made up of the cassette body 100 and the retainer cap 190) facing the front portion 242 of the slide latch 240. By way of the example used herein where the assembled cassette 302 is to be mounted in the first position (the position on the left end of the pump chassis 370), the opening between the front portion 242 of the slide latch 240 and the front top portion of the assembled cassette 302 will admit the first pair of angled segments 372 and 374 as the assembled cassette 302 is installed. The top surface of the assembled cassette 302, which is the retainer cap 190 (FIG. 43), will mount against the bottom of the pump chassis 370 (FIG. 62).

Prior to installing the assembled cassette 302 into the main pump unit, the slide lock 560 must be fully forward with the latch jaw 340 opened away from the latch head 310, as mentioned previously and as shown in FIG. 102. In addition, the jaws assembly 360 should be in its fully upward position.

Referring now to FIG. 104, the rear-most edge of the assembled cassette 302 is tilted upward in front of the first pump position. Note also the angled position of the tubing adapter 301. The rear-most edge of the top of the assembled cassette 302 is then placed against the bottom of the pump chassis 370 between the pressure transducer 660 (mounted flush with the bottom of the pump chassis 370) and the top side of the cassette guide 510, as shown in FIG. 105. As the assembled cassette 302 is so positioned, the outlet tube 306 will begin to move into the funnel-shaped entrances to the slots 808 and 816 in the upper ultrasonic housing 800 and the lower ultrasonic housing 814, respectively. Simultaneously, the top of the tapered portion 305 of the tubing adapter 301 will contact the ramps 820 and 822 on the lower ultrasonic housing 814, as shown in FIG. 105. This engagement is key, since the ramps 820 and 822 will urge the tapered portion 305 of the tubing adapter 301 rearward toward the recessed area 818.

The rear-most portion of the top of the assembled cassette 302 is slid toward the back of the pump chassis 370 into position between the left lateral support wall 384 on the left side thereof and the right lateral support walls 390 on the right side thereof, with most of the rear-most portion of the top of the assembled cassette 302 fitting into the notch 680 in the optical sensor module 670. The upper right back corner of the assembled cassette 302 is supported and positioned in the back of the assembled cassette 302 behind the pump cylinder 112 (FIG. 4) and on the portion of the right side of the assembled cassette 302 adjacent the pump cylinder 112 by the right corner support wall 396.

As this movement of the assembled cassette 302 rearward into engagement with the main pump unit is occurring, the outlet tube 306 will continue to be pulled into the slots 808 and 816 in the upper ultrasonic housing 800 and the lower ultrasonic housing 814, respectively. The tapered portion 305 of the tubing adapter 301 will slide back into the recessed area 818, as shown in FIG. 106. Thus, the installation of the assembled cassette 302 into the main pump unit will automatically engage the outlet tube 306 in position between the ultrasonic transducers 866 and 868. The outlet tube 305 is deformed slightly in the slots 808 and 816 since the width of the slots 808 and 816 is less than the outer diameter of the outlet tube 306. This ensures good contact of the outlet tube 306 with the walls 810 and 812 in the upper ultrasonic housing 800, and thus good contact with the ultrasonic transducers 866 and 868.

When the assembled cassette 302 is pushed fully back in place, the front of the assembled cassette 302 is tilted upward against the bottom of the pump chassis 370, stretching slightly the outlet tube 306. At this point, the first pair of angled segments 372 and 374 on the bottom of the pump chassis 370 fitting into the area between the front portion 242 of the slide latch 240 and the front top portion of the assembled cassette 302. The slide latch 240 may then be pushed into the cassette body 100 as shown in FIG. 106, sliding the inverted L-shaped portion 250 of the slide latch 240 into engagement with the angled segment 372, and sliding the inverted, backwards L-shaped portion 252 of the slide latch 240 into engagement with the angled segment 374. The assembled cassette 302 will thus be held in position on the bottom of the pump chassis 370 until the slide latch 240 is again pulled back, releasing the assembled cassette 302.

Simultaneously, the outlet tube 306 will be opened, but fluid will not flow through the outlet tube 306 since at least one of the valve actuators 620 will be in its fully downward position at any given time, thereby preventing free flow through the assembled cassette 302 whenever the assembled cassette 302 is installed on the main pump unit. It will also be noted that in this initially installed position, the piston cap portion 262 is located at the very top of the pump cylinder 112.

The pumping operation of the system described above is not fully described herein. Rather, for a complete description of the pumping operation the above incorporated by reference application U.S. Ser. No. 128,121, entitled "Air-In-Line Detector for a Medication Infusion System," may be referred to.

The air-in-line detector of the present invention uses the pair of ultrasonic transducers 866 and 868 (FIG. 86) to detect the presence of air in the outlet tube 306 of the assembled cassette 302 (FIG. 106). The basic principle of operation is simple—fluids readily propagate ultrasonic energy while air or foam is a poor conductor of ultrasonic energy, several orders of magnitude less than fluids. Assume for the discussion of operation of the system that the ultrasonic transducer 866 is the transmitter and the ultrasonic transducer 868 is the receiver. When the ultrasonic transducer 866 is driven by an oscillating signal at a resonant frequency, it will vibrate at that frequency. As the driving frequency moves away from the resonant frequency, the vibration will diminish to a very small value at some distance away from the resonant frequency. Thus, the strength of the vibrations is at a maximum at the resonant frequency, and will diminish as the driving frequency moves either higher or lower than the resonant frequency.

In order for the system to function at its optimum, the ultrasonic transducer 866 and the ultrasonic transducer 868 should have approximately the same resonant frequency. The vibrations from the ultrasonic transducer 866 are directed through a segment of tubing to the ultrasonic transducer 868, where they will cause an output from the ultrasonic transducer 868 which is proportional to the strength of the vibrations received by the ultrasonic transducer 868. If there is a good conduit of vibrations between the ultrasonic transducer 866 and the ultrasonic transducer 868, the output from the ultrasonic transducer 868 will closely resemble the resonant input signal used to drive the ultrasonic transducer 866.

When ultrasonic vibrations are generated by the ultrasonic transducer 866, they must pass through the outlet tube 306 to reach the ultrasonic transducer 868. If the outlet tube 306 has fluid therein at the location between the ultrasonic transducers 866 and 868, the ultrasonic vibrations will easily pass therethrough. On the other hand, if there is air in the outlet tube 306 at the location between the ultrasonic transducers 866 and 868, the ultrasonic vibrations will become greatly attenuated and a much lower signal (two orders of magnitude lower) will be detected.

Figure 107:
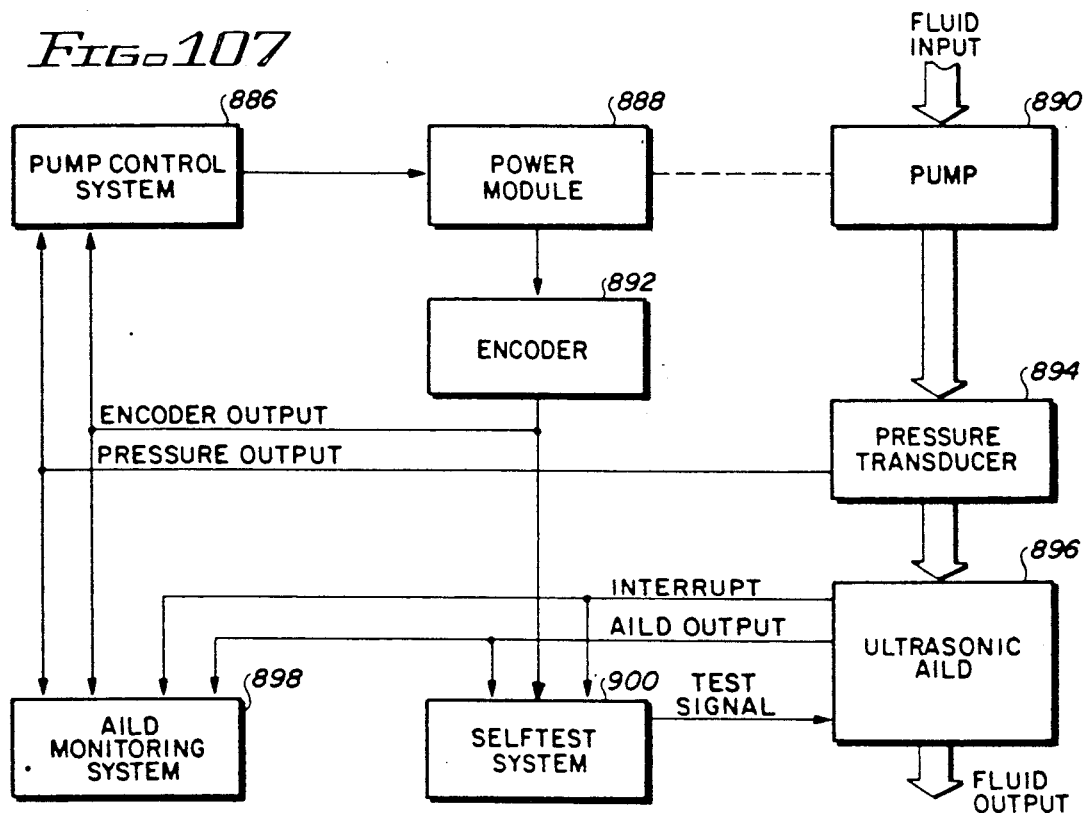
FIG. 107 is a functional schematic diagram of the entire operating system of the infusion pump of the present invention, showing the ultrasonic air-in-line detector system and self-test therefor.

A simplified overview of the operation of the entire pump system is illustrated in FIG. 107. A pump control system 886 is used to drive a power module 888, which in turn operates a pump 890. An encoder 892 is used to supply position information from the power module 888, which position information will indicate both the position of the pump 890 (which in the present system is a piston-type pump located in the assembled cassette 302) and the amount of fluid pumped by the pump 890. The pump 890 pumps fluid from a fluid input through a pressure transducer 894, and then through an ultrasonic air-in-line detector (AILD) 896 to a fluid output.

The encoder 892 provides an encoder output which is supplied to the pump control system 886 as a feedback signal. The pressure transducer 894 provides a pressure output signal which is supplied to the pump control system 886 for use in monitoring the pressure to detect an occluded line situation. The AILD scheme used by the system of the present invention has two additional components, namely an AILD monitoring system 898 and a self-test system 900. The ultrasonic AILD 896 supplies two signals to the AILD monitoring system 898 and the self-test system 900, specifically an interrupt signal and an AILD output signal. The nature of these two signals will become evident in the detailed discussion below.

The AILD monitoring system 898 is used to monitor the signals from the ultrasonic AILD 896 to determine when air is in the fluid line. More particularly, in the preferred embodiment the AILD monitoring system 898 will be used to determine when a predetermined amount of air has passed through the line during the passage past the sensor of a particular quantity of pumped volume, which is called a volume window. When there has been the predetermined amount of air in the fluid line during a volume window, an alarm will be sounded and the pumping of fluid will be ceased. The concept of a volume window will be explained in detail below.

The self-test system 900 is used periodically to ensure that the ultrasonic AILD 896 is functioning properly, and not giving false assurances that there is fluid in the line when in fact air is in the line. The self-test system 900 functions by providing a test signal to the ultrasonic AILD 896 causing it to operate during the self-test at a frequency which is not resonant. Thus, during the self-test procedure a signal should be generated which would otherwise indicate the presence of air in the line. The generation of an air-in-line signal during the self-test procedure is an indication that the system is functioning properly.

Figure 108:
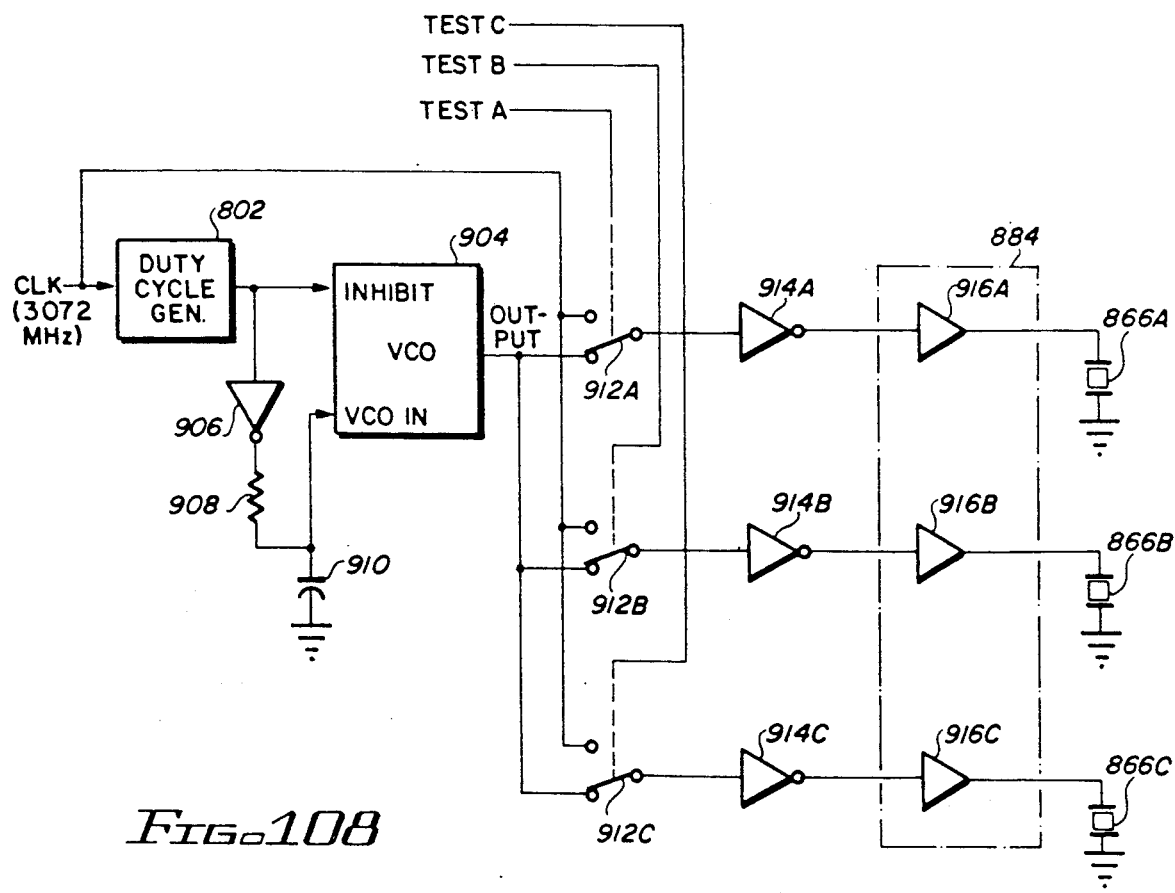
FIG. 108 is a schematic diagram of the transmitting circuitry for the ultrasonic air-in-line detector system for all three channels.

Referring next to FIG. 108, a clock having an operating frequency of 3.072 MHz is used to drive the transmitter circuitry. The clock signal is supplied to a duty cycle generator 902, which generates a 166 μS low pulse once every 1.33 mS (750 Hz). The 750 Hz rate is chosen to be sufficiently often to detect a bubble at even the highest flow rates through the outlet tube 306. The pulse is thus on a one-eighth duty cycle, which is used to conserve power in the system. The output pulse train of the duty cycle generator 902 is supplied as the inhibit input to a voltage controlled oscillator (VCO) 904.

The output pulse train from the duty cycle generator 902 is also supplied as an input to a inverter 906. The output of the inverter 906 is supplied to one side of a resistor 908, the other side of which is connected to the VCO in pin of the VCC 904. A capacitor 910 is connected on one side to the VCO in pin of the VCO 904, and on the other side to ground. The resistor 908 and the capacitor 910 act as an RC integrator to integrate the inverted inhibit waveform. The inhibit waveform supplied to the VCO 904 and the VCO input waveform supplied to the VCO 904 are illustrated in FIG. 111.

The output of the VCO 904 will be a variable frequency sweeping from a lower frequency to a higher frequency. The resonant frequency of the ultrasonic transducers 866 and 868 is nominally 1.8 MHz. Unless the ultrasonic transducers 866 and 868 are high precision devices, the exact resonant frequencies may vary somewhat, and may also vary slightly over a period of time. Thus, the VCO 904 is used to generate a variable frequency sweeping from, for example, 1.3 MHz to 2.3 Mhz, a sweep which is certain to include the resonant frequency of the ultrasonic transducers 866 and 868.

Figure 111:
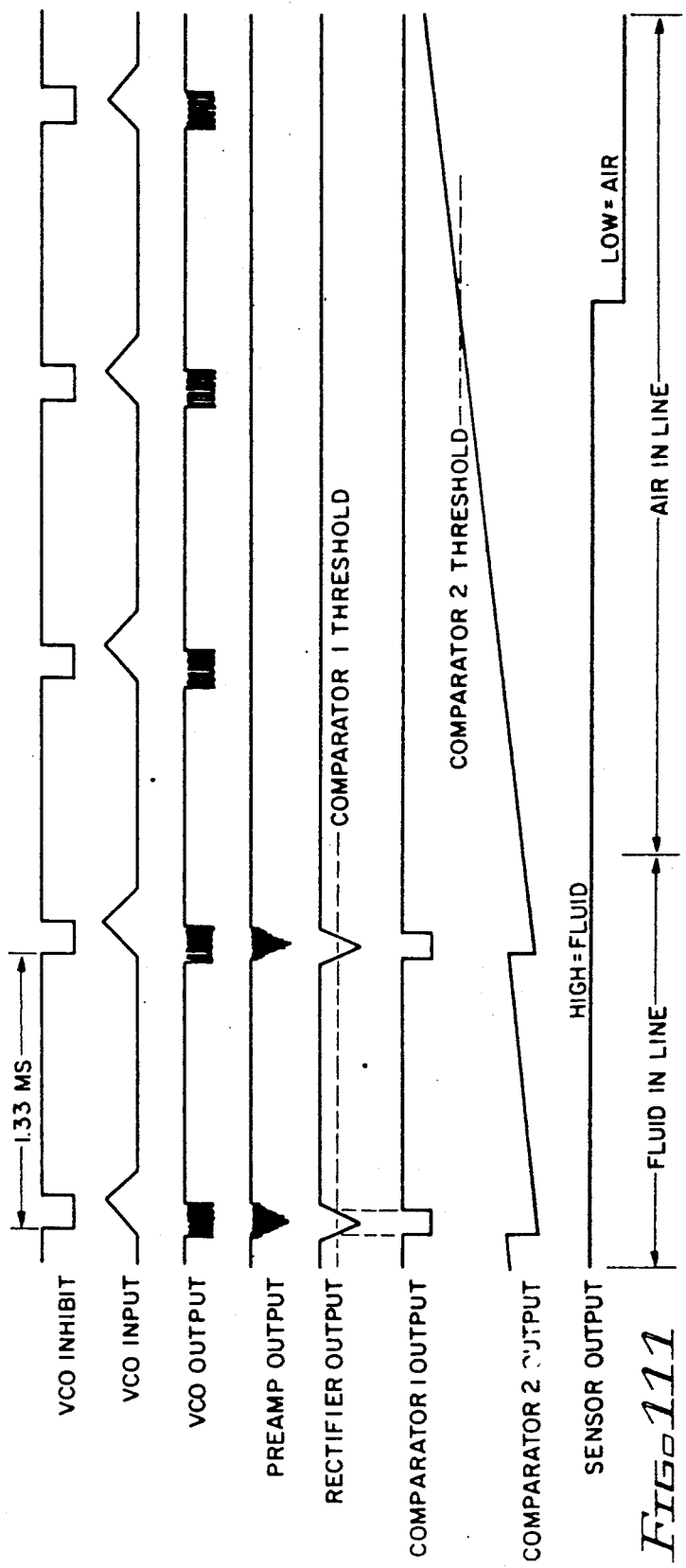
FIG. 111 shows various waveforms generated by the circuitry of FIGS. 108, 109, and 110.

This sweep will be generated on the one-eight duty cycle as shown in FIG. 111, thereby conserving energy required by the VCO 904 while repeating the sweep on a 750 Hz frequency to detect bubbles even at the fastest flow rate.

Referring again to FIG. 108, the output of the VCO 904 is supplied to one input side of three single-pole, double-throw switches 912A, 912B, and 912C. The other input side of these switches 912A, 912B, and 912C is connected directly to the 3.072 MHZ clock. The outputs of the switches 912A, 912B, and 912C may thus be switched between the output of the VCO 904 and the 3.072 MHz clock. Normally, the outputs of the switches 912A, 912B, and 912C are connected to the output of the VCO 904. Only when the self-test is to be performed are the outputs of the switches 912A, 912B, and 912C connected to the 3.072 MHz clock signal.

The outputs of the switches 912A, 912B, and 912C are connected to the input side of three inverters 914A, 914B, and 914C, respectively. The outputs of the three inverters 914A, 914B, and 914C are connected to the inputs of three buffers 916 A, 916B, and 916C, respectively, The three buffers 916A, 916B, and 916C are each contained on one of the printed circuit boards 884 (FIG. 87) used for the three channels. The outputs of the three buffers are connected to one side of three (one for each channel) ultrasonic transducers 866A, 866B, and 866C, respectively. The other sides of the three ultrasonic transducers 866A, 866B, and 866C are grounded.

Referring again to FIG. 111 in addition to FIG. 108, it is apparent that the three ultrasonic transducers 866A, 866B, and 866C will be excited with a sweeping frequency from 1.3 MHz to 2.3 MHz on a one-eighth duty cycle once every 1.33 mS (750 Hz). This is frequent enough so that even at the maximum pumping rate only a small amount of fluid can pass past the position of the ultrasonic transducer pairs between sequential ultrasonic transmissions. The one-eighth duty cycle conserves energy used by both the VCO 904 and the three ultrasonic transducers 866A, 866B, and 866C.

Figure 109:
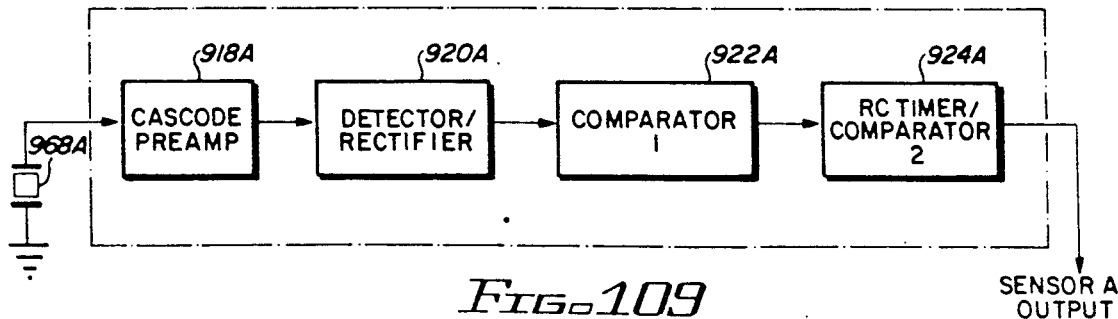
FIG. 109 is a functional schematic diagram of the receiver circuitry for one channel, the circuitry having an output signal.

FIG. 109 illustrates the receiver circuitry used for one of the three channels, with the other two channels using identical circuitry. The receiving transducer for the first channel is the ultrasonic transducer 868A, the output of which is supplied to a cascode preamplifier 918A. The output of the cascode preamplifier 918A will be a signal increasing in strength at the resonant frequency when fluid is present, and thus having a triangular envelope as illustrated in FIG. 111. The output of the cascode preamplifier 918A is supplied to a detector/rectifier 920A, the output of which is the rectifier output shown in FIG. 111.

The output of the detector/rectifier 920A is supplied to a first comparator 922A, which produces the waveform shown in FIG. 111 when the envelope from the detector/rectifier 920A is below a threshold. The output from the first comparator 922A is supplied to an RC Timer/second detector 924A, which integrates the output from the first comparator 922A, as shown in FIG. 111. The integrated output is reset each time there is a signal from the ultrasonic transducer 868A which is over the threshold of the first comparator 922A. When there is air in the line, the integrated signal will not be reset, causing it to reach the threshold of the second comparator. At this point, the output of the sensor A circuitry will go low.

In summary, when there is fluid in the outlet tube 306, the ultrasonic transducer 868A will receive a strong signal, and a high sensor A output will be given indicating the presence of fluid in the outlet tube 306. When there is air in the outlet tube 306, the ultrasonic transducer 868A will receive a weak signal, and a low sensor A output will be given indicating the presence of air in the outlet tube 306. Circuitry identical to that shown in FIG. 109 is used for the other two channels.

Figure 110:
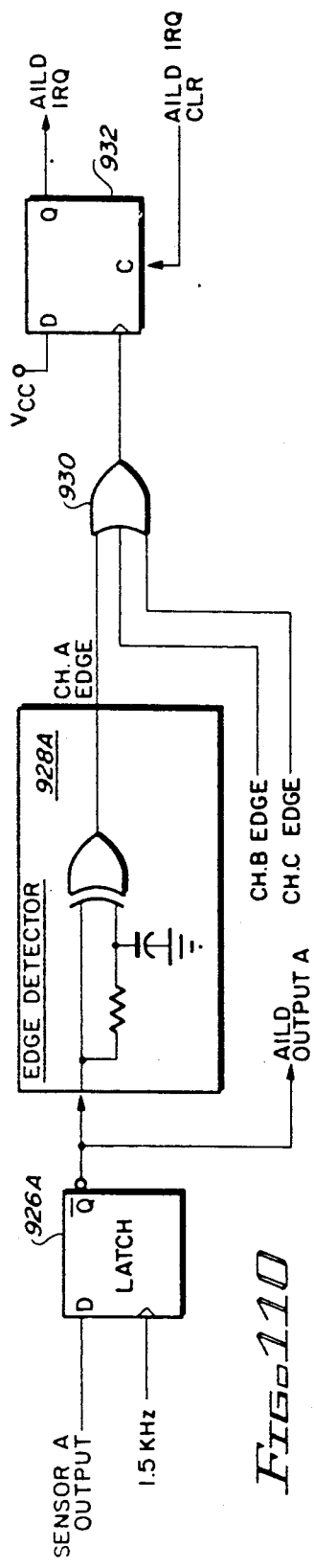
FIG. 110 is a schematic diagram of the processing circuitry used to process the output signal from the receiver circuitry to produce an AILD Output signal for each channel and an interrupt signal indicating a change in state of the AILD Output signal of one of the three channels.

Referring now to FIG. 110, additional processing circuitry used to obtain the two signals used by the AILD monitoring system 898 and the self-test system 900 of FIG. 107 is illustrated. The sensor A output is supplied to the D input of a latch 924A, the output of which is AILD output A. AILD output A will be low when fluid is in the outlet tube 306, and high when air is in the outlet tube 306. AILD output A is supplied to an edge detector 926A (one possible circuit for which is illustrated), the output of which will be a Channel A edge signal indicating either a rising or a falling edge in AILD output A. Thus, whenever an air/fluid interface is detected, the edge detector 928 A will produce an output signal.

The other two channels use similar circuitry to produce corresponding signals. Thus, an AILD output B and a Channel B edge signal will be produced by circuitry for Channel B. Similarly, an AILD output C and a Channel C edge signal will be produced by circuitry for Channel C.

The Channel A edge signal, the Channel B edge signal, and the Channel C edge signal are supplied to an OR gate 930. The output of the OR gate 930 will be high if any of the three inputs are high. Thus, whenever an edge is present in any of AILD output A, AILD output B, or AILD output C, the output of the OR gate 930 will be high. The output of the OR gate 930 is used to latch a latch 932 high, to generate an interrupt signal AILD IRQ. This interrupt signal indicates that a change in state of one of AILD output A, AILD output B, or AILD output C has occurred.

Thus, the circuitry of FIG. 110 will generate two signals. The first signal indicates the presence of air or fluid in the outlet tube 306 of a channel, and the second signal indicates a change in state in one of the three channels. The first signal thus comprises the signals AILD output A, AILD output B, or AILD output C, while the second signal is the interrupt signal AILD IRQ. For the rest of the explanation of the operation of the system, only the first channel (channel A) will be discussed. The operations of the other two channels (channels B and C) are identical in operation to the operation of the first channel.

Prior to a discussion of the operation of the AILD monitoring system 898, the concept of controlling the amount of air which may be pumped into a patient must first be discussed. First, it must be realized that it is not harmful to pump a small amount of air intravenously into many patients; in fact, many medications are not degassed and will contain some amount of air therein, which air may form small bubbles. Only a few patients can tolerate no air introduced into their venous systems, such as neonates, pediatrics, and those patients having septal defects. Other than when infusing fluid into such patients, or performing an intra-arterial infusion, the introduction of a very small quantities of air is not believed to be particularly harmful. The attending physician also has the option of using air eliminating filters in such patients.

The other problem faced in monitoring air in the fluid line to a patient is that it is undesirable to have too many alarms due to extremely small amounts of air being infused into most patients. The professional staff in most hospitals tend to view such frequent alarms as nuisance alarms which are undesirable and serve no useful purpose. Thus, the real purpose of an AILD system is to prevent unduly large, potentially dangerous quantities of air from being pumped into a patient. It is therefore necessary for the AILD system to allow some air past it without alarming, since a failure to do so could result in a large number of nuisance alarms. The AILD system must always alarm at some threshold, which has been selected as being high enough to prevent nuisance alarms but yet low enough to uniformly sense an amount of air presenting even a remote threat to the health of the patient. This objective may be implemented by using the concept of windowing.

The concept of windowing is when the passage of air bubbles in the immediately previous preset volume of fluid is remembered. Such a window is used to monitor the amount of air which may be included in a the most recent amount of a particular volume pumped to the patient. For example, in the last 2 milliliters of volume pumped, less than 100 microliters of air may be present without an alarm. As soon as 100 microliters of air is present in the last 2 milliliters of volume pumped, an alarm is to be given. This may be seen as a "forgetting" factor wherein all air bubbles pumped prior to the last 2 milliliters of volume pumped are forgotten by the system.

Such a volume window allows a particular amount of air less than a predetermined volume to be pumped within the last predetermined window volume. In the preferred embodiment the predetermined volume is one-twentieth (0.05) of the window volume. The window volume may be up to three milliliters, which is less than the volume of the delivery tubing 303. Thus, for a 50 microliter predetermined volume the window volume would be 1 milliliter, and for a 100 microliter predetermined volume the window volume would be 2 milliliters.

In some circumstances a larger predetermined volume may be appropriate. In any event, it will be realized by those skilled in the art that the proportion could be varied from perhaps one-one hundredth (with an substantial increase in the number of nuisance alarms) to perhaps as low as one-sixth (with special precautions such as the use of an air filter being taken). The preferred proportion is approximately one-twentieth.

The windowing scheme used by the present invention uses two pieces of information to determine whether the system has just pumped air or fluid in the immediately preceding time period since the next previous update. First, the sensor will detect whether there is currently air in the line at the sensor location. The second piece of information is whether at the immediately preceding time period at which information was being gathered there was air or fluid at the sensor location. This second information will thus indicate whether the bubble currently sensed is a continuation of a bubble started earlier, or the leading edge of a new bubble. Thus whether the system has just been pumping fluid or air in the immediately preceding time interval since the last update may be determined.

For example, if the current sensor reading indicates air in the line and the immediately previous reading was also air, then there is at the present time a continuing air bubble present in the fluid line. If the current sensor reading indicates air in the line and the immediately previous reading was fluid, then the leading edge of an air bubble has been sensed. If current sensor reading indicates fluid in the line and the immediately previous reading was air, then the trailing edge of an air bubble has been sensed. If current sensor reading indicates fluid in the line and the immediately previous reading was also fluid, then there is at the present time a continuing segment of fluid present in the fluid line.

The operation of the AILD monitoring system 898 may now be discussed with reference to the flow chart of FIG. 112. The operation is a circuitous one, repeating at a high frequency, and beginning at block 934. Since the system discussed herein is a three channel system, only the operation of the first channel (Channel A) will be discussed; the operation of the other two channels (Channels B and C) is identical. In block 934 it is determined whether an interrupt signal AILD IRQ has been generated. If no interrupt signal has been generated, the operation goes to block 936. If an interrupt signal has been generated, the latch 932 (FIG. 110) is reset by an AILD IRQ CLR signal on pin C. The operation would then proceed to block 938.

In block 936 it is determined whether the end of a delivery stroke in the pump 890 (FIG. 107) has been reached. If the end of a delivery stroke has not been reached, the operation returns to block 934. If the end of a delivery stroke has been reached, the operation would then proceed to block 938. Thus, it is apparent that the chain of events beginning at block 938 will be initiated either if an interrupt signal is generated or if the end of a delivery stroke has been reached.

In block 938 the AILD output is read; for channel A, AILD output A would be read. Then, in block 940, the encoder output (for encoder A) is read. This will indicate how much volume has been pumped since the last time the operation occurred. Then, in block 942, the pressure output (for channel A) is read. This may be used to normalize the volume pumped using Boyle's law ($P_1*V_1 = P_2*V_2$). Then, in block 944, a determination is made whether AILD output A indicates that there is currently air in the line at the sensor location. This is the first piece of information mentioned above, and it enables the system to divide into one of two branches depending on the outcome of the determination.

If there is currently air in the portion of the fluid line where the sensor is located, the system moves to block 946; if there is currently no air in the portion of the fluid line where the sensor is located, the system moves to block 948. The operations which follow block 946 thus follow a determination that there is currently air in the tubing at the sensor location. Similarly, the operations which follow block 948 follow a determination that there is currently no air in the tubing at the sensor location. In each case, the second piece of information, whether at the immediately preceding time period at which information was gathered there was air or fluid at the sensor location, must next be evaluated for each of the two possibilities in blocks 946 and 948.

First in block 946, a determination is made as to whether at the immediately preceding cycle during which information was gathered there was air or fluid at the sensor location. If the determination is made that there was air in the tubing at the sensor location at the time of this next previous update, the system will move to block 950. If, on the other hand the determination is made that there was no air in the tubing at the sensor location at the time of this next previous update, the system will move to block 952.

Thus, the block 950 will be reached if the current sensor reading indicates air in the line and the immediately previous reading also indicated the presence of air in the line. In this case, there is an air bubble in the line which existed at the next previous sensor reading and which still exists. Thus, in the block 950 the additional volume of the air bubble between the time of the next previous sensor reading and the present time is computed. Then, in block 954, the window is updated to calculate how much of the volume window is currently air bubbles.

In block 954 the additional volume of the air bubble between the time of the next previous sensor reading and the present time is added to the volume of air contained in the volume window, and air bubbles now beyond the back edge of the window are subtracted from the volume of air contained in the volume window. In this manner, the volume window is updated to determine the volume of gas bubbles in the last volume window volume to pass through the ultrasonic sensor.

The sequence would then move to block 960, in which a determination is made as to whether the portion of the volume window which is air bubbles exceeds the predetermined maximum. If the portion of the volume window which is air bubbles exceeds the predetermined maximum, the system moves to block 962, and an alarm is sounded and the pumping of fluid by the system will be ceased. If the portion of the volume window which is air bubbles does not exceed the predetermined maximum, the system moves back to block 934.

The block 952 will be reached if the current sensor reading indicates air in the line and the immediately previous reading indicated the presence of fluid in the line. In this case, there is an air bubble in the line which did not exist at the next previous sensor reading, but rather has just started (the starting edge of the bubble has been detected). Thus, in the block 952 the additional volume of the fluid between the time of the next previous sensor reading up to the beginning of the bubble is computed. Then, in block 956, the window is updated to calculate how much of the volume window is air bubbles.

In the preferred embodiment, an allowance is made for the fact that an air bubble must be at least a minimum size before it can be detected. Thus, when an air bubble is first detected, it is assumed that it is at least this minimum bubble size up to this point. The minimum bubble size used in the preferred embodiment is 6 microliters.

In block 956, since there is fluid between the time of the next previous sensor reading and the present time, only the minimum bubble size of 6 microliters is added to the volume of air contained in the volume window, and air bubbles now beyond the back edge of the window are subtracted from the volume of air contained in the volume window. In this manner, the volume window is updated to determine the volume of air bubbles in the last volume window volume to pass through the ultrasonic sensor.

In block 958, the window information is switched to indicate that the present information, soon to become the next previous update, indicates the presence of air. Thus, the next time the system moves through the loop, the second piece of information will indicate that at the previous update, there was air present in the tubing.

The sequence would then move to block 960, in which a determination is made as to whether the portion of the volume window which is air bubbles exceeds the predetermined maximum. If the portion of the volume window which is air bubbles exceeds the predetermined maximum, the system moves to block 962, and an alarm is sounded and the pumping of fluid by the system will be ceased. If the portion of the volume window which is air bubbles does not exceed the predetermined maximum, the system moves back to block 934.

Alternatively, if there is presently no air in the line in block 944, the system would have moved to block 948. In block 948, a determination is made as to whether at the immediately preceding time period at which information was gathered there was air or fluid at the sensor location. If the determination is made that there was air in the tubing at the sensor location at the time of this next previous update, the system will move to block 964. If, on the other hand the determination is made that there was no air in the tubing at the sensor location at the time of this next previous update, the system will move to block 966.

Thus, the block 964 will be reached if the current sensor reading indicates a lack of air presently in the line, but the immediately previous reading indicated the presence of air in the line. In this case, there was an air bubble in the line which existed at the next previous sensor reading, but which bubble ended (the trailing edge of an air bubble has been detected). Thus, in the block 964 the additional volume of the gas bubble between the time of the next previous sensor reading and its ending point at the present time is computed. Then, in block 968, the window is updated to calculate how much of the volume window is air bubbles.

In block 968 the additional volume of the air bubble from the time of the next previous sensor reading which ended at the present time is added to the volume of air contained in the volume window, and air bubbles now beyond the back edge of the window are subtracted from the volume of air contained in the volume window. In this manner, the volume window is updated to determine the volume of air bubbles in the last volume window volume to pass through the ultrasonic sensor.

In block 972, the window information is switched to indicate that the present information, soon to become the next previous update, indicates the absence of air. Thus, the next time the system moves through the loop, the second piece of information will indicate that at the previous update, there was no air present in the tubing.

The sequence would then move to block 960, in which a determination is made as to whether the portion of the volume window which is air bubbles exceeds the predetermined maximum. If the portion of the volume window which is air bubbles exceeds the predetermined maximum, the system moves to block 962, and an alarm is sounded and the pumping of fluid by the system will be ceased. If the portion of the volume window which is air bubbles does not exceed the predetermined maximum, the system moves back to block 934.

The block 966 will be reached if the current sensor reading indicates no air in the line and the immediately previous reading also indicated the presence of fluid in the line. In this case, there is and has been fluid in the line from the time of the immediately previous reading to the present. Thus, in the block 966 the additional volume of the fluid between the time of the next previous sensor reading up to the beginning of the bubble is computed. Then, in block 970, the window is updated to calculate how much of the volume window is air bubbles.

In block 970, since there is fluid between the time of the next previous sensor reading and the present time, no additional volume of air is added to the volume of air contained in the volume window, and air bubbles now beyond the back edge of the window are subtracted from the volume of air contained in the volume window. In this manner, the volume window is updated to determine the volume of air bubbles in the last volume window volume to pass through the ultrasonic sensor.

The sequence would then move to block 960, in which a determination is made as to whether the portion of the volume window which is air bubbles exceeds the predetermined maximum. If the portion of the volume window which is air bubbles exceeds the predetermined maximum, the system moves to block 962, and an alarm is sounded and the pumping of fluid by the system will be ceased. If the portion of the volume window which is air bubbles does not exceed the predetermined maximum, the system moves back to block 934.

Figure 112:
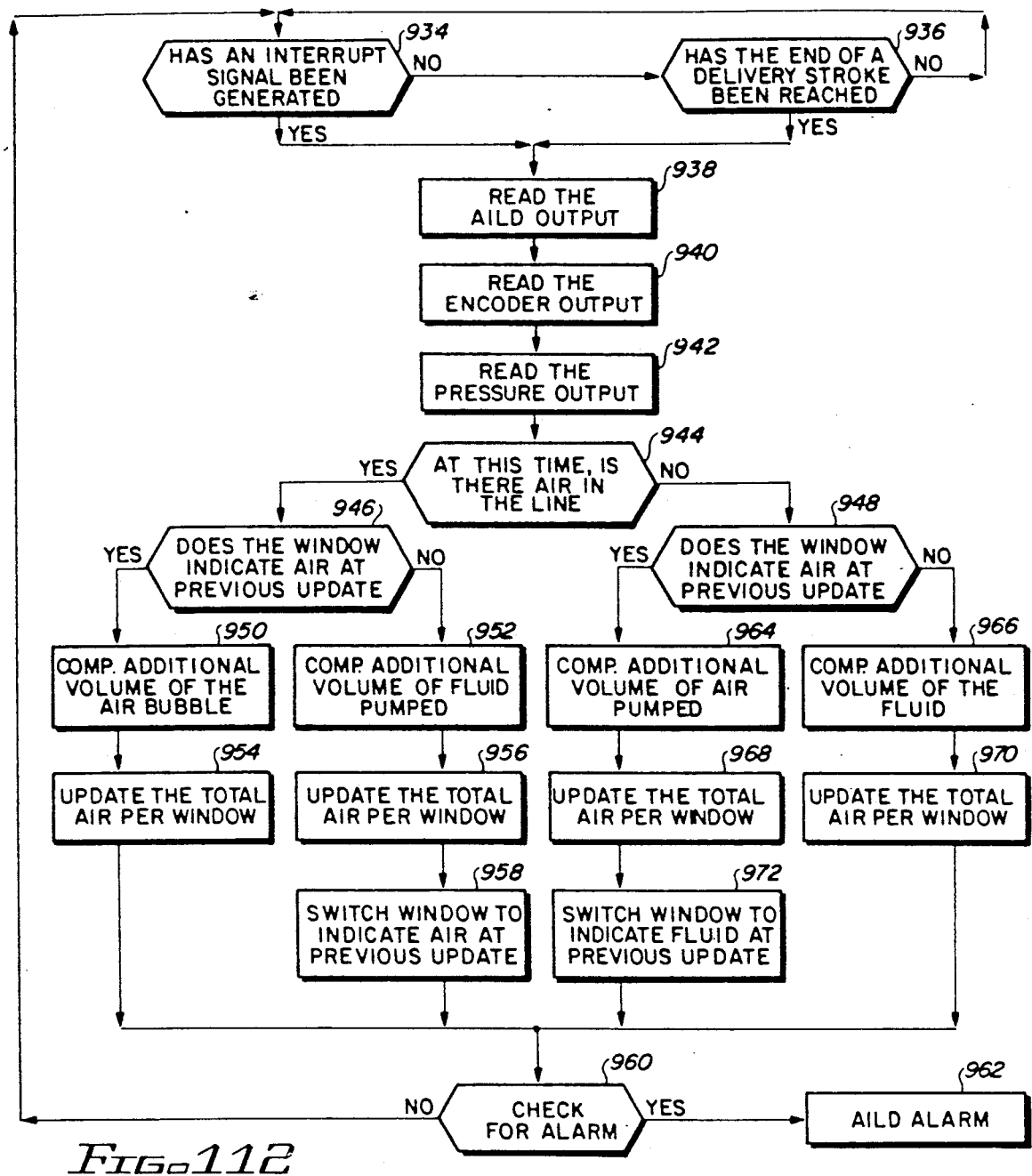
FIG. 112 is a simplified flow diagram illustrating the operation of the air-in-line detector monitoring system.

It must be realized that the flow chart of FIG. 112 represents a highly simplified example of how the system may be implemented to perform the windowing function. Those skilled in the art will immediately understand the principles behind this operation, and will be able to implement it in a variety of manners. The advantages of the technique are self-evident—the pumping of an excessive amount of air into a patient is avoided, while the occurrence of nuisance alarms is avoided.

Turning now to FIG. 113, the operation of the self-test system is illustrated in a simplified manner. The self-test is performed in the preferred embodiment once per cycle after it has been determined that the end of a delivery cycle has been reached, assuming that the portion of the volume window which is air bubbles did not exceed the predetermined maximum. The initial determination is made in block 980 whether the end of a delivery cycle has been reached. If the end of a delivery cycle has been reached, the system moves to block 982. If the end of a delivery cycle has not been reached, the system moves back to the beginning of block 980.

A determination is made in block 982 whether AILD output A whether that there is currently air in the line at the sensor location. If there is air in the line, the self-test may not be run, and the system moves back to the beginning of block 980. If there is not currently air in the sensor, the system moves to block 984.

In block 984, the frequency supplied to the ultrasonic transducer 866A is changed to a non-resonant frequency. (Referring briefly to FIG. 108, the switch 912A would be switched to connect the 3.072 MHz clock to the inverter 914A.) This frequency is far enough from the resonant frequency that the ultrasonic transducer 868A will not resonate. At this point, the AILD output A should indicate air and an interrupt signal should quickly be generated. If a signal is generated by the ultrasonic transducer 868B, this would indicate that there is a failure in the ultrasonic transducer 868B or in the associated electronics.

Accordingly, in block 986 if the interrupt signal does not appear within a preset time it will be apparent that there is an error, and the AILD fault signal 987 will be sounded and the pumping operation ceased. If the interrupt signal appears within the preset time, it is an indication that the system is functioning properly, and system will move on to block 988. In block 988, the frequency supplied to the ultrasonic transducer 866A is changed back to the periodic resonant frequency encompassing sweep. (Referring briefly to FIG. 108, the switch 912A would be switched to connect the output of the VCO 904 to the inverter 914A.) The system will move back to the beginning of block 980, and the sequence will be repeated.

Through the above discussion of the entire system, it will be appreciated that the present invention provides a self-test system which will detect all such non-fail-safe occurrences. Thus, the self-test system will detect the occurrence of a receiver output stuck high and provide an alarm and shut down the pumping system. The self-test system also will detect the occurrence of electrical coupling which causes a false indication of the presence of fluid in the fluid line, and provide an alarm and shut down the pumping system.

The self-test system performs the self-test periodically, and sufficiently often to ensure that such a failure will be detected promptly before air can be pumped into the patient. The self-test system uses no additional components, and requires no modification to the cassette, yet it affords the highest degree of accuracy in detecting a system fault. The system accomplishes all these objects in a manner which retains and enhances the advantages of reliability, durability, and safety of operation, without incurring any relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. In an ultrasonic air-in-line detection system having an ultrasonic transmitter driven at a first resonant frequency and an ultrasonic receiver for producing a first output signal when there is fluid in a fluid passageway and a second output signal when there is an air bubble in the fluid passageway, a self-test system comprising:

means for driving said ultrasonic transmitter at a second non-resonant frequency;

means for monitoring the output signal from said ultrasonic receiver to determine whether said first output signal or said second output signal is produced; and means for providing a fault signal if said monitoring means determines that said first output signal is produced by said ultrasonic receiver when said ultrasonic transmitter is driven at said second non-resonant frequency.

2. A self-test system as defined in claim 1, wherein said ultrasonic transmitter comprises:

a first ultrasonic transducer located on one side of said fluid passageway, said first ultrasonic transducer being resonant at said first resonant frequency; and means for selectively driving said first ultrasonic transducer either at said first resonant frequency or at a second non-resonant frequency at which said first and second ultrasonic transducers are not resonant, said first ultrasonic transducer when driven at said first frequency generating ultrasonic vibrations which are transmitted to said one side of said fluid passageway, said ultrasonic vibrations passing through said fluid passageway and being received by said second ultrasonic transducer when there is fluid in said fluid passageway, said ultrasonic vibrations substantially not passing through said fluid passageway and not being received by said second ultrasonic transducer when there is an air bubble in said fluid passageway; and wherein said ultrasonic receiver comprises:

a second ultrasonic transducer located on the other side of said fluid passageway, said second ultrasonic transducer also being resonant at said first resonant frequency; and receiver means for detecting ultrasonic vibrations received by said second transducer and providing either said first output signal or said second output signal.

3. A self-test system as defined in claim 2, wherein the resonant frequency of said first ultrasonic transducer is approximately said first resonant frequency.

4. A self-test system as defined in claim 2, wherein the resonant frequency of said second ultrasonic transducer is approximately said first resonant frequency.

5. A self-test system as defined in claim 1, wherein said ultrasonic transducer is driven by a variable frequency ranging from a third frequency to a fourth frequency, said first resonant frequency falling in the range between said third frequency and said fourth frequency, said second non-resonant frequency not in the range between said third frequency and said fourth frequency.

6. A self-test system as defined in claim 1, wherein said second non-resonant frequency varies substantially from said first resonant frequency.

7. A self-test system as defined in claim 1, wherein said driving means comprises:

a source of said second non-resonant frequency; and switch means for switching between said first resonant frequency and said second non-resonant frequency.

8. A self-test system as defined in claim 1, wherein said driving means periodically drives said ultrasonic transmitter at said second non-resonant frequency.

9. A self-test system as defined in claim 1, wherein said driving means does not drive said ultrasonic transmitter at said second non-resonant frequency if said second output signal is being produced by said ultrasonic receiver.

10. A self-test system as defined in claim 1, wherein said driving means drives said ultrasonic transmitter at said second non-resonant frequency only sufficiently long to determine whether said first output signal or said second output signal is produced.

11. A self-test system as defined in claim 1, wherein said means for providing a fault signal provides an audible or visible alarm signal and shuts down the pumping operation through said fluid passageway.

12. An ultrasonic air-in-line detection system including a self-test mode for testing the ultrasonic air-in-line detection system to ensure that it is operating properly, comprising:

a first ultrasonic transducer located on one side of a fluid passageway, said first ultrasonic transducer being resonant at a first frequency;

a second ultrasonic transducer located on the other side of said fluid passageway;

means for selectively driving said first ultrasonic transducer either at said first frequency or at a second frequency at which said first and second ultrasonic transducers are not resonant, said first ultrasonic transducer when driven at said first frequency generating ultrasonic vibrations which are transmitted to said one side of said fluid passageway, said ultrasonic vibrations passing through said fluid passageway and being received by said second ultrasonic transducer when there is fluid in said fluid passageway, said ultrasonic vibrations substantially not passing through said fluid passageway and not being received by said second ultrasonic transducer when there is an air bubble in said fluid passageway;

receiver means for detecting the ultrasonic vibrations received by said second transducer and providing either a first output signal indicative of there presently being fluid in said fluid passageway between said first and second transducers or a second output signal indicative of there presently being an air bubble in said fluid passageway between said first and second transducers;

self-test means for causing said driving means to drive said first transducer at said second frequency and determining whether said first output signal or said second output signal is generated by said receiver means; and means for generating a fault signal when said self-test means determines that said first output signal is generated by said receiver means when said driving means is driving said first transducer at said second frequency.

13. In an ultrasonic air-in-line detection system having an ultrasonic transmitter driven by a frequency sweep signal encompassing a resonant frequency and an ultrasonic receiver for producing a first output signal when there is fluid in a fluid passageway and a second output signal when there is an air bubble in the fluid passageway, a self-test system comprising:

means for driving said ultrasonic transmitter at a non-resonant frequency;

means for monitoring the output signal from said ultrasonic receiver to determine whether said first output signal or said second output signal is produced; and means for providing a fault signal if said monitoring means determines that said first output signal is produced by said ultrasonic receiver when said ultrasonic transmitter is driven at said non-resonant frequency.

14. In an ultrasonic air-in-line detection system having an ultrasonic transmitter driven at a first resonant frequency and an ultrasonic receiver for producing a first output signal when there is fluid in a fluid passageway and a second output signal when there is an air bubble in the fluid passageway, a method of testing said ultrasonic air-in-line detection system to ensure that it is operating properly comprising:

driving said ultrasonic transmitter at a second non-resonant frequency;

monitoring the output signal from said ultrasonic receiver to determine whether said first output signal or said second output signal is produced; and means for providing a fault signal if in said monitoring step it is determined that said first output signal is produced by said ultrasonic receiver when said ultrasonic transmitter is driven at said second non-resonant frequency.

15. A method as defined in claim 14, additionally comprising:

initially determining whether said first output signal or said second output signal is being produced by said ultrasonic transmitter, and, if said second output signal is being produced, not driving said ultrasonic transmitter at said second non-resonant frequency.

16. A method as defined in claim 14, additionally comprising:

allowing said ultrasonic transmitter to be driven at said first resonant frequency if in said monitoring step it is determined that said second output signal is produced by said ultrasonic receiver when said ultrasonic transmitter is driven at said second non-resonant frequency.

* * * * *

UNITED STATES PATENT AND TRADEMARK OFFICE
CERTIFICATE OF CORRECTION

PATENT NO. : 5,053,747
DATED : Oct. 1, 1991
INVENTOR(S) : John B. Slate, James L. Henke It is certified that error appears in the above-indentified patent and that said Letters Patent is hereby corrected as shown below:

```
Column 10, line 53, change "10", to read --102--
Column 13, line 49, change "18", to read --180--.
Column 18, line 16, change "26", to read --264--.
Column 28, line 33, change "24", to read --248--.
Column 29, line 9,  change "56", to read --566--.
Column 47, line 51, "3.072MHz" should not be bold face.
```

Signed and Sealed this

Seventeenth Day of June, 1997

Attest:

BRUCE LEHMAN

Attesting Officer

Commissioner of Patents and Trademarks